US007982017B2

(12) United States Patent
Lin et al.

(10) Patent No.: US 7,982,017 B2
(45) Date of Patent: Jul. 19, 2011

(54) ANTIBODIES RECOGNIZING A CARBOHYDRATE CONTAINING EPITOPE ON CD-43 AND CEA EXPRESSED ON CANCER CELLS AND METHODS USING SAME

(75) Inventors: Shih-Yao Lin, Taipei (TW); Leewen Lin, Taipei (TW); Yu-Ying Tsai, Taipei (TW)

(73) Assignee: BioAlliance C.V. (NL)

( * ) Notice: Subject to any disclaimer, the term of this patent is extended or adjusted under 35 U.S.C. 154(b) by 53 days.

(21) Appl. No.: 12/338,934

(22) Filed: Dec. 18, 2008

(65) Prior Publication Data

US 2009/0191221 A1 Jul. 30, 2009

Related U.S. Application Data

(60) Provisional application No. 61/014,716, filed on Dec. 18, 2007.

(51) Int. Cl.
*C07K 16/00* (2006.01)
*C12P 21/08* (2006.01)
*C12P 21/04* (2006.01)
*A61K 39/395* (2006.01)
*A61K 39/00* (2006.01)

(52) U.S. Cl. .............. 530/388.23; 530/387.3; 530/388.1; 424/130.1; 424/133.1; 424/145.1; 435/69.6

(58) Field of Classification Search .................. None
See application file for complete search history.

(56) References Cited

U.S. PATENT DOCUMENTS

| | | |
|---|---|---|
| 4,036,945 A | 7/1977 | Haber |
| 4,331,647 A | 5/1982 | Goldenberg |
| 4,676,980 A | 6/1987 | Segal et al. |
| 4,683,195 A | 7/1987 | Mullis et al. |
| 4,683,202 A | 7/1987 | Mullis |
| 4,754,065 A | 6/1988 | Levenson et al. |
| 4,777,127 A | 10/1988 | Suni et al. |
| 4,800,159 A | 1/1989 | Mullis et al. |
| 4,816,567 A | 3/1989 | Cabilly et al. |
| 5,047,335 A | 9/1991 | Paulson et al. |
| 5,219,740 A | 6/1993 | Miller et al. |
| 5,278,299 A | 1/1994 | Wong et al. |
| 5,314,995 A | 5/1994 | Fell, Jr. et al. |
| 5,422,120 A | 6/1995 | Kim |
| 5,500,362 A | 3/1996 | Robinson et al. |
| 5,510,261 A | 4/1996 | Goochee et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Felgner et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,677,427 A | 10/1997 | Goldenberg et al. |
| 5,693,761 A | 12/1997 | Queen et al. |
| 5,693,762 A | 12/1997 | Queen et al. |
| 5,733,743 A | 3/1998 | Johnson et al. |
| 5,750,373 A | 5/1998 | Garrard et al. |
| 5,772,997 A | 6/1998 | Hudziak et al. |
| 5,807,715 A | 9/1998 | Morrison et al. |
| 5,814,482 A | 9/1998 | Dubensky, Jr. et al. |
| 5,821,337 A | 10/1998 | Carter et al. |
| 5,866,692 A | 2/1999 | Shitara et al. |
| 5,997,867 A | 12/1999 | Waldmann et al. |
| 6,048,703 A | 4/2000 | Siman et al. |
| 6,120,767 A | 9/2000 | Robinson et al. |
| 6,180,370 B1 | 1/2001 | Queen et al. |
| 6,265,150 B1 | 7/2001 | Terstappen et al. |
| 6,291,643 B1 | 9/2001 | Zou et al. |
| 6,329,508 B1 | 12/2001 | Friden |
| 6,331,415 B1 | 12/2001 | Cabilly et al. |
| 6,376,471 B1 | 4/2002 | Lawrence, III et al. |
| 6,413,942 B1 | 7/2002 | Felgner et al. |
| 6,436,908 B1 | 8/2002 | Koch et al. |
| 6,548,640 B1 | 4/2003 | Winter |
| 6,652,852 B1 | 11/2003 | Robinson et al. |
| 6,808,901 B1 | 10/2004 | Neuberger et al. |
| 7,674,605 B2 | 3/2010 | Lin et al. |
| 2003/0027763 A1 | 2/2003 | Bennett et al. |
| 2008/0171043 A1 | 7/2008 | Lin et al. |
| 2010/0124551 A1 | 5/2010 | Lin et al. |

FOREIGN PATENT DOCUMENTS

AU 37570/93 B 10/1993

(Continued)

OTHER PUBLICATIONS

Skolnick and Fetrow. From genes to protein structure and function: novel applications of computational approaches in the genomic era. Trends in Biotechnology, 2000. vol. 18, pp. 34-39.*

Burgess, Shaheen, Ravera, Jaye, Donohue, and Winkles. Possible dissociation of the heparin binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activities Molecular and Cellular Biology, 1988. vol. 8, pp. 1247-1252.*

Holm, Jafari, and Sundstrom. Functional mapping and single chain construction of the anti-cytokeratin 8 monoclonal antibody TS1. Molecular Immunology, 2007. vol. 44, pp. 1075-1084.*

(Continued)

*Primary Examiner* — Anne M. Gussow

(74) *Attorney, Agent, or Firm* — Morrison & Foerster LLP

(57) ABSTRACT

The present invention provides antibodies (such as chimeric and humanized antibodies) specifically bind to an epitope on CD43 and CEA expressed on nonhematopoietic cancer cells. In addition, the present invention also provides use of the antibodies described herein for diagnostic and therapeutic purposes.

32 Claims, 10 Drawing Sheets

FOREIGN PATENT DOCUMENTS

| | | |
|---|---|---|
| EP | 0 345 242 A2 | 12/1989 |
| EP | 0 345 242 A3 | 12/1989 |
| EP | 0 528 767 B1 | 2/1993 |
| EP | 0 396 387 B1 | 12/1993 |
| EP | 0 524 968 B1 | 7/1995 |
| EP | 1 782 838 A1 | 5/2007 |
| GB | 2200651 B | 8/1988 |
| WO | WO-87/04462 A1 | 7/1987 |
| WO | WO-89/12624 A2 | 12/1989 |
| WO | WO-89/12624 A3 | 12/1989 |
| WO | WO-90/07936 A1 | 7/1990 |
| WO | WO-90/11092 A1 | 10/1990 |
| WO | WO-91/00360 A1 | 1/1991 |
| WO | WO-91/00904 A1 | 1/1991 |
| WO | WO-91/02805 A2 | 3/1991 |
| WO | WO-91/02805 A3 | 3/1991 |
| WO | WO-91/14438 A1 | 10/1991 |
| WO | WO-91/14445 A1 | 10/1991 |
| WO | WO-92/08495 A1 | 5/1992 |
| WO | WO-92/20373 A1 | 11/1992 |
| WO | WO-93/03769 A1 | 3/1993 |
| WO | WO-93/06213 A1 | 4/1993 |
| WO | WO-93/10218 A1 | 5/1993 |
| WO | WO-93/11230 A1 | 6/1993 |
| WO | WO-93/19191 A1 | 9/1993 |
| WO | WO-93/25234 A1 | 12/1993 |
| WO | WO-93/25698 A1 | 12/1993 |
| WO | WO-94/03622 A1 | 2/1994 |
| WO | WO-94/04690 A1 | 3/1994 |
| WO | WO-94/12649 A2 | 6/1994 |
| WO | WO-94/12649 A3 | 6/1994 |
| WO | WO-94/23697 A1 | 10/1994 |
| WO | WO-94/28938 A1 | 12/1994 |
| WO | WO-95/00655 A1 | 1/1995 |
| WO | WO-95/07994 A2 | 3/1995 |
| WO | WO-95/07994 A3 | 3/1995 |
| WO | WO-95/11984 A2 | 5/1995 |
| WO | WO-95/11984 A3 | 5/1995 |
| WO | WO-95/13796 A1 | 5/1995 |
| WO | WO-95/30763 A2 | 11/1995 |
| WO | WO-95/30763 A3 | 11/1995 |
| WO | WO-96/17072 A1 | 6/1996 |
| WO | WO-97/42338 A1 | 11/1997 |
| WO | WO-99/58572 A1 | 11/1999 |
| WO | WO-2006/001348 A1 | 1/2006 |
| WO | WO-2007/146172 A2 | 12/2007 |
| WO | WO-2007/146172 A3 | 12/2007 |
| WO | WO-2007/146172 A8 | 12/2007 |
| WO | WO-2009/079649 A1 | 6/2009 |

OTHER PUBLICATIONS

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Al-Lazikani, B. et al. (Nov. 7, 1997). "Standard Conformations for the Canonical Structures of Immunoglobulins," *Journal of Molecular Biology* 273(4):927-948.

Baeckström, D. et al. (Nov. 15, 1991). "Purification and Characterization of a Membrane-Bound and a Secreted Mucin-Type Glycoprotein Carrying the Carcinoma-Associated Sialyl-le$_a$ Epitope on Distinct Core Proteins," *J. Biol. Chem.* 266(32):21537-21547.

Baeckström, D. et al. (Jun. 9, 1995). "Expression of the Leukocyte-associated Sialoglycoprotein CD43 by a Colon Carcinoma Cell Line," *Journal of Biological Chemistry* 270(23):13688-13692.

Baeckström, D. et al. (Apr. 25, 1997). "Post-translation Fate of Mucin-like Leukocyte Sialoglycoprotein (CD43) Aberrantly Expressed in a Colon Carcinoma Cell Line," *Journal of Biological Chemistry* 272(17):11503-11509.

Bažil, V. et al. (Feb. 15, 1996). "A Monoclonal Antibody Recognizing CD43 (leukosialin) Initiates Apoptosis of Human Hematopoietic Progenitor Cells But Not Stem Cells," *Blood* 87(4):1272-1281.

Belhocine, T. et al. (Feb. 2004). "The Imaging of Apoptosis with the Radiolabeled Annexin V: Optimal Timing for Clinical Feasibility," *Technology in Cancer Research and Treatment* 3(1):23-32.

Boerner, P. et al. (Jul. 1, 1991). "Production of Antigen-Specific Human Monoclonal Antibodies from In Vitro-primed Human Splenocytes," *Journal of Immunology* 147(1):86-95.

Boyd, P.N. et al. (1995). "The Effect of the Removal of Sialic Acid, Galactose and Total Carbohydrate on the Functional Activity of Campath-1 H," *Molecular Immunology* 32(17/18):1311-1318.

Brodeur, B.R. et al. (1987). "Mouse-Human Myeloma Partners for the Production of Heterohybridomas," Chapter 4, *In Monoclonal Antibody Production Techniques and Applications*, Schook, L. ed., Marcel Dekker Inc.: New York, NY, 51-63.

Brown, T.J. et al. (1996). "Characterization of a CD43/Leukosialin-Mediated Pathway for Inducing Apoptosis in Human T-Lymphoblastoid Cells," *Journal of Biological Chemistry* 271(44):27686-27695.

Burton, D.R. (1985). "Review. Immunoglobulin G: Functional Sites," *Mol. Immunol.* 22(3):161-206.

Cabilly, S. et al. (1984). "Generation of Antibody Activity from Immunoglobulin Polypeptide Chains Produced in *Escherichia coli*," *Proceedings of the National Academy of Sciences of the United States of America* 81(11):3273-3277.

Carlow, D.A., et al. (Jan. 1, 2001). "Absence of CD43 Fails to Alter T Cell Development and Responsiveness," *Journal of Immunology* 166(1):256-261.

Čermák, L. et al. (Mar. 8, 2002, e-pub. Dec. 31, 2001). "Molecular Mechanisms Involved in CD43-mediated Apoptosis of TF-1 cells. Roles of Transcription Daxx Expression, and Adhesion Molecules," *Journal of Biological Chemistry* 277(10):7955-7961.

Chevinsky, A. H. (May-Jun. 1991). "CEA in Tumors of Other Than Colorectal Origin," *Seminars in Surgical Oncology* 7(3):162-166.

Chiou, H.C. et al. (1994). "In Vivo Gene Therapy Via Receptor Mediated DNA Delivery," Chapter II Methods and Mechanisms, *In Gene Therapeutics: Methods and Applications of Direct Gene Transfer*, Wolff, J. A. ed., Birkhäuser: Boston, MA, pp. 143-156.

Chu, G. et al. (1987). "Electroporation for the Efficient Transfection of Mammalian Cells with DNA," *Nucleic Acids Research* 15(3):1311-1326.

Clackson, T. et al. (Aug. 1991). "Making Antibody Fragments Using Phage Display Libraries," *Nature* 352(6336):624-628.

Clynes, R. et al. (Jan. 1998). "Fc Receptors Are Required in Passive and Active Immunity to Melanoma," *Proceedings of the National Academy of Sciences of the United States of America* 95(2):652-656.

Co, M.S. et al. (Feb. 15, 1992). "Chimeric and Humanized Antibodies with Specificity for the CD33 Antigen," *J. Immunol.* 148(4):1149-1154.

Cole, S.P.C. et al. (1985). "The EBV-Hybridoma Technique and its Application to Human Lung Cancer," *Monoclonal Antibodies and Cancer Therapy*, Reisfeld, R.A. et al. ed., Alan R. Liss Inc., New York, NY, 77-96.

Connelly, S. et al. (Feb. 1995). "In Vivo Gene Delivery and Expression of Physiological Levels of Functional Human Factor VIII in Mice," *Human Gene Therapy* 6(2):185-193.

Curiel, D.T. et al. (1992). "High-Efficiency Gene Transfer Mediated by Adenovirus Coupled to DNA-Polylysine Complexes," *Human Gene Therapy* 3(2):147-154.

Dragone, L.L. et al. (Jan. 1995). "Disregulation of Leukosialin (CD43, Ly48, Sialophorin) Expression in the B-Cell Lineage of Transgenic Mice Increases Splenic B-Cell Number and Survival," *Proc. Natl. Acad. Sci. USA* 92:626-630.

Ellison, J. W. et al. (1981). "The Nucleotide Sequence of a Human Immunoglobulin C$_{\gamma 1}$ Gene," *Nucleic Acids Research* 10(13):4071-4079.

Fabbi, M. et al. (1994). "A Novel 120-kDa Antigen Shared by Immature Human Thmyocytes and Long-Term-Activated T Cells," *Eur. J. Immunol.* 24:1-7.

Fabbi, M. et al. (1999). "8B4/20, A Private CD43 Epitope on Developing Human Thymocytes, Is Involved in Thymocyte Maturation," *J. Immunol.* 163:5964-5970.

Fernandez-Rodriguez, J. et al. (2002). "The Leukocyte Antigen CD43 is Expressed in Different Cell Lines of Nonhematopoietic Origin," *Tumor Biology* 23(4):193-201.

Findeis, M.A. et al. (May 1993). "Targeted Delivery of DNA for Gene Therapy Via Receptors," *Trends in Biotechnology* 11(5):202-205.

Fuhlbrigge, R.C. et al. (Feb. 15, 2006). "CD43 is a Ligand for E-selectin on CLA+ Human T Cells," *Blood* 107(4):1421-1426.

Gazzano-Santoro, H. et al. (Mar. 28, 1997). "A Aon-Radioactive Complement-Dependent Cytotoxicity Assay for Anti-CD20 Monoclonal Antibody," *Journal of Immunological Methods* 202(2):163-171.

Gennaro, A.R. ed. (2000). *Remington: The Science and Practice of Pharmacy*, 20th ed., Lippincott Williams & Wilkins: pp. xiv-xv (Table of Contents Only.).

George, J. et al. (1998). "Differential Effects of Anit-$\beta_2$-Glycoprotein I Antibodies on Endothelial Cells and on the Manifestations of Experimental Antiphospholipid Syndrome," *Circulation* 97:900-906.

Glaser, S.M. et al. (Dec. 16, 2005). "Novel Antibody Hinge Regions for Efficient Production of $C_{H2}$ Domain-Deleted Antibodies," *The Journal of Biological Chemistry* 280(50):41494-41503.

Goding, J.W. (1986). *Monoclonal Antibodies: Principles and Practice*, Academic Press Limited: San Diego, CA, 3 pages, (Table of Contents Only.).

Gold, P. et al. (1965). "Specific Carcinoembryonic Antigens of the Human Digestive System," *Journal of Experimental Medicine* 122(3):467-481.

Goldenberg, D. M. (1991) "Imaging and Therapy of Gastrointestinal Cancers with Radiolabeled Antibodies," *American Journal of Gastroenterology* 86(10):1392-1403.

Greenspan, N.S. et al. (Oct. 1999). "Defining Epitopes: It's Not as Easy as it Seems," *Nature Biotechnology* 7:936-937.

Griffiths, A.D. et al. (1993). "Human Anti-Self Antibodies with High Specificity from Phage Display Libraries," *The EMBO Journal* 12(2):725-734.

Hammarström, S. (Apr. 1999). "The Carcinoembryonic Antigen (CEA) Family: Structures, Suggested Functions and Expression in Normal and Malignant tissues," *Seminars in Cancer Biology* 9(2):67-81.

Harlow, E. et al. (1988). *Antibodies, A laboratory Manual*, Cold Spring Harbor Publications: Cold Spring Harbor, NY, pp. iii-ix, (Table of Contents Only.).

Hieter, P. A. et al. (Nov. 1980). "Cloned Human and Mouse Kappa Immunoglobulin Constant and J Region Genes Conserve Homology in Functional Segments," *Cell* 22:197-207.

Holt, L.J. et al. (Nov. 2003). "Domain Antibodies: Proteins for Therapy," *Trends Biotechnology* 21(11):484-490.

Hoogenboom, H.R. et al. (Sep. 1991). "By-Passing Immunisation: Human Antibodies from Synthetic Repertoires of Germline $V_H$ Gene Segments Rearranged in vitro," *Journal of Molecular Biology* 227(2):381-388.

Hsu, T.A. et al. (Apr. 4, 1997). "Differential N-Glycan Patterns of Secreted and Intracellular IgG Produced in Trichoplusia ni Cells," *Journal of Biological Chemistry* 272(14):9062-9070.

Iliades, P. et al. (Jun. 16, 1997). "Triabodies: Single Chain Fv Fragments without a Linker Form Trivalent Trimers," *FEBS Letters* 409(3):437-441.

Imakiire, T. et al. (Feb. 10, 2004). "Generation, Immunologic Characterization and Antitumor Effects of Human Monoclonal Antibodies for Carcinoembryonic Antigen," *International Journal of Cancer* 108(4):564-570.

International Search Report mailed on Mar. 19, 2008, for PCT Application No. PCT/US2007/013587, filed on Jun. 7, 2007, 3 pages.

International Search Report mailed on Jun. 4, 2009, PCT Application No. PCT/US2008/087515, filed on Dec. 18, 2009, 2 pages.

Jefferis, R et al. (1997). "Glycosylation of Antibody Molecules: Structural and Functional Significance," *Chemical Immunology* 65:111-128.

Johnson, K. S. et al. (Aug. 1993). "Human Antibody Engineering," *Current Opinion in Structural Biology* 3(4):564-571.

Jolly, D. (Mar. 1994). "Viral Vector Systems for Gene Therapy," *Cancer Gene Therapy* 1(1):51-64.

Kabat, E.A. et al. (Sep. 1991). *Sequences of Proteins of Immunological Interest*, 5$^{th}$ ed., vol. 2, National Institutes of Health: Bethesda, MD, pp. iii-xi, (Table of Contents Only.).

Kadaja, L. et al. (Apr. 1, 2004). "Over Expression of Leukocyte Marker CD43 Causes Activation of the Tumor Suppressor Proteins p53 and ARF," *Oncogene* 23(14):2523-2530.

Kaplitt, M.G. et al. (Oct. 1994). "Long-Term Gene Expression and Phenotypic Correction Using Adeno-Associated Virus Vectors in the Mammalian Brain," *Nature Genetics* 8:148-154.

Kievit, E. (Dec. 1, 2000). "Yeast Cytosine Deaminase Improves Radiosensitization and Bystander Effect by 5-Fluorocytosine of Human Colorectal Cancer Xenografts," *Cancer Research* 60(23):6649-6655.

Kimura, O. et al. (Jul. 1994). "Retroviral Delivery of DNA into the Livers of Transgenic Mice Bearing Premalignant and Malignant Hepatocellular Carcinomas," *Human Gene Therapy* 5(7):845-852.

Kohler, G. et al. (Aug. 7, 1975). "Continuous Cultures of Fused Cells Secreting Antibody of Predefined Specificity," *Nature* 256(5517):495-497.

Kortt, A.A. et al. (Apr. 1997). "Single-Chain Fv Fragments of Anti-Neuraminidase Antibody NC10 Containing Five- and Ten-Residue Linkers Form Dimers and with Zero-Residue Linker a Trimer," *Protein Engineering* 10(4):423-433.

Kozbor, D. et al. (Dec. 1984). "A Human Hybrid Myeloma for Production of Human Monoclonal Antibodies," *Journal of Immunology* 133(6):3001-3005.

Kuroki, M. et al. (Nov.-Dec. 2000). "Specific Targeting Strategies of Cancer Gene Therapy Using a Single-Chain Variable Fragment (scFv) with a High Affinity for CEA," *Anticancer Research* 20(6A):4067-4072.

Kuroki, M. et al. (Nov.-Dec. 2002). "Significance of Tumor-associated Antigens in the Diagnosis and Therapy of Cancer: An Overview," *Anticancer Research* 22(6C):4255-4264.

Laos, S. et al. (2006). "Inhibition of NF-$_K$B Activation and Chemokine Expression by the Leukocyte Glycoprotein, CD43, in Colon Cancer Cells," *International Journal of Oncology* 28(3):695-704.

Loo, D. et al. (Mar. 2007). "The Glycoptope-Specific RAV12 Monoclonal Antibody Induces Oncosis in vitro and Has Antitumor Activity Against Gastrointestinal Adenocarcinoma Tumor Xenografts in vivo," *Molecular Cancer Therapeutics* 6(3):856-865.

Lopez, S. et al. (Mar. 1998). "CD43 (Sialophorin, Leukosialin) Shedding is an Initial Event During Neutrophil Migration, Which Could Be Closely Related to the Spreading of Adherent Cells," *Cell Adhesion and Communication* 5(2):151-160.

Mahato, R.I. et al. (Jul. 1997). "Cationic Lipid-Based Gene Delivery Systems: Pharmaceutical Perspectives," *Pharmaceutical Research* 14(7):853-859.

Manjunath, N. et al. (Oct. 12, 1995). "Negative Regulation of T-cell Adhesion and Activation by CD43," *Nature* 377(6549):535-538.

Marks, J. D. et al. (Dec. 5, 1991). "By-Passing Immunization: Human Antibodies From V-Gene Libraries Displayed on Phage," *Journal of Molecular Biology* 222(3):581-597.

Marks, J. D. et al. (Jul. 1992). "By-Passing Immunization: Building High Affinity Human Antibodies by Chain Shuffling," *Biotechnology* 10(7):779-783.

Martin, S.J. et al. (Aug. 11, 1995). "Protease Activation During Apoptosis: Death by a Thousand Cuts?" *Cell* 82(3):349-352.

Matsumoto, M. et al. (Dec. 15, 2005). "CD43 Functions as a Ligand for E-Selectin on Activated T Cells," *Journal of Immunology* 175(12):8042-8050.

McCafferty, J. et al. (Dec. 6, 1990). "Phage Antibodies: Filamentous Phage Displaying Antibody Variable Domains," *Nature* 348(6301):552-554.

McEvoy, L.M. et al. (Apr. 21, 1997). "Anti-CD43 Inhibition of T Cell Homing," *Journal of Experimental Medicine* 185(8):1493-1498.

McEvoy, L.M. et al. (Nov. 1, 1997). "Anti-CD43 Inhibits Monocyte-Endothelial Adhesion in Inflammation and Atherogenesis," *Blood* 90(9):3587-3594.

Mentzer, S.J. et al. (May 1, 1987). "Sialophorin, a surface Sialoglycoprotein Defective in the Wiskott-Aldrich Ayndrome, is Involved in Human T Lymphocyte Proliferation," *Journal of Experimental Medicine* 165(5):1383-1392.

Milstein, C. et al. (Oct. 6, 1983). "Hybrid Hybridomas and Their Use in Immunohistochemistry," *Nature* 305(5934):537-540.

Mullis, K.B. et al. ed. (1994). *PCR: The Polymerase Chain Reaction*, Birkhäuser Press: Boston, MA, pp. xv-xvii, (Table of Contents Only.).

Munson, P.J. et al. (Sep. 1, 1980). "LIGAND: A Versatile Computerized Approach for Characterization of Ligand-Binding Systems," *Analytical Biochemistry* 107(1):220-239.

Muyldermans, S. et al. (Jun. 2001). "Single Domain Camel Antibodies: Current Status," *Journal of Biotechnology* 74(4):277-302.

Nieto, M., et al. (1999). "Signaling Through CD43 Induces Natural Killer Cell Activation, Chemokine Release, and PYK-2 Activation," *Blood* 94(8):2767-2777.

Nilsson, O. et al. (Mar. 1985). "Sialosyllactotetraosylceramide, A Novel Ganglioside Antigen Detected in Human Carcinomas by a Monoclonal Antibody," *FEBS* 182(2):398-402.

Nisonoff, A. et al. (Aug. 1960). "Separation of Univalent Fragments From the Bivalent Rabbit Antibody Molecule by Reduction of Disulfide Bonds," *Archives of Biochemistry and Biophysics* 89:230-244.

Nong, Y.H. et al. (Jul. 1, 1989) "A Monoclonal Antibody to Sialophorin (CD43) Induces Homotypic Adhesion and Activation of Human Monocytes," *Journal of Experimental Medicine* 170(1):259-267.

Oi, V.T. et al. (Feb. 1983). "Immunoglobulin Gene Expression in Transformed Lymphoid Cells," *Proceedings of the National Academy of Sciences of the United States of America* 80(3):825-829.

Olafsen, T. et al. (Jan. 2004). "Covalent Disulfide-Linked Anti-CEA Diabody Allows Site-Specific Conjugation and Radiolabeling for Tumor Targeting Applications," *Protein Engineering, Design & Selection* 17(1):21-27.

Pallant, A. et al. (Feb. 1989). "Characterization of cDNAs Encoding Human Leukosialin and Localization of the Leukosialin Gene to Chromosome 16," *Proceedings of the National Academy of Sciences of the United States of America* 86(4):1328-1332.

Park, J.K. et al. (Apr. 25, 1991). "Enhancement of T-cell Activation by the CD43 Molecule Whose Expression is Defective in Wiskott-Aldrich Syndrome," *Nature* 350(6320): 706-709.

Park, W.S. et al. (2004). "Production and the Characterization of Monoclonal Antibody Against CD43, K06," *Tissue Antigens* 63:46-53.

Philip, R. et al. (Apr. 1994). "Efficient and Sustained Gene Expression in Primary T Lymphocytes and Primary and Cultured Tumor Cells Mediated by Adeno-Associated Virus Plasmid DNA Complexed to Cationic Liposomes.," *Molecular and Cellular Biology* 14(4):2411-2418.

Pimenidou, A. et al. (Feb. 2004). "Novel CD43 Specific Phage Antibodies React with Early Stage Colorectal Tumours," *Oncology Reports* 11(2):327-331.

Porter, R.R. (Sep. 1959). "The Hydrolysis of Rabbit γ-globulin and Antibodies with Crystalline Papain," *The Biochemical Journal* 73:119-126.

Remold-O'Donnell, E. et al. (Jun. 1, 1984). "Characterization of a Human Lymphocyte Surface Sialoglycoprotein that is Defective in Wiskott-Aldrich Syndrome," *Journal of Experimental Medicine* 159(6): 1705-1723.

Remold-O'Donnell, E. et al. (Jul. 1987). "Expression on Blood Cells of Sialophorin, the Surface Glycoprotein that is Defective in Wiskott-Aldrich Syndrome," *Blood* 70(1): 104-109.

Rice, D. et al. (Dec. 1982). "Regulated Expression of an Immunoglobulin $_\kappa$-Gene Introduced into a Mouse Lymphoid Cell line," *Proceedings of the National Academy of Sciences of the United States of America* 79(24):7862-7865.

Rousseaux, J. et al. (1986). "Optimal Conditions for the Preparation of Proteolytic Fragments from Monoclonal IgG of Different Rat IgG Subclasses," *Methods in Enzymology* 121:663-669.

Santamaria, M. et al. (Aug. 1, 1996). "Specific Monoclonal Antibodies Against Leukocyte-Restricted Cell Surface Molecule CD43 React with Nonhematopoietic Tumor Cells," *Cancer Research* 56(15):3526-3529.

Schneider, U. et al. (May 15, 1977). "Characterization of EBV-Genome Negative "Null" and "T" Cell Lines Derived from Children with Acute Lymphoblastic Leukemia and Leukemic Transformed Non-Hodgkin Lymphoma," *International Journal of Cancer* 19(5):621-626.

Scovassi, A.I. et al. (Sep. 1999). "Poly(ADP-Ribosylation) and Apoptosis," *Molecular and Cellular Biochemistry* 199(1-2):125-137.

Sheets, M.D. et al. (May 26, 1998). "Efficient Construction of a Large Nonimmune Phage Antibody Library: The Production of High-Affinity Human Single-Chain Antibodies to Protein Antigens," *Proceedings of the National Academy of Sciences of the United States of America* 95(11): 6157-6162.

Sheets, M.D. et al. (1999). "Efficient Construction of a Large Nonimmune Phage Antibody Library: The Production of High-Affinity Human Single-Chain Antibodies to Protein Antigens," *Proceedings of the National Academy of Sciences of the United States of America*, Erratum 96:795.

Shelley, C.S. et al. (Apr. 1989). "Molecular Characterization of Sialophorin (CD43), the Lymphocyte Surface Sialoglycoprotein Defective in Wiskott-Aldrich Syndrome," *Proceedings of the National Academy of Sciences of the United States of America* 86(8):2819-2823.

Shively, J. E. et al. (1985). "CEA-Related Antigens: Molecular Biology and Clinical Significance," *Critical Reviews in Oncology/Hematology* 2(4):355-399.

Sikut, R. et al. (Sep. 18, 1997). "Colon Adenoma and Cancer Cells Aberrantly Express the Leukocyte-Associated Sialoglycoprotein CD43," *Biochemical and Biophysical Research Communications* 238(2):612-616.

Sikut, R. et al. (Jul. 2, 1999). "Detection of CD43 (leukosialin) in Colon Adenoma and Adenocarcinoma by Novel Monoclonal Antibodies Against its Intracellular Domain," *International Journal of Cancer* 82(1):52-58.

Smyth, D.G., (1967). "Use of Papain, Pepsin, and Subtilisin in Sequence Determination," *Methods in Enzymology* 11:421-426.

Stockton, B.M. et al. (Mar. 1998). "Negative Regulation of T Cell Homing by CD43," *Immunity* 8(3):373-381.

Suresh, M.R. et al. (1986). "Bispecific Monoclonal Antibodies from Hybrid Hybridomas," *Methods in Enzymology* 121:210-228.

Thompson, J.A. et al. (May 1987). "Molecular Cloning of a Gene Belonging to the Carcinoembryonic Antigen Gene Family and Discussion of a Domain Model," *Proc. Natl. Acad. Sci. USA* 84(9):2965-2969.

Thornberry, N.A. et al. (Aug. 28, 1998). "Caspases: Enemies Within," *Science* 281(5381):1312-1316.

Toneguzzo, F. et al. (Feb. 1986). "Electric Field-Mediated DNA Transfer: Transient and Stable Gene Expression in Human and Mouse Lymphoid Cells.," *Molecular and Cellular Biology* 6(2):703-706.

Treasure, J. et al. (Nov. 1992). "CD43 Expression in B Cell Lymphoma," *Journal of Clinical Pathology* 45(11):1018-1022.

Umaña, P. et al. (Feb. 1999). "Engineered Glycoforms of an Antineuroblastoma IgG1 with Optimized Antibody-Dependent Cellular Cytotoxic Activity," *Nature Biotechnology* 17(2):176-180.

Vaughan, T.J. et al. (Mar. 1996). "Human Antibodies with Sub-Nanomolar Affinities Isolated from a Large Non-Immunized Phage Display Library," *Nature Biotechnology* 14(3):309-314.

Waterhouse, P. et al. (May 11, 1993). "Combinatorial Infection and *in vivo* Recombination: a Strategy for Making Large Phage Antibody Repertoires," *Nucleic Acids Research* 21(9):2265-2266.

Wilkinson, R. W. et al. (Aug. 28, 2001). "Antibody Targeting Studies in a Transgenic Murine Model of Spontaneous Colorectal Tumors," *Proceedings of the National Academy of Sciences of the United States of America* 98(18)10256-10260.

Winter, G. et al. (1994). "Making Antibodies by Phage Display Technology," *Annual Review of Immunology* 12:433-455.

Wittwer, A.J. et al. (May 1, 1990). "Glycosylation at Asn-184 Inhibits the Conversion of Single-Chain to Two-Chain Tissue-Type Plasminogen Activator by Plasmin," *Biochemistry* 29(17):4175-4180.

Woffendin, C. et al. (Nov. 22, 1994). "Nonviral and Viral delivery of a Human Immunodeficiency Virus Protective Gene into Primary Human T Cells," *Proceedings of the National Academy of Science of the United States of America* 91(24):1581-1585.

Wright, A. et al. (Jan. 1997). "Effect of Glycosylation on Antibody Function: Implications for Genetic Engineering," *Trends in Biotechnology* 15(1):26-32.

Wu, C.H. et al. (Oct. 15, 1989). "Targeting Genes: Delivery and Persistent Expression of a Foreign Gene Driven by Mammalian Regulatory Elements in Vivo," *Journal of Biological Chemistry* 264(29):16985-16987.

Wu, G.Y. et al. (Oct. 15, 1988). "Receptor-Mediated Gene Delivery and Expression in Vivo," *Journal of Biological Chemistry* 263(29):14621-14624.

Wu, G.Y. et al. (Aug. 5, 1991). "Receptor-Mediated Gene Delivery in Vivo Partial Correction of Genetic Analbuminemia in Nagase Rats.," *Journal of Biological Chemistry* 266(22):14338-14342.

Wu, G.Y. et al. (Apr. 15, 1994). "Incorporation of Adenovirus into a Ligand-Based DNA Carrier System Results in Retention of Original Receptor Specificity and Enhances Targeted Gene Expression," *Journal of Biological Chemistry* 269(15):11542-11546.

Wyllie, A.H. et al. (1980). "Cell Death: the Significance of Apoptosis," *International Review of Cytology* 68:251-306.

Wyss, D.F. et al. (Aug. 1996). "The Structural Role of Sugars in Glycoproteins," *Current Opinion in Biotechnology* 7(4):409-416.

Ychou, M. (Feb. 9, 1998). "Phase I/II Radio-Immunotherapy Study with Iodine-131-Labeled Anti-CEA Monoclonal Antibody $F^A$ $F(ab')_2$ in Patients with Non-Resectable Liver Metastases From Colorectal Cancer," *International Journal of Cancer* 75(4):615-619.

Zenke, M. et al. (May 1990). "Receptor-Mediated Endocytosis of Transferrin-Polycation Conjugates: An Efficient Way to Introduce DNA into Hematopoietic Cells," *Proceedings of the National Academy of Science of the United States of America* 87(10):3655-3659.

Zola, H. et al. (1987). "Using Monoclonal Antibodies: Soluble Antigens," Chapter 6, *in Monoclonal Antibodies: A Manual of Techniques*, CRC Press Inc., Boca Raton, FL, pp. 147-181.

Amendment in Response to Non-Final Office Action submitted on Jun. 23, 2009, for U.S. Appl. No. 11/811,303, filed Jun. 7, 2007, 33 pages.

Non-Final Office Action mailed on Dec. 23, 2008, for U.S. Appl. No. 11/811,303, filed Jun. 7, 2007, 41 pages.

Notice of Allowance mailed on Nov. 2, 2009, for U.S. Appl. No. 11/811,303, filed Jun. 7, 2007, 7 pages.

* cited by examiner

FIG. 1

```
HuIgG1_CR   ASTKGPSVFPLAPSSKSTSGGTAALGCLVKDYFPEPVTVSWNSGALTSGVHTFPAVLQSS 60
MuIgG3      ATTTAPSVYPLVPGCSDTSGSSVTLGCLVKGYFPEPVTVKWNYGALSSGVRTVSSVLQS- 59
            *:*..***:**.*....***.:.:*****.********.**.***:***:*...:****

HuIgG1_CR   GLYSLSSVVTVPSSSLGTQTYICNVNHKPSNTKVDKKVEPKSCDKTHTCP--PCPAPELL 118
MuIgG3      GFYSLSSLVTVPSSTWPSQTVICNVAHPASKTELIKRIEPR-IPKPSTPPGSSCPPGNIL 118
            *:*****:******:  :** **** * .*:*::  *::**:   *. * .**. ::*

HuIgG1_CR   GGPSVFLFPPKPKDTLMISRTPEVTCVVVDVSHEDPEVKFNWYVDGVEVHNAKTKPREEQ 178
MuIgG3      GGPSVFIFPPKPKDALMISLTPKVTCVVVDVSEDDPDVHVSWFVDNKEVHTAWTQPREAQ 178
            ******:*******.**** **:*********.:**:*:...*:**. ***.* *:*** *

HuIgG1_CR   YNSTYRVVSVLTVLHQDWLNGKEYKCKVSNKALPAPIEKTISKAKGQPREPQVYTLPPSR 238
MuIgG3      YNSTFRVVSALPIQHQDWMRGKEFKCKVNNKALPAPIERTISKPKGRAQTPQVYTIPPPR 238
            ****:****.*.*: ****:.***:****.*********:****.**...:.*****:**.*

HuIgG1_CR   DELTKNQVSLTCLVKGFYPSDIAVEWESNGQPENNYKTTPPVLDSDGSFFLYSKLTVDKS 298
MuIgG3      EQMSKKKVSLTCLVTNFFSEAISVEWERNGELEQDYKNTPPILDSDGTYFLYSKLTVDTD 298
            ::::*::*******..*:...*:****.**:.*::**.***:*****::*********..

HuIgG1_CR   RWQQGNVFSCSVMHEALHNHYTQKSLSLSPGK 330
MuIgG3      SWLQGEIFTCSVVHEALHNHHTQKNLSRSPGK 330
            .*.**::*:***:*******:***:**.****
```

FIG. 2A

Sequence Listing

```
                              CH1
V0[H] (SEQ ID NO:9)  ASTKGPSVFPLAPSSKSTSGGTAALGCLVKDYFPEPVTVSWNSGALTSGVHTFPAVLQSS 60
V1    (SEQ ID NO:11) ASTKGPSVFPLAPSSKSTSGGTAALGCLVKDYFPEPVTVSWNSGALTSGVHTFPAVLQSS 60
V2    (SEQ ID NO:12) ASTKGPSVFPLAPCSKSTSGGTAALGCLVKDYFPEPVTVSWNSGALTSGVHTFPAVLQSS 60
V3    (SEQ ID NO:13) ASTKGPSVFPLVPGCSDTSGGTAALGCLVKDYFPEPVTVSWNSGALTSGVHTFPAVLQSS 60
V4    (SEQ ID NO:14) ASTKGPSVFPLAPGCSDTSGGTAALGCLVKDYFPEPVTVSWNSGALTSGVHTFPAVLQSS 60
V5    (SEQ ID NO:15) ASTKGPSVFPLAPCSKSTSGGTAALGCLVKDYFPEPVTVSWNSGALTSGVHTFPAVLQSS 60
V6    (SEQ ID NO:16) ASTKGPSVFPLAPCSRSTSGGTAALGCLVKDYFPEPVTVSWNSGALTSGVHTFPAVLQSS 60
V7    (SEQ ID NO:17) ASTKGPSVFPLAPCSKSTSGGTAALGCLVKDYFPEPVTVSWNSGALTSGVHTFPAVLQSS 60
V8    (SEQ ID NO:18) ASTKGPSVFPLAPCSRSTSGGTAALGCLVKDYFPEPVTVSWNSGALTSGVHTFPAVLQSS 60
V9    (SEQ ID NO:19) ASTKGPSVFPLAPCSRSTSGGTAALGCLVKDYFPEPVTVSWNSGALTSGVHTFPAVLQSS 60
V10   (SEQ ID NO:20) ASTKGPSVFPLAPCSRSTSGGTAALGCLVKDYFPEPVTVSWNSGALTSGVHTFPAVLQSS 60
V11   (SEQ ID NO:21) ASTKGPSVFPLVPGCSDTSGGTAALGCLVKDYFPEPVTVSWNSGALTSGVHTFPAVLQSS 60
V12   (SEQ ID NO:22) ASTKGPSVFPLAPGCSDTSGGTAALGCLVKDYFPEPVTVSWNSGALTSGVHTFPAVLQSS 60
V13   (SEQ ID NO:23) ASTKGPSVFPLAPCSKSTSGGTAALGCLVKDYFPEPVTVSWNSGALTSGVHTFPAVLQSS 60
V14   (SEQ ID NO:24) ASTKGPSVFPLAPCSRSTSGGTAALGCLVKDYFPEPVTVSWNSGALTSGVHTFPAVLQSS 60
V15   (SEQ ID NO:25) ASTKGPSVFPLAPSSKSTSGGTAALGCLVKDYFPEPVTVSWNSGALTSGVHTFPAVLQSS 60
V16   (SEQ ID NO:26) ASTKGPSVFPLAPSSKSTSGGTAALGCLVKDYFPEPVTVSWNSGALTSGVHTFPAVLQSS 60
V17   (SEQ ID NO:27) ASTKGPSVFPLAPSSKSTSGGTAALGCLVKDYFPEPVTVSWNSGALTSGVHTFPAVLQSS 60
V18   (SEQ ID NO:28) ASTKGPSVFPLAPSSKSTSGGTAALGCLVKDYFPEPVTVSWNSGALTSGVHTFPAVLQSS 60
V19   (SEQ ID NO:29) ASTKGPSVFPLAPSSKSTSGGTAALGCLVKDYFPEPVTVSWNSGALTSGVHTFPAVLQSS 60
V20   (SEQ ID NO:30) ASTKGPSVFPLAPSSKSTSGGTAALGCLVKDYFPEPVTVSWNSGALTSGVHTFPAVLQSS 60
                    **********: .*:**:*****************************************

Hinge
V0[H] GLYSLSSVVTVPSSSLGTQTYICNVNHKPSNTKVDKKV EPKS---CDKTHTCPPCP APEL 117
V1    GLYSLSSVVTVPSSSLGTQTYICNVNHKPSNTKVDKKV EPKS---SDKTHTCPPCP APEL 117
V2    GLYSLSSVVTVPSSSLGTQTYICNVNHKPSNTKVDKKV EPKS---SDKTHTCPPCP APEL 117
V3    GLYSLSSVVTVPSSSLGTQTYICNVNHKPSNTKVDKKV EPKS---SDKTHTCPPCP APEL 117
V4    GLYSLSSVVTVPSSSLGTQTYICNVNHKPSNTKVDKKV EPKS---SDKTHTCPPCP APEL 117
```

FIG. 2B

```
V5   GLYSLSSVVTVPSSSLGTQTYICNVNHKPSNTKVDKKV EPKS---SDKTHTGPPCP APEL 117
V6   GLYSLSSVVTVPSSSLGTQTYICNVNHKPSNTKVDKKV EPKS---SDKTHTGPPCP APEL 117
V7   GLYSLSSVVTVPSSSLGTQTYICNVNHKPSNTKVDKKV EPKS---SDKTHTGSSCP APEL 117
V8   GLYSLSSVVTVPSSSLGTQTYICNVNHKPSNTKVDKKV EPKS---SDKTHTGSSCP APEL 117
V9   GLYSLSSVVTVPSSSLGTQTYICNVNHKPSNTKVDKKV EPKS--SD-KTPPGSSCP APEL 117
V10  GLYSLSSVVTVPSSSLGTQTYICNVNHKPSNTKVDKKV EPKS--SD-KTPPGSSCP APEL 117
V11  GLYSLSSVVTVPSSSLGTQTYICNVNHKPSNTKVDKKV EPKS--SD-KTPPGSSCP APEL 117
V12  GLYSLSSVVTVPSSSLGTQTYICNVNHKPSNTKVDKKV EPKS--SD-KTPPGSSCP APEL 117
V13  GLYSLSSVVTVPSSSLGTQTYICNVNHKPSNTKVDKKV EPKS--SD-KTPPGSSCP APEL 117
V14  GLYSLSSVVTVPSSSLGTQTYICNVNHKPSNTKVDKKV EPRI--PKPSTPPGSSCP APEL 118
V15  GLYSLSSVVTVPSSSLGTQTYICNVNHKPSNTKVDKKV EPRI--PKPSTPPGSSCP APEL 118
V16  GLYSLSSVVTVPSSSLGTQTYICNVNHKPSNTKVDKKV EPK----SDKTHTCPPCP APEL 116
V17  GLYSLSSVVTVPSSSLGTQTYICNVNHKPSNTKVDKKV EPKS---SDKTHTCPPCP APEL 117
V18  GLYSLSSVVTVPSSSLGTQTYICNVNHKPSNTKVDKKV EPKS--SCDKTHTCPPCP APEL 118
V19  GLYSLSSVVTVPSSSLGTQTYICNVNHKPSNTKVDKKV EPKC---SDKTHTCPPCP APEL 117
V20  GLYSLSSVVTVPSSSLGTQTYICNVNHKPSNTKVDKKV EPKSDKSCDKTHTCPPCP APEL 120
     ****************************************    *  .*. ****
                                                    CH2
V0[H] LGGPSVFLFPPKPKDTLMISRTPEVTCVVVDVSHEDPEVKFNWYVDGVEVHNAKTKPREE 177
V1   LGGPSVFLFPPKPKDTLMISRTPEVTCVVVDVSHEDPEVKFNWYVDGVEVHNAKTKPREE 177
V2   LGGPSVFLFPPKPKDTLMISRTPEVTCVVVDVSHEDPEVKFNWYVDGVEVHNAKTKPREE 177
V3   LGGPSVFLFPPKPKDTLMISRTPEVTCVVVDVSHEDPEVKFNWYVDGVEVHNAKTKPREE 177
V4   LGGPSVFLFPPKPKDTLMISRTPEVTCVVVDVSHEDPEVKFNWYVDGVEVHNAKTKPREE 177
V5   LGGPSVFLFPPKPKDTLMISRTPEVTCVVVDVSHEDPEVKFNWYVDGVEVHNAKTKPREE 177
V6   LGGPSVFLFPPKPKDTLMISRTPEVTCVVVDVSHEDPEVKFNWYVDGVEVHNAKTKPREE 177
V7   LGGPSVFLFPPKPKDTLMISRTPEVTCVVVDVSHEDPEVKFNWYVDGVEVHNAKTKPREE 177
V8   LGGPSVFLFPPKPKDTLMISRTPEVTCVVVDVSHEDPEVKFNWYVDGVEVHNAKTKPREE 177
V9   LGGPSVFLFPPKPKDTLMISRTPEVTCVVVDVSHEDPEVKFNWYVDGVEVHNAKTKPREE 177
V10  LGGPSVFLFPPKPKDTLMISRTPEVTCVVVDVSHEDPEVKFNWYVDGVEVHNAKTKPREE 177
V11  LGGPSVFLFPPKPKDTLMISRTPEVTCVVVDVSHEDPEVKFNWYVDGVEVHNAKTKPREE 177
```

FIG. 2C

```
V12 LGGPSVFLFPPKPKDTLMISRTPEVTCVVVDVSHEDPEVKFNWYVDGVEVHNAKTKPREE 177
V13 LGGPSVFLFPPKPKDTLMISRTPEVTCVVVDVSHEDPEVKFNWYVDGVEVHNAKTKPREE 178
V14 LGGPSVFLFPPKPKDTLMISRTPEVTCVVVDVSHEDPEVKFNWYVDGVEVHNAKTKPREE 178
V15 LGGPSVFLFPPKPKDTLMISRTPEVTCVVVDVSHEDPEVKFNWYVDGVEVHNAKTKPREE 176
V16 LGGPSVFLFPPKPKDTLMISRTPEVTCVVVDVSHEDPEVKFNWYVDGVEVHNAKTKPREE 177
V17 LGGPSVFLFPPKPKDTLMISRTPEVTCVVVDVSHEDPEVKFNWYVDGVEVHNAKTKPREE 178
V18 LGGPSVFLFPPKPKDTLMISRTPEVTCVVVDVSHEDPEVKFNWYVDGVEVHNAKTKPREE 177
V19 LGGPSVFLFPPKPKDTLMISRTPEVTCVVVDVSHEDPEVKFNWYVDGVEVHNAKTKPREE 180
V20 LGGPSVFLFPPKPKDTLMISRTPEVTCVVVDVSHEDPEVKFNWYVDGVEVHNAKTKPREE 180
    ************************************************************
                                 CH2                                          CH3
V0[H] QYNSTYRVVSVLTVLHQDWLNGKEYKCKVSNKALPAPIEKTISKAK GQPREPQVYTLPPS 237
V1    QYNSTYRVVSVLTVLHQDWLNGKEYKCKVSNKALPAPIEKTISKAK GQPREPQVYTLPPS 237
V2    QYNSTYRVVSVLTVLHQDWLNGKEYKCKVSNKALPAPIEKTISKAK GQPREPQVYTLPPS 237
V3    QYNSTYRVVSVLTVLHQDWLNGKEYKCKVSNKALPAPIEKTISKAK GQPREPQVYTLPPS 237
V4    QYNSTYRVVSVLTVLHQDWLNGKEYKCKVSNKALPAPIEKTISKAK GQPREPQVYTLPPS 237
V5    QYNSTYRVVSVLTVLHQDWLNGKEYKCKVSNKALPAPIEKTISKAK GQPREPQVYTLPPS 237
V6    QYNSTYRVVSVLTVLHQDWLNGKEYKCKVSNKALPAPIEKTISKAK GQPREPQVYTLPPS 237
V7    QYNSTYRVVSVLTVLHQDWLNGKEYKCKVSNKALPAPIEKTISKAK GQPREPQVYTLPPS 237
V8    QYNSTYRVVSVLTVLHQDWLNGKEYKCKVSNKALPAPIEKTISKAK GQPREPQVYTLPPS 237
V9    QYNSTYRVVSVLTVLHQDWLNGKEYKCKVSNKALPAPIEKTISKAK GQPREPQVYTLPPS 237
V10   QYNSTYRVVSVLTVLHQDWLNGKEYKCKVSNKALPAPIEKTISKAK GQPREPQVYTLPPS 237
V11   QYNSTYRVVSVLTVLHQDWLNGKEYKCKVSNKALPAPIEKTISKAK GQPREPQVYTLPPS 237
V12   QYNSTYRVVSVLTVLHQDWLNGKEYKCKVSNKALPAPIEKTISKAK GQPREPQVYTLPPS 237
V13   QYNSTYRVVSVLTVLHQDWLNGKEYKCKVSNKALPAPIEKTISKAK GQPREPQVYTLPPS 238
V14   QYNSTYRVVSVLTVLHQDWLNGKEYKCKVSNKALPAPIEKTISKAK GQPREPQVYTLPPS 238
V15   QYNSTYRVVSVLTVLHQDWLNGKEYKCKVSNKALPAPIEKTISKAK GQPREPQVYTLPPS 236
V16   QYNSTYRVVSVLTVLHQDWLNGKEYKCKVSNKALPAPIEKTISKAK GQPREPQVYTLPPS 237
V17   QYNSTYRVVSVLTVLHQDWLNGKEYKCKVSNKALPAPIEKTISKAK GQPREPQVYTLPPS 238
V18   QYNSTYRVVSVLTVLHQDWLNGKEYKCKVSNKALPAPIEKTISKAK GQPREPQVYTLPPS 237
```

FIG. 2D

```
V19   QYNSTYRVVSVLTVLHQDWLNGKEYKCKVSNKALPAPIEKTISKAK GQPREPQVYTLPPS  240
V20   QYNSTYRVVSVLTVLHQDWLNGKEYKCKVSNKALPAPIEKTISKAK GQPREPQVYTLPPS  240
      *********************************************  **************
```

```
                                          CH3
V0[H]  RDELTKNQVSLTCLVKGFYPSDIAVEWESNGQPENNYKTTPPVLDSDGSFFLYSKLTVDK  297
V1     RDELTKNQVSLTCLVKGFYPSDIAVEWESNGQPENNYKTTPPVLDSDGSFFLYSKLTVDK  297
V2     RDELTKNQVSLTCLVKGFYPSDIAVEWESNGQPENNYKTTPPVLDSDGSFFLYSKLTVDK  297
V3     RDELTKNQVSLTCLVKGFYPSDIAVEWESNGQPENNYKTTPPVLDSDGSFFLYSKLTVDK  297
V4     RDELTKNQVSLTCLVKGFYPSDIAVEWESNGQPENNYKTTPPVLDSDGSFFLYSKLTVDK  297
V5     RDELTKNQVSLTCLVKGFYPSDIAVEWESNGQPENNYKTTPPVLDSDGSFFLYSKLTVDK  297
V6     RDELTKNQVSLTCLVKGFYPSDIAVEWESNGQPENNYKTTPPVLDSDGSFFLYSKLTVDK  297
V7     RDELTKNQVSLTCLVKGFYPSDIAVEWESNGQPENNYKTTPPVLDSDGSFFLYSKLTVDK  297
V8     RDELTKNQVSLTCLVKGFYPSDIAVEWESNGQPENNYKTTPPVLDSDGSFFLYSKLTVDK  297
V9     RDELTKNQVSLTCLVKGFYPSDIAVEWESNGQPENNYKTTPPVLDSDGSFFLYSKLTVDK  297
V10    RDELTKNQVSLTCLVKGFYPSDIAVEWESNGQPENNYKTTPPVLDSDGSFFLYSKLTVDK  297
V11    RDELTKNQVSLTCLVKGFYPSDIAVEWESNGQPENNYKTTPPVLDSDGSFFLYSKLTVDK  297
V12    RDELTKNQVSLTCLVKGFYPSDIAVEWESNGQPENNYKTTPPVLDSDGSFFLYSKLTVDK  297
V13    RDELTKNQVSLTCLVKGFYPSDIAVEWESNGQPENNYKTTPPVLDSDGSFFLYSKLTVDK  298
V14    RDELTKNQVSLTCLVKGFYPSDIAVEWESNGQPENNYKTTPPVLDSDGSFFLYSKLTVDK  298
V15    RDELTKNQVSLTCLVKGFYPSDIAVEWESNGQPENNYKTTPPVLDSDGSFFLYSKLTVDK  296
V16    RDELTKNQVSLTCLVKGFYPSDIAVEWESNGQPENNYKTTPPVLDSDGSFFLYSKLTVDK  297
V17    RDELTKNQVSLTCLVKGFYPSDIAVEWESNGQPENNYKTTPPVLDSDGSFFLYSKLTVDK  298
V18    RDELTKNQVSLTCLVKGFYPSDIAVEWESNGQPENNYKTTPPVLDSDGSFFLYSKLTVDK  297
V19    RDELTKNQVSLTCLVKGFYPSDIAVEWESNGQPENNYKTTPPVLDSDGSFFLYSKLTVDK  300
V20    RDELTKNQVSLTCLVKGFYPSDIAVEWESNGQPENNYKTTPPVLDSDGSFFLYSKLTVDK  300
       ************************************************************
```

FIG. 2E

| | CH3 | |
|---|---|---|
| V0 [H] | SRWQQGNVFSCSVMHEALHNHYTQKSLSLSLSPGK | 330 |
| V1 | SRWQQGNVFSCSVMHEALHNHYTQKSLSLSLSPGK | 330 |
| V2 | SRWQQGNVFSCSVMHEALHNHYTQKSLSLSLSPGK | 330 |
| V3 | SRWQQGNVFSCSVMHEALHNHYTQKSLSLSLSPGK | 330 |
| V4 | SRWQQGNVFSCSVMHEALHNHYTQKSLSLSLSPGK | 330 |
| V5 | SRWQQGNVFSCSVMHEALHNHYTQKSLSLSLSPGK | 330 |
| V6 | SRWQQGNVFSCSVMHEALHNHYTQKSLSLSLSPGK | 330 |
| V7 | SRWQQGNVFSCSVMHEALHNHYTQKSLSLSLSPGK | 330 |
| V8 | SRWQQGNVFSCSVMHEALHNHYTQKSLSLSLSPGK | 330 |
| V9 | SRWQQGNVFSCSVMHEALHNHYTQKSLSLSLSPGK | 330 |
| V10 | SRWQQGNVFSCSVMHEALHNHYTQKSLSLSLSPGK | 330 |
| V11 | SRWQQGNVFSCSVMHEALHNHYTQKSLSLSLSPGK | 331 |
| V12 | SRWQQGNVFSCSVMHEALHNHYTQKSLSLSLSPGK | 331 |
| V13 | SRWQQGNVFSCSVMHEALHNHYTQKSLSLSLSPGK | 331 |
| V14 | SRWQQGNVFSCSVMHEALHNHYTQKSLSLSLSPGK | 331 |
| V15 | SRWQQGNVFSCSVMHEALHNHYTQKSLSLSLSPGK | 329 |
| V16 | SRWQQGNVFSCSVMHEALHNHYTQKSLSLSLSPGK | 330 |
| V17 | SRWQQGNVFSCSVMHEALHNHYTQKSLSLSLSPGK | 331 |
| V18 | SRWQQGNVFSCSVMHEALHNHYTQKSLSLSLSPGK | 330 |
| V19 | SRWQQGNVFSCSVMHEALHNHYTQKSLSLSLSPGK | 333 |
| V20 | SRWQQGNVFSCSVMHEALHNHYTQKSLSLSLSPGK | 333 |
| | ********************************** | |

FIG. 2F

```
Kappa seq (V19+Modified LC)
V0[L]  (SEQ ID NO:10)  RTVAAPSVFIFPPSDEQLKSGTASVVCLLNNFYPREAKVQWKVDNALQSGNSQESVTEQD  60
V21    (SEQ ID NO:31)  RTVAAPSVFIFPPSDEQLKSGTASVVCLLNNFYPREAKVQWKVDNALQSGNSQESVTEQD  60
V22    (SEQ ID NO:32)  RTVAAPSVFIFPPSDEQLKSGTASVVCLLNNFYPREAKVQWKVDNALQSGNSQESVTEQD  60
V23    (SEQ ID NO:33)  RTVAAPSVFIFPPSDEQLKSGTASVVCLLNNFYPREAKVQWKVDNALQSGNSQESVTEQD  60
V24    (SEQ ID NO:34)  RTVAAPSVFIFPPSDEQLKSGTASVVCLLNNFYPREAKVQWKVDNALQSGNSQESVTEQD  60
V25    (SEQ ID NO:35)  RTVAAPSVFIFPPSDEQLKSGTASVVCLLNNFYPREAKVQWKVDNALQSGNSQESVTEQD  60
V26    (SEQ ID NO:36)  RTVAAPSVFIFPPSDEQLKSGTASVVCLLNNFYPREAKVQWKVDNALQSGNSQESVTEQD  60
V27    (SEQ ID NO:37)  RTVAAPSVFIFPPSDEQLKSGTASVVCLLNNFYPREAKVQWKVDNALQSGNSQESVTEQD  60
                      ************************************************************

V0[L]  SKDSTYSLSSTLTLSKADYEKHKVYACEVTHQGLSSPVTKSFNRG-----EC   107
V21    SKDSTYSLSSTLTLSKADYEKHKVYACEVTHQGLSSPVTKSFNRGG---EGEC   109
V22    SKDSTYSLSSTLTLSKADYEKHKVYACEVTHQGLSSPVTKSFNRGG--EGEC    110
V23    SKDSTYSLSSTLTLSKADYEKHKVYACEVTHQGLSSPVTKSFNRGG-EGEC     111
V24    SKDSTYSLSSTLTLSKADYEKHKVYACEVTHQGLSSPVTKSFNRGG---EC     108
V25    SKDSTYSLSSTLTLSKADYEKHKVYACEVTHQGLSSPVTKSFNRGGGEGEC     109
V26    SKDSTYSLSSTLTLSKADYEKHKVYACEVTHQGLSSPVTKSFNRGGGG-EC     109
V27    SKDSTYSLSSTLTLSKADYEKHKVYACEVTHQGLSSPVTKSFNRGGGGGEC     109
       *********************************************    **
```

Binding of variant 5F1 antibodies to COLO 205

FIG. 4A

The list of the modified humanized 5F1 antibodies. The amino acid of $V_H$ (a) and $V_L$ (b) of h5F1M, h5F1M Va, h5F1M Vs, h5F1A Va and h5F1A Vs, are aligned for comparison.

(a)

```
                                                          Fw1                              CDR1
h5F1M   _HC SEQ ID NO:87  QVQLVQSGAEVKKPGSSVKVSCKASGYTFT  SYVMH  WVRQAP
h5F1MVa_HC SEQ ID NO:88  QVQLVQSGAEVKKPGSSVKVSCKASGYTFT  SYVMH  WVRQAP
h5F1MVs_HC SEQ ID NO:89  QVQLVQSGAEVKKPGSSVKVSCKASGYTFT  SYVMH  WVRQAP
h5F1AVa_HC SEQ ID NO:90  QVQLVQSGAEVKKPGASVKVSCKASGYTFT  SYVMH  WVRQAP
h5F1AVs_HC SEQ ID NO:91  QVQLVQSGAEVKKPGASVKVSCKASGYTFT  SYVMH  WVRQAP
                          **************** ************* *****  ******

Fw2                CDR2                              Fw3
h5F1M   _HC  GQGLEWIG  YINPYNGGTQYNEKFKG  KATITADESTNTAYMELSSLRSEDTAVYYCAR  RTF
h5F1MVa_HC  GQGLEWIG  YINPYNGGTQYNEKFKG  KATITADESTNTAYMELSSLTSEDSAVYYCAR  RTF
h5F1MVs_HC  GQGLEWIG  YINPYNGGTQYNEKFKG  KATITADISTNTAYMELSSLTSEDSAVYYCAR  RTF
h5F1AVa_HC  GQRLEWMG  YINPYNGGTQYNEKFKG  RVTITSDTSASTAYMELSSLTSEDSAVYYCAR  RTF
h5F1AVs_HC  GQRLEWMG  YINPYNGGTQYNEKFKG  RVTITSDISSSTAYMELSSLTSEDSAVYYCAR  RTF
             ** ****:  *****************  :.****:*  *:.:.*********.*******  ***

CDR3     Fw4
h5F1M   _HC  PYYFDY  WGQGTLVTVSS
h5F1MVa_HC  PYYFDY  WGQGTLVTVSS
h5F1MVs_HC  PYYFDY  WGQGTLVTVSS
h5F1AVa_HC  PYYFDY  WGQGTLVTVSS
h5F1AVs_HC  PYYFDY  WGQGTLVTVSS
             ******  ***********
```

FIG. 4B (b)

```
                              Fw1                          CDR1
h5F1M   _LC  SEQ ID NO:92  DIQMTQSPSSLSASVGDRVTITC  RSSQSILHSNGNTYLE W
h5F1MVa_LC  SEQ ID NO:93  DIQMTQSPSSLSASVGDRVTITC  RSSQSILHSNGNTYLE W
h5F1MVs_LC  SEQ ID NO:94  DIQMTQSPSSLSASVGDRVTITC  RSSQSILHSNGNTYLE W
h5F1AVa_LC  SEQ ID NO:95  DIQMTQSPSSLSASVGDRVTITC  RSSQSILHSNGNTYLE W
h5F1AVs_LC  SEQ ID NO:96  DIQMTQSPSSLSASVGDRVTITC  RSSQSILHSNGNTYLE W
                          ***********************  **************** *

Fw2              CDR2                     Fw3                              CDR3
h5F1M   _LC   YQQKPGKAPKLLIY   KVSNRFS   GVPSRFSGSGSGSGTDFTLTISSLQPDDFATYYC   FQGSHAP
h5F1MVa_LC   YQQKPGKAPKLLIY   KVSNRFS   GVPSRFSGSGSGSGTDFTLTISSLQPDDFATYYC   FQGSHAP
h5F1MVs_LC   YQQKPGKAPKLLIY   KVSNRFS   GVPSRFSGSGSGSGTDFTLKISRVEAEDLGTYYC   FQGSHAP
h5F1AVa_LC   YQQKPGKAPKLLIY   KVSNRFS   GVPSRFSGSGSGSGTDFTFTISSLQPEDIATYYC   FQGSHAP
h5F1AVs_LC   YQQKPGKAPKLLIY   KVSNRFS   GVPSRFSGSGSGSGTDFTLKISRVEAEDLGTYYC   FQGSHAP
             **************   *******   *****************  :  ::.:.:   .*    *******

Fw4
h5F1M   _LC   LT FGQGTKVELK
h5F1MVa_LC   LT FGQGTKVELK
h5F1MVs_LC   LT FGQGTKVELK
h5F1AVa_LC   LT FGQGTKVEIK
h5F1AVs_LC   LT FGQGTKVEIK
             ** **********:*
```

ANTIBODIES RECOGNIZING A CARBOHYDRATE CONTAINING EPITOPE ON CD-43 AND CEA EXPRESSED ON CANCER CELLS AND METHODS USING SAME

CROSS-REFERENCE TO RELATED APPLICATIONS

This application claims the priority benefit of U.S. provisional application Ser. No. 61/014,716, filed Dec. 18, 2007, which is incorporated herein by reference in its entirety.

FIELD OF THE INVENTION

The present invention relates to antibodies (e.g., chimeric and humanized antibodies) that recognize a carbohydrate containing epitope on CD43 and carcinoembryonic antigen (CEA) expressed on nonhematopoietic tumor or cancer cells. These antibodies have the property of inducing cell death (e.g., apoptosis) in these nonhematopoietic tumor or cancer cells in the absence of cytotoxin conjugation and immune effector function. These antibodies are useful as diagnostic and therapeutic agents.

BACKGROUND OF THE INVENTION

CD43 (also named as sialophorin or leukosialin), a heavily sialylated molecule expresses at high levels on most human leukocytes including all T cells and platelets with a molecular weight ranging from 115,000 to 135,000. CD43 expression is defective on the T cells of males with the Wiskott-Aldrich syndrome, an X chromosome-linked recessive immunodeficiency disorder (Remold-O'Donnell et al. (1987) *Blood* 70(1):104-9; Remold-O'Donnel et al. (1984) *J. Exp. Med.* 159:1705-23).

Functional studies demonstrated that anti-CD43 monoclonal antibody stimulates the proliferation of peripheral blood T lymphocytes (Mentzer et al. (1987) *J. Exp. Med.* 1; 165 (5):1383-92; Park et al. (1991) *Nature,* 350:706-9) and the activation of monocytes (Nong et al. (1989) *J. Exp. Med.* 1:170(1):259-67). A monoclonal anti-CD43 antibody L11 blocks T cell binding to lymph node and Peyer's patch HEV. Antibody L11 inhibits T cell extravasation from the blood into organized secondary lymphoid tissues (McEvoy et al. (1997) *J. Exp. Med.* 185:1493-8). Monoclonal antibody recognizing CD43 molecule induces apoptosis of lineage marker-negative bone marrow hematopoietic progenitor cells (HPCs) that express CD34 at a high density (Bazil et al. (1996) *Blood,* 87(4):1272-81.) and of human T-lymphoblastoid cells (Brown et al. (1996) *J. Biol. Chem.* 271:27686-95). Recent studies further indicated that CD43 functions as a ligand for E-selectin on human T cells (Matsumoto et al. (2005) *J. Immunol.* 175:8042-50; Fuhlbrigge et al. (2006) *Blood,* 107:1421-6).

Interestingly, scientists have also discovered that certain nonhematopoietic tumor cells, especially colorectal adenocarcinomas, do express CD43 molecules on the cell surface. Santamaria et al. (1996) *Cancer Research,* 56:3526-9: Baeckstrom et al. (1995) *J. Biol. Chem.* 270:13688-92; Baeckstrom et al. (1997) *J. Biol. Chem.* 272:11503-9; Sikut et al. (1997) *Biochem. Biophy. Res. Commun.* 238:612-6. It has been shown that glycans on CD43 expressed in a colon carcinoma cell line (COLO 205) are different from those of leukocyte CD43 (Baeckstrom et al. (1997) *J. Biol. Chem.* 272:11503-9). Although it has been suggested that over-expression of CD43 causes activation of the tumor suppressor protein p53 (Kadaja et al. (2004) *Oncogene* 23:2523-30) and suppresses a subset of NF-kappaB target genes, partly via the inhibition of p65 transcriptional activity (Laos et al. (2006) *Int. J. Oncol.* 28:695-704), the direct evidence showing the causal role of CD43 in colon tumorigenesis is still lacking. The use of conventional anti-CD43 antibody as therapeutics for nonhematopoietic tumor cells is not practical due to its strong binding to both tumor and immune T cells. There remains a need to generate antibodies that specifically bind to a CD43 expressed on non-hematopoietic tumor or cancer cells, but do not bind to a CD43 expressed on leukocytes or other cells of hematopoietic origin. These antibodies may be useful as therapeutic agents for treating CD43 expressing nonhematopoietic cancer.

CEA is normally expressed in a variety of glandular epithelial tissues (such as the gastrointestinal, respiratory, and urogenital tracts) where it appears to be localized to the apical surface of the cells (Hammarstrom, S. (1999) *Semin. Cancer Biol.* 9, 67-81.). In tumors arising from these tissues, there is an increasing level of CEA expression extending from the apical membrane domain to the entire cell surface, together with secretion of the protein into the blood (Hammarstrom, S. (1999) *Semin. Cancer Biol.* 9, 67-81.). The excessive expression of CEA was observed in many types of cancers, including colorectal cancer, pancreatic cancer, lung cancer, gastric cancer, hepatocellular carcinoma, breast cancer, and thyroid cancer. Therefore, CEA has been used as a tumor marker and immunological assays to measure the elevated amount of CEA in the blood of cancer patients have long been utilized clinically in the prognosis and management of cancers (Gold P, et al. (1965) *J. Expl. Med.* 122:467-81; Chevinsky, A. H. (1991) *Semin. Surg. Oncol.* 7, 162-166; Shively, J. E. et al., (1985) *Crit. Rev. Oncol. Hematol.* 2, 355-399).

More importantly, CEA has become a potentially useful tumor-associated antigen for targeted therapy (Kuroki M, et al. (2002) *Anticancer Res* 22:4255-64). Two major strategies using CEA as a target for cancer immunotherapy have been developed. One method is the specific targeting of suicide genes (nitric oxide synthase (iNOS) gene) (Kuroki M. et al., (2000) *Anticancer Res.* 20(6A):4067-71) or isotopes (Wilkinson R W. et al., (2001) *PNAS USA* 98, 10256-60, Goldenberg, D. M. (1991) *Am. J. Gastroenterol.,* 86: 1392-1403, Olafsen T. et al., Protein Engineering, Design & Selection, 17, 21-27, 2004) to CEA-expressing tumor cells by anti-CEA antibodies. This method has also been extended to the use of antibody or antibody fragment conjugated with therapeutic agents, such as drugs, toxins, radionucleotides, immumodulators or cytokines. The other method is to utilize immunological cytolytic activities, specifically through antibody-dependent cellular cytotoxicity (ADCC) or complement-dependent cytotoxicity (CDC) to eliminate CEA-expressing tumor cells (Imakiire T et al., (2004) *Int. J. Cancer:* 108, 564-570). These methods often give rise to cytokine releases resulting in systemic side effects.

Antibodies recognizing a carbohydrate containing epitope present on CD-43 and CEA expressed on nonhematopoietic cancer cells have been described in U.S. Patent Application Pub. No. 2008/0171043 and PCT WO 07/146,172. These antibodies can induce apoptosis in these nonhematopoietic cancer cells in the absence of cytotoxin conjugation and immune effector function.

All references, publications, and patent applications disclosed herein are hereby incorporated by reference in their entirety.

BRIEF SUMMARY OF THE INVENTION

The invention provides antibodies (e.g., chimeric and humanized antibodies), which specifically bind to an epitope on CD43 and/or CEA expressed by a nonhematopoietic cancer cell, but do not specifically bind to a CD43 expressed by a leukocyte or by a Jurkat cell, and are capable of inducing apoptosis of the nonhematopoietic cancer cell after binding to the epitope expressed on cell surface of the nonhematopoietic cancer cell in the absence of cytotoxin conjugation and immune effector function, wherein the epitope comprises a carbohydrate, and the binding of the antibody to the epitope is inhibited by a carbohydrate comprising a Le$^a$ structure, a Le$^a$-lactose structure, a LNDFH II structure, or a LNT structure. In some embodiments, the epitope that the antibodies bind to is fucose sensitive.

In some embodiments, the antibodies are chimeric or humanized antibodies derived from murine antibody m5F1 having at least one amino acid insertion, deletion or substitution in the hinge region of the heavy chain constant region.

In some embodiments, the invention provides isolated antibodies comprising a heavy chain and a light chain, wherein (a) the heavy chain comprises a heavy chain variable region comprising three complementary determining regions from the amino acid sequence of SEQ ID NO:1 and a heavy chain constant region of human IgG1, wherein the hinge region of the heavy chain constant region comprises at least one amino acid insertion, deletion or substitution; and (b) the light chain comprises a light chain variable region comprising three complementary determining regions from the amino acid sequence of SEQ ID NO:2 and a light chain constant region from human kappa light chain or a light chain constant region from human kappa light chain comprising at least one amino acid insertion, deletion or substitution. In some embodiments, the heavy chain constant region comprises the amino acid sequence of SEQ ID NO:27 or SEQ ID NO:29.

In some embodiments, one, two, three, four, five, six, seven, eight, nine or ten amino acids are inserted N-terminal to amino acid K218 in the hinge region of human IgG1, wherein the numbering of the residue is that of the EU numbering system. See Burton, *Mol. Immunol.* 22:161-206, 1985. In some embodiments, amino acid residues KSD is inserted N-terminal to amino acid K218.

In some embodiments, the antibodies comprise: (a) a heavy chain variable region comprising three CDR regions from the amino acid sequence of SEQ ID NO:1 and a heavy chain constant region comprising the amino acid sequence selected from the group consisting of SEQ ID NOS:11-30; and (b) a light chain variable region comprising three CDR regions from the amino acid sequence of SEQ ID NO:2; and a light chain constant region comprising the amino acid sequence selected from the group consisting of SEQ ID NOS:10 and 31-37. In some embodiments, the antibody is a humanized antibody. In some embodiments, the antibody is a chimeric antibody. In some embodiments, the heavy chain variable region comprises the amino acid sequence selected from the group consisting of SEQ ID NOS: 1, 3 and 87-91. In some embodiments, the light chain variable region comprises the amino acid sequence selected from the group consisting of SEQ ID NOS: 2, 4 and 92-96. In some embodiments, the heavy chain variable region of the antibody comprises the amino acid sequence of residues 20-137 of SEQ ID NO:1 or SEQ ID NO:3 or the variable region amino acid sequence from SEQ ID NO:1 or SEQ ID NO:3. In some embodiments, the light chain variable region of the antibody comprises the amino acid sequence of residues 20-131 of SEQ ID NO:2, the variable region amino acid sequence from SEQ ID NO:2, the amino acid sequence of residues 21-132 of SEQ ID NO:4, or the variable region amino acid sequence from SEQ ID NO:4.

In some embodiments, the antibody of the invention comprises a heavy chain and a light chain, wherein the heavy chain comprises a heavy chain variable region comprising the amino acid sequence of residues 20-137 of SEQ ID NO:1 or the variable region amino acid sequence from SEQ ID NO:1, and a heavy chain constant region comprising the amino acid sequence of SEQ ID NO:27, and the light chain comprises a light chain variable region comprising the amino acid sequence of residues 20-131 of SEQ ID NO:2 or the variable region amino acid sequence from SEQ ID NO:2, and a light chain constant region comprising the amino acid sequence of SEQ ID NO:10.

In some embodiments, the antibody of the invention comprises a heavy chain and a light chain, wherein the heavy chain comprises a heavy chain variable region comprising the amino acid sequence of residues 20-137 of SEQ ID NO:1 or the variable region amino acid sequence from SEQ ID NO:1, and a heavy chain constant region comprising the amino acid sequence of SEQ ID NO:29, and the light chain comprises a light chain variable region comprising the amino acid sequence of residues 20-131 of SEQ ID NO:2 or the variable region amino acid sequence from SEQ ID NO:2, and a light chain constant region comprising the amino acid sequence of SEQ ID NO:34.

In some embodiments, the antibody of the invention comprises a heavy chain and a light chain, wherein the heavy chain comprises a heavy chain variable region comprising the amino acid sequence of residues 20-137 of SEQ ID NO:1 or the variable region amino acid sequence from SEQ ID NO:1, and a heavy chain constant region comprising the amino acid sequence of SEQ ID NO:29, and the light chain comprises a light chain variable region comprising the amino acid sequence of residues 20-131 of SEQ ID NO:2 or the variable region amino acid sequence from SEQ ID NO:2, and a light chain constant region comprising the amino acid sequence of SEQ ID NO:35.

The invention also provides an antigen-binding fragments of the antibodies described herein.

The invention also provides pharmaceutical compositions comprising one or more of the antibodies described herein or the antigen-binding fragments thereof and a pharmaceutically acceptable carrier.

The invention provides polynucleotides and vectors comprising a nucleic acid sequence encoding a heavy chain of the antibody described herein and/or a light chain of the antibody described herein or a fragment thereof. In some embodiments, the polynucleotides and the vectors comprise a nucleic acid sequence encoding a heavy chain comprising a heavy chain variable region comprising three CDR regions from the amino acid sequence of SEQ ID NO:1 and a heavy chain constant region comprising the amino acid sequence selected from the group consisting of SEQ ID NOS:11-30. In some embodiments, the polynucleotides and the vectors comprise a nucleic acid sequence encoding a light chain comprising a light chain variable region comprising three CDR regions from the amino acid sequence of SEQ ID NO:2 and a light chain constant region comprising the amino acid sequence selected from the group consisting of SEQ ID NOS:10 and 31-37.

The invention also provides host cells comprising the polynucleotides and the vectors described herein.

The invention further provides methods for producing any of the antibodies or antigen-binding fragments described herein. The methods may comprise the step of expressing one or more polynucleotides encoding the antibodies (which may be separately expressed as a single heavy or light chain, or both heavy and light chain are expressed from one vector) or antigen-binding fragments thereof in suitable host cell. In some embodiments, the expressed antibodies or antigen-binding fragments thereof are recovered and/or isolated. The invention also provides antibodies or antigen-binding fragments produced by the methods.

The invention provides a method for treating a nonhematopoietic cancer in an individual having the cancer comprising administering to the individual an effective amount of a composition comprising one or more antibodies described herein, wherein the one or more antibodies bind to the cancer cells in the individual. In some embodiments, the nonhematopoietic cancer is colorectal, pancreatic, or gastric cancer. In some embodiments, the antibody is conjugated to a cytotoxin.

The invention provides a method for delaying development of a nonhematopoietic cancer (such as delaying and/or inhibiting cancer progression) in an individual comprising administering to the individual an effective amount of a composition comprising one or more antibodies described herein, wherein the one or more antibodies bind to the cancer cells in the individual. In some embodiments, the nonhematopoietic cancer is colorectal, pancreatic, or gastric cancer. In some embodiments, the antibody is conjugated to a cytotoxin.

The invention also provides a method for treating nonhematopoietic cancer in an individual comprising administering to the individual an amount of one or more antibodies described herein and an amount of another anti-cancer agent, wherein the one or more antibodies bind to the cancer cells in the individual, and whereby the one or more antibodies and the anti-cancer agent in conjunction provide effective treatment of cancer in the individual. In some embodiments, the nonhematopoietic cancer is colorectal, pancreatic, or gastric cancer. In some embodiments, the anti-cancer agent is a chemotherapeutic agent.

The invention further provides kits comprising a pharmaceutical composition comprising one or more antibodies described herein. In some embodiments, the kits further comprise instructions for administering an effective amount of the pharmaceutical composition to an individual for treating nonhematopoietic cancer. In some embodiments, the kits comprise instructions for administering the pharmaceutical composition in conjunction with another anti-cancer agent. In some embodiments, the antibody comprises: (a) a heavy chain variable region comprising three CDR regions from the amino acid sequence of SEQ ID NO:1 and a heavy chain constant region comprising the amino acid sequence selected from the group consisting of SEQ ID NOS:11-30; and (b) a light chain variable region comprising three CDR regions from the amino acid sequence of SEQ ID NO:2; and a constant region comprising the amino acid sequence selected from the group consisting of SEQ ID NOS:10 and 31-37.

The invention also provides kits comprising a first pharmaceutical composition comprising an antibody or an antigen-binding fragment described herein, a second pharmaceutical composition comprising another anti-cancer agent, and instructions for administering the first pharmaceutical composition and the second pharmaceutical composition in conjunction to an individual for treating nonhematopoietic cancer.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 1 shows an amino acid sequence comparison and alignment between murine IgG3 heave chain constant region (SEQ ID NO:138) and human IgG1 heavy chain constant region (SEQ ID NO:139). The hinge region is underlined. As shown in the figure, amino acid identity is 214/333 (64.3%), similarity is 261/333 (78.4%), and gaps are 6/333 (1.8%).

FIG. 2(A-E) shows an amino acid sequence comparison and alignment between unmodified and modified heavy chain human IgG1 constant regions and FIG. 2F shows an amino acid sequence comparison and alignment between unmodified and modified light chain human IgG1 kappa constant regions.

FIGS. 4(A and B) shows an amino acid sequence comparison and alignment between VH(a) and VL(b) of h5F1M, h5F1A Va, h5F1A Vs, h5F1M Va, and h5F1M Vs.

DETAILED DESCRIPTION OF THE INVENTION

Definitions

Figure 3:
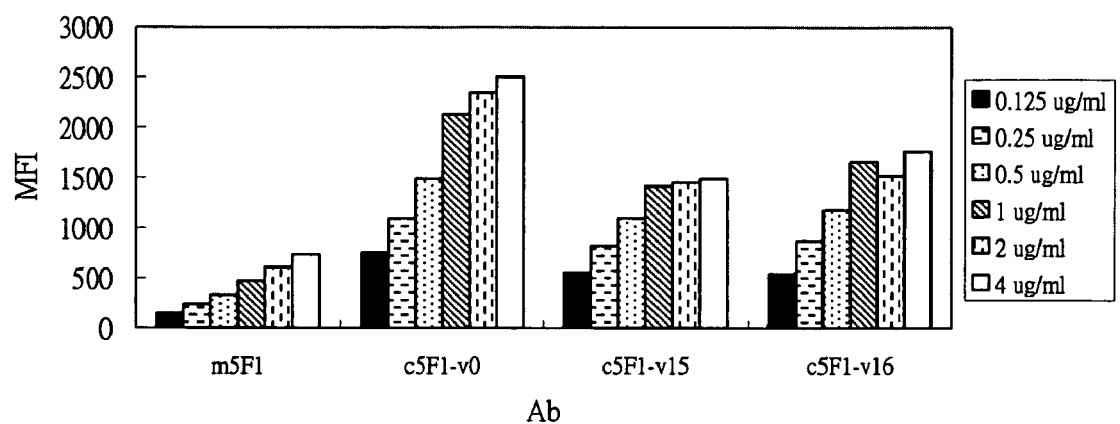
FIG. 3 shows the binding of m5F1, c5F1v0, c5F1v15, and c5F1v16 antibodies to Colo 205 from flow cytometric analysis at varying concentrations ranging from 0.125 µg/ml to 4 µg/ml. The background signals (MFI) for control antibodies are: anti-mouse second antibody: 3; anti-human second antibody: 3; mouse IgG: 4; human IgG: 5. All antibodies, m5F1, c5F1v0, c5F1v15, and c5F1v16, show significant binding to Colo205 cells over the background signals.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibody of the present invention is further intended to include bispecific, multispecific, single-chain, and chimeric and humanized molecules having affinity for a polypeptide conferred by at least one CDR region of the antibody. Antibodies of the present invention also include single domain antibodies which are either the variable domain of an antibody heavy chain or the variable domain of an antibody light chain. Holt et al., (2003), *Trends Biotechnol.* 21:484-490. Methods of making domain antibodies comprising either the variable domain of an antibody heavy chain or the variable domain of an antibody light chain, containing three of the six naturally occurring complementarity determining regions from an antibody, are also known in the art. See, e.g., Muyldermans, *Rev. Mol. Biotechnol.* 74:277-302, 2001.

As used herein, "monoclonal antibody" refers to an antibody of substantially homogeneous antibodies, i.e., the individual antibodies comprising the population are identical except for possible naturally-occurring mutations that may be present in minor amounts. Monoclonal antibodies are generally highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, (1975), *Nature,* 256:495, or may be made by recombinant DNA methods such as described in U.S. Pat. No. 4,816,567. The monoclonal antibodies may also be isolated from phage libraries generated using the techniques described in McCafferty et al., (1990), *Nature,* 348:552-554, for example.

As used herein, a "chimeric antibody" refers to an antibody having a variable region or part of variable region from a first species and a constant region from a second species. An intact chimeric antibody comprises two copies of a chimeric light chain and two copies of a chimeric heavy chain. The production of chimeric antibodies is known in the art (Cabilly et al. (1984), *Proc. Natl. Acad. Sci. USA,* 81:3273-3277; Harlow and Lane (1988), *Antibodies: a Laboratory Manual,* Cold Spring Harbor Laboratory). Typically, in these chimeric antibodies, the variable region of both light and heavy chains mimics the variable regions of antibodies derived from one species of mammals, while the constant portions are homologous to the sequences in antibodies derived from another. In some embodiments, amino acid modifications can be made in the variable region and/or the constant region.

An "isolated" antibody is one which has been identified and separated and/or recovered from a component of its natural environment.

As used herein, "substantially pure" refers to material which is at least 50% pure (i.e., free from contaminants), more preferably at least 90% pure, more preferably at least 95% pure, more preferably at least 98% pure, more preferably at least 99% pure.

As used herein, "humanized" antibodies refer to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572.

Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, *Nature Biotechnology,* 14:309-314; Sheets et al., (1998), *PNAS,* (USA) 95:6157-6162; Hoogenboom and Winter, 1991, *J. Mol. Biol.,* 227:381; Marks et al., (1991), *J. Mol. Biol.,* 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., (1991), *J. Immunol.,* 147 (1):86-95; and U.S. Pat. No. 5,750,373.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination. A constant region of an antibody generally provides structural stability and other biological functions such as antibody chain association, secretion, transplacental mobility, and complement binding, but is not involved with binding to the antigen. The amino acid sequence and corresponding exon sequences in the genes of the constant region will be dependent upon the species from which it is derived; however, variations in the amino acid sequence leading to allotypes will be relatively limited for particular constant regions within a species. The variable region of each chain is joined to the constant region by a linking polypeptide sequence. The linkage sequence is coded by a "J" sequence in the light chain gene, and a combination of a "D" sequence and a "J" sequence in the heavy chain gene.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. Nos. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, *PNAS* (USA), 95:652-656.

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202:163 (1996), may be performed.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

As used herein, "treatment" or "treating" is an approach for obtaining beneficial or desired results including and preferably clinical results. For purposes of this invention, beneficial or desired clinical results include, but are not limited to, one or more of the following: reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "individual" or a "subject" is a mammal, more preferably a human. Mammals also include, but are not limited to, farm animals, sport animals, pets (such as cats, dogs, horses), primates, mice and rats.

As use herein, the term "specifically recognizes" or "specifically binds" refers to measurable and reproducible interactions such as attraction or binding between a target and an antibody, that is determinative of the presence of the target in the presence of a heterogeneous population of molecules including biological molecules. For example, an antibody that specifically or preferentially binds to an epitope is an antibody that binds this epitope with greater affinity, avidity, more readily, and/or with greater duration than it binds to other epitopes of the target or non-target epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4 M^{-1}$, sometimes about $10^5 M^{-1}$ or $10^6 M^{-1}$, in other instances about $10^6$ $M^{-1}$ or $10^7 M^{-1}$, about $10^8$ $M^{-1}$ to $10^9 M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, the terms "cancer," "tumor," "cancerous," and "malignant" refer to or describe the physiological condition in mammals that is typically characterized by unregulated cell growth. Examples of cancer include but are not limited to, carcinoma, including adenocarcinoma, lymphoma, blastoma, melanoma, and sarcoma. More particular examples of such cancers include squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, thyroid cancer, testicular cancer, esophageal cancer, and various types of head and neck cancer.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and variations of the invention described herein include "consisting" and/or "consisting essentially of" aspects and variations.

Antibodies and Polypeptides that Specifically Bind to a Carbohydrate Epitope on CD43 and CEA Expressed on Nonhematopoietic Cancer Cells The invention provides isolated antibodies, and polypeptides derived from the antibodies, that specifically bind to an epitope on CD43 and/or CEA expressed by nonhematopoietic cancer cells, but do not specifically bind to a CD43 expressed by a leukocyte (such as a peripheral T cell) or a Jurkat cell.

In some embodiments, the invention provides an antibody comprising: a heavy chain variable region comprising one or more CDR regions of SEQ ID NO:1 and a heavy chain constant region of human IgG1. In some embodiments, the antibody comprises a light chain variable region comprising one or more CDR regions of SEQ ID NO:2 and a kappa light chain constant region.

In some embodiments, one or more amino acid residues in the heavy chain constant region and/or the light chain constant region of the antibody are modified (including amino acid insertion, deletion, and substitution). For example, amino acid residues as shown in the Examples may be modified.

In some embodiments, the invention provides an antibody comprising: (a) a heavy chain variable region comprising one or more CDR regions from the amino acid sequence of SEQ ID NO:1 and a heavy chain constant region comprising the amino acid sequence selected from the group consisting of SEQ ID NOS:11-30; and (b) a light chain variable region comprising one or more CDR regions from the amino acid sequence of SEQ ID NO:2; and a light chain constant region comprising the amino acid sequence selected from the group consisting of SEQ ID NOS:10 and 31-37. In some embodiments, the one or more CDR regions from the amino acid sequence of SEQ ID NO:1 are three CDR regions from the amino acid sequence of SEQ ID NO:1. In some embodiments, the one or more CDR regions from the amino acid sequence of SEQ ID NO:2 are three CDR regions from the amino acid sequence of SEQ ID NO:2. In some embodiments, CDR1, CDR2, and CDR3 in the heavy chain comprise the amino acid sequences of SYVMH (SEQ ID NO:168), YINPYNGGTQYNEKFKG (SEQ ID NO:169), and RTF-PYYFDY (SEQ ID NO:170), respectively. In some embodiments, CDR1, CDR2, and CDR3 in the light chain comprise the amino acid sequences of RSSQSILHSNGNTYLE (SEQ ID NO:171), KVSNRFS (SEQ ID NO:172); and FQG-SHAPLT (SEQ ID NO:173), respctively. In some embodiments, the heavy chain variable region comprises the variable region amino acid sequence from SEQ ID NO:1 or 3. In some embodiments, the light chain variable region comprises the variable region amino acid sequence from SEQ ID NO:2 or 4.

In some embodiments, the one or more CDRs derived from the amino acid sequence of SEQ ID NO:1 and/or SEQ ID NO:2 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six CDRs of SEQ ID NO:1 and/or SEQ ID NO:2.

The antibodies and polypeptides of the invention may further have one or more of the following characteristics: (a) binding of the antibody or the polypeptide to the epitope is reduced if the molecule comprising the epitope is treated with α-1→(2,3,4)-Fucosidase; (b) binding of the antibody or the polypeptide to the epitope is inhibited by a carbohydrate comprising a Le$^a$ structure, a Le$^a$-lactose structure, a LNDFH II structure, and/or a LNT structure; (c) induce death of the nonhematopoietic cancer cell (such as through apoptosis) after binding to the epitope expressed on the cell surface of the cancer cell in the absence of cytotoxin conjugation and immune effector function; (d) inhibit cell growth or proliferation of the nonhematopoietic cancer cell after binding to the epitope expressed on the cell surface of the cancer cell; and (e) treat or prevent nonhematopoietic cancer expressing the epitope on the cell surface, such as colorectal cancer and gastric cancer, in an individual.

As used herein, the term "inhibition" includes partial and complete inhibition. For example, binding of the antibody or the polypeptide to the epitope on CD43 and CEA is inhibited by at least about 20%, at least about 30%, at least about 40%, at least about 50%, at least about 60%, at least about 70%, at least about 80%, or at least about 90% by a carbohydrate comprising a Le$^a$ structure, a Le$^a$-lactose structure, a LNDFH II structure, or a LNT structure. Binding of the antibody to the epitope may be inhibited by direct competition or by other mechanisms.

Examples of non-hematopoietic cancer cells expressing the epitope include, but are not limited to, colorectal cancer cells (such as COLO 205 and DLD-1), gastric cancer cells (such as NCI-N87), and pancreatic cancer cells (such as SU.86.86, ATCC No. CRL-1837).

The antibodies and polypeptides of the present invention may recognize an extracellular domain of a CD43 present on a nonhematopoietic cancer cell, but does not bind to an extracellular domain of a leukocyte CD43 (e.g., a peripheral T cell), or an extracellular domain of CD43 expressed on a Jurkat cell (a lymphoblastoid leukemia cell). In some embodiments, the novel antibodies or polypeptides of the invention do not specifically bind to a CD43 expressed by a cell of hematopoietic origin.

The invention encompasses modifications to antibodies or polypeptide described herein, including functionally equivalent antibodies which do not significantly affect their properties and variants which have enhanced or decreased activity and/or affinity. For example, amino acid sequence of antibody may be mutated to obtain an antibody with the desired binding affinity to the CD43 or CEA expressed by the cancer cell. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in the table below under the heading of "conservative substitutions". If such substitutions result in a change in biological activity, then more substantial changes, denominated "exemplary substitutions" in the table below, or as further described below in reference to amino acid classes, may be introduced and the products screened.

TABLE 1

Amino Acid Substitutions.

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDRH3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, (1997), *Chem. Immunol.* 65:111-128; Wright and Morrison, (1997), *TibTECH* 15:26-32). The oligosaccharide side chains of the immunoglobulins affect the protein's function (Boyd et al., (1996), *Mol. Immunol.* 32:1311-1318; Wittwe and Howard, (1990), *Biochem.* 29:4175-4180) and the intramolecular interaction between portions of the glycoprotein, which can affect the conformation and presented three-dimensional surface of the glycoprotein (Hefferis and Lund, supra; Wyss and Wagner, (1996), *Current Opin. Biotech.* 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetyl-glucosaminyltransferase III (GnTIII), a glycosyltransferase catalyzing formation of bisecting GlcNAc, was reported to have improved ADCC activity (Umana et al., (1999), *Mature Biotech.* 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., (1997), *J. Biol. Chem.* 272:9062-9070).

The antibodies of the invention can encompass antibody fragments (e.g., Fab, Fab', F(ab')$_2$, Fv, Fc, etc.), chimeric antibodies, single chain (ScFv), mutants thereof, fusion proteins comprising an antibody portion, and any other modified configuration of the immunoglobulin molecule that comprises an antigen recognition site of the required specificity. The antibodies may be murine, rat, camel, human, or any other origin (including humanized antibodies).

The binding affinity of the polypeptide (including antibody) to CD43 or CEA may be less than any of about 500 nM, about 400 nM, about 300 nM, about 200 nM, about 100 nM, about 50 nM, about 10 nM, about 1 nM, about 500 μM, about 100 μM, or about 50 μM. As is well known in the art, binding affinity can be expressed as $K_D$, or dissociation constant, and an increased binding affinity corresponds to a decreased $K_D$. One way of determining binding affinity of antibodies to CD43 or CEA is by measuring binding affinity of monofunctional Fab fragments of the antibody. To obtain monofunctional Fab fragments, an antibody (for example, IgG) can be cleaved with papain or expressed recombinantly. The affinity of a Fab fragment of an antibody can be determined by surface plasmon resonance (BIAcore3000™ surface plasmon resonance (SPR) system, BIAcore, INC, Piscaway N.J.) and ELISA. Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibodies and polypeptides of the invention reduce the number of cancer cells, and/or inhibit cell growth or proliferation of tumor or cancer cells that have the epitope. Preferably, the reduction in cell number or inhibition of cell growth or proliferation is by at least about 10%, about 20%, about 30%, about 40%, about 50%, about 65%, about 75%, or greater as compared to the cell not treated with the antibody or polypeptides. Cancer cells include, but are not limited to, colorectal cancer, pancreatic cancer, lung cancer, and gastric cancer.

In some embodiments, the antibodies and polypeptides of the invention are capable of inducing cell death alone, for example through apoptosis, after binding the epitope expressed on cell surface of the nonhematopoietic cancer cell. The term "induce cell death" as used herein, means that the antibodies or polypeptides of the present invention, can directly interact with a molecule expressed on the cell surface, and the binding/interaction alone is sufficient to induce cell death in the cells without the help of other factors such as cytotoxin conjugation or other immune effector functions, i.e., complement-dependent cytotoxicity (CDC), antibody-dependent cellular cytotoxicity (ADCC), or phagocytosis.

As used herein, the term "apoptosis" refers to gene-directed process of intracellular cell destruction. Apoptosis is distinct from necrosis; it includes cytoskeletal disruption, cytoplasmic shrinkage and condensation, expression of phosphatidylserine on the outer surface of the cell membrane and blebbing, resulting in the formation of cell membrane bound vesicles or apoptotic bodies. The process is also referred to as "programmed cell death." During apoptosis, characteristic phenomena such as curved cell surfaces, condensation of nuclear chromatin, fragmentation of chromosomal DNA, and loss of mitochondrial function are observed. Various known technologies may be used to detect apoptosis, such as staining cells with Annexin V, propidium iodide, DNA fragmentation assay and YO-PRO-1 (Invitrogen).

Methods of detecting cell death (such as apoptosis) include, but are not limited to, detecting morphology, DNA fragmentation, enzymatic activity, and polypeptide degradation, etc. See Siman et al., U.S. Pat. No. 6,048,703; Martin and Green (1995), Cell, 82: 349-52; Thornberry and Lazebnik (1998), Science, 281:1312-6; Zou et al., U.S. Pat. No. 6,291, 643; Scovassi and Poirier (1999), Mol. Cell. Biochem., 199: 125-37; Wyllie et al. (1980), Int. Rev. Cytol., 68:251-306; Belhocine et al. (2004), Technol. Cancer Res. Treat., 3(1):23-32, which are incorporated herein by reference.

In some embodiments, the antibodies and polypeptides of the invention recognize a conformation epitope expressed on a nonhematopoietic cancer cell, and this epitope includes a structure having physical and chemical characteristics equivalent to the structure formed by tripeptide, N'-Trp-Pro-Ile-C'. As used herein, "an epitope which includes a structure having physical and chemical characteristics equivalent to the structure formed by a peptide" means that both structures have a similar physical and chemical property related to antibody binding so that an antibody that specifically binds to one structure would bind to both structures. In some embodiments, the antibodies and polypeptides bind to a polypeptide comprising amino acid sequence, N'-Trp-Pro-Ile-C' at the N-terminus of the polypeptide.

In some embodiments, the antibodies and polypeptides of the invention competes with antibody m5F1 or h5F1 for binding to the epitope expressed on the cell surface of the cancer cell. In some embodiments, the antibodies or polypeptides of the invention binding to an epitope on CD43 or CEA to which at least one of antibodies m5F1 or h5F1 binds.

Competition assays can be used to determine whether two antibodies bind the same epitope by recognizing identical or sterically overlapping epitopes or one antibody competitively inhibits binding of another antibody to the antigen. These assays are known in the art. Typically, antigen or antigen expressing cells is immobilized on a multi-well plate and the ability of unlabeled antibodies to block the binding of labeled antibodies is measured. Common labels for such competition assays are radioactive labels or enzyme labels.

In some embodiments, the CDR is a Kabat CDR. In other embodiments, the CDR is a Chothia CDR. In other embodiments, the CDR is a combination of a Kabat and a Chothia CDR (also termed "combined CDR" or "extended CDR"). In other words, for any given embodiment containing more than one CDR, the CDRs may be any of Kabat, Chothia, and/or combined.

Methods of making antibodies and polypeptides derived from the antibodies are known in the art and are disclosed herein. Antibodies generated may be tested for having specific binding to the epitope on CD-43 or CEA expressed by the nonhematopoietic cancer or tumor cells, but no specific binding to CD43 expressing leukocyte, Jurkat cells, and/or other CD43 expressing cells of hematopoietic origin. Cancer cells or extracellular domain (including fragments thereof) containing the epitope may be used for testing.

Jurkat cell line is a lymphoblastoid leukemia cell, and was established from the peripheral blood of a 14 year old boy by Schneider et al. Schneider et al., Int. J. Cancer 19:621-626, 1977. Various Jurkat cell lines are commercially available, for example, from American Type Culture Collection (e.g., ATCC TIB-152, ATCC TIB-153, ATCC CRL-2678).

The binding specificity of the antibodies produced may be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980), Anal. Biochem., 107:220.

The antibodies identified may further be tested for their capabilities to induce cell death (e.g., apoptosis), and/or inhibiting cell growth or proliferation using methods known in the art and described herein.

The antibodies of the invention can also be made by recombinant DNA methods, such as those described in U.S. Pat. Nos. 4,816,567 and 6,331,415, which are hereby incorporated by reference. For example, DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

In some embodiment, the antibodies of the present invention are expressed from two expression vectors. The first expression vector encodes a heavy chain of the antibody (e.g., a humanized antibody), comprising a first part encoding a variable region of the heavy chain of the antibody, and a second part encoding a constant region of the heavy chain of the antibody. In some embodiments, the first part encodes a heavy chain comprising a heavy chain variable region comprising one or more CDR regions from the amino acid sequence of SEQ ID NO:1 and a heavy chain constant region comprising the amino acid sequence selected from the group consisting of SEQ ID NOS:11-30. In some embodiments, the one or more CDR regions from the amino acid sequence of SEQ ID NO:1 are three CDR regions from the amino acid sequence of SEQ ID NO:1. The second expression vector encodes a light chain of the antibody, comprising a first part encoding a variable region of the light chain of the antibody, and a second part encoding a constant region of the light chain of the antibody. In some embodiments, the first part encodes a light chain comprising a light chain variable region comprising one or more CDR regions from the amino acid sequence of SEQ ID NO:2 and a light chain constant region comprising the amino acid sequence selected from the group consisting of SEQ ID NOS:10 and 31-37. In some embodiments, the one or more CDR regions from the amino acid sequence of SEQ ID NO:2 are three CDR regions from the amino acid sequence of SEQ ID NO:2.

Alternatively, the antibodies (e.g., a humanized antibody) of the present invention are expressed from a single expression vector. The single expression vector encodes both the heavy chain and light chain of the antibodies of the present invention. In some embodiments, the expression vector comprises a polynucleotide sequence encoding a heavy chain comprising a heavy chain variable region comprising one or more CDR regions from the amino acid sequence of SEQ ID NO:1 and a heavy chain constant region comprising the amino acid sequence selected from the group consisting of SEQ ID NOS:11-30, and a light chain variable region comprising one or more CDR regions from the amino acid sequence of SEQ ID NO:2 and a light chain constant region comprising the amino acid sequence selected from the group consisting of SEQ ID NOS:10 and 31-37. In some embodiments, the one or more CDR regions from the amino acid sequence of SEQ ID NO:1 are three CDR regions from the amino acid sequence of SEQ ID NO:1. In some embodiments, the one or more CDR regions from the amino acid sequence of SEQ ID NO:2 are three CDR regions from the amino acid sequence of SEQ ID NO:2.

Normally the expression vector has transcriptional and translational regulatory sequences which are derived from species compatible with a host cell. In addition, the vector ordinarily carries a specific gene(s) which is (are) capable of providing phenotypic selection in transformed cells.

A wide variety of recombinant host-vector expression systems for eukaryotic cells are known and can be used in the invention. For example, *Saccharomyces cerevisiae*, or common baker's yeast, is the most commonly used among eukaryotic microorganisms, although a number of other strains, such as *Pichia pastoris*, are available. Cell lines derived from multicellular organisms such as Sp2/0 or Chinese Hamster Ovary (CHO), which are available from the ATCC, may also be used as hosts. Typical vector plasmids suitable for eukaryotic cell transformations are, for example, pSV2neo and pSV2gpt (ATCC), pSVL and pSVK3 (Pharmacia), and pBPV-1/pML2d (International Biotechnology, Inc.).

The eukaryotic host cells useful in the present invention are, preferably, hybridoma, myeloma, plasmacytoma or lymphoma cells. However, other eukaryotic host cells may be suitably utilized provided the mammalian host cells are capable of recognizing transcriptional and translational DNA sequences for expression of the proteins; processing the leader peptide by cleavage of the leader sequence and secretion of the proteins; and providing post-translational modifications of the proteins, e.g., glycosylation.

Accordingly, the present invention provides eukaryotic host cells which are transformed by recombinant expression vectors comprising DNA constructs disclosed herein and which are capable of expressing the antibodies or polypeptides of the present invention. In some embodiments, the transformed host cells of the invention, therefore, comprise at least one DNA construct comprising the light and heavy chain DNA sequences described herein, and transcriptional and translational regulatory sequences which are positioned in relation to the light and heavy chain-encoding DNA sequences to direct expression of antibodies or polypeptides.

The host cells used in the invention may be transformed in a variety of ways by standard transfection procedures well known in the art. Among the standard transfection procedures which may be used are electroporation techniques, protoplast fusion and calcium-phosphate precipitation techniques. Such techniques are generally described by F. Toneguzzo et al. (1986), *Mol. Cell. Biol.*, 6:703-706; G. Chu et al., *Nucleic Acid Res.* (1987), 15:1311-1325; D. Rice et al., *Proc. Natl. Acad. Sci. USA* (1979), 79:7862-7865; and V. Oi et al., *Proc. Natl. Acad. Sci. USA* (1983), 80:825-829.

In the case of two expression vectors, the two expression vectors can be transferred into a host cell one by one separately or together (co-transfer or co-transfect).

The present invention also provides a method for producing the antibodies or polypeptides, which comprises culturing a host cell comprising an expression vector(s) encoding the antibodies or the polypeptides, and recovering the antibodies or polypeptides from the culture by ways well known to one skilled in the art. In some embodiments, the antibodies may be isolated or purified by conventional immunoglobulin purification procedures such as, for example, protein A-Sepharose, hydroxylapatite chromatography, gel electrophoresis, dialysis, or affinity chromatography.

Furthermore, the desired antibodies can be produced in a transgenic animal. A suitable transgenic animal can be obtained according to standard methods which include micro-injecting into eggs the appropriate expression vectors, transferring the eggs into pseudo-pregnant females and selecting a descendant expressing the desired antibody.

The present invention also provides chimeric antibodies that specifically recognize the epitope on CD43 and CEA expressed by a cancer cell. For example, the variable and constant regions of the chimeric antibody are from separate species. In some embodiments, the variable regions of both heavy chain and light chain are from the murine antibodies described herein. In some embodiments, the variable regions comprise amino acid sequences from variable regions from SEQ ID NO:1 and SEQ ID NO:2, or residues 20-137 of SEQ ID NO:1 and residues 20-131 of SEQ ID NO:2. In some embodiments, the constant regions of both the heavy chain and light chain are from human antibodies.

The chimeric antibody of the present invention can be prepared by techniques well-established in the art. See for example, U.S. Pat. Nos. 6,808,901, 6,652,852, 6,329,508, 6,120,767 and 5,677,427, each of which is hereby incorporated by reference. In general, the chimeric antibody can be prepared by obtaining cDNAs encoding the heavy and light chain variable regions of the antibodies, inserting the cDNAs into an expression vector, which upon being introduced into eukaryotic host cells, expresses the chimeric antibody of the present invention. Preferably, the expression vector carries a functionally complete constant heavy or light chain sequence so that any variable heavy or light chain sequence can be easily inserted into the expression vector.

The present invention provides a humanized antibody that specifically recognizes the epitope on CD43 and CEA expressed by a nonhematopoietic cancer cell. The humanized antibody is typically a human antibody in which residues from CDRs are replaced with residues from CDRs of a non-human species such as mouse, rat or rabbit having the desired specificity, affinity and capacity. In some instances, Fv framework residues of the human antibody are replaced by corresponding non-human residues.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530, 101; 5,693,761; 5,693,762; 5,585,089; 6,180,370; and 6,548, 640. For example, the constant region may be engineered to more resemble human constant regions to avoid immune response if the antibody is used in clinical trials and treatments in humans. See, for example, U.S. Pat. Nos. 5,997,867 and 5,866,692.

It is important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. The humanized antibodies may also contain modifications in the hinge region to improve one or more characteristics of the antibody.

In another alternative, antibodies may be screened and made recombinantly by phage display technology. See, for example, U.S. Pat. Nos. 5,565,332; 5,580,717; 5,733,743 and 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., *Current Opinion in Structural Biology* 3, 564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/Technol.* 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin. It is apparent that although the above discussion pertains to humanized antibodies, the general principles discussed are applicable to customizing antibodies for use, for example, in dogs, cats, primates, equines and bovines.

In certain embodiments, the antibody is a fully human antibody. Non-human antibodies that specifically bind an antigen can be used to produce a fully human antibody that binds to that antigen. For example, the skilled artisan can employ a chain swapping technique, in which the heavy chain of a non-human antibody is co-expressed with an expression library expressing different human light chains. The resulting hybrid antibodies, containing one human light chain and one non-human heavy chain, are then screened for antigen binding. The light chains that participate in antigen binding are then co-expressed with a library of human antibody heavy chains. The resulting human antibodies are screened once more for antigen binding. Techniques such as this one are further described in U.S. Pat. No. 5,565,332. In addition, an antigen can be used to inoculate an animal that is transgenic for human immunoglobulin genes. See, e.g., U.S. Pat. No. 5,661,016.

The antibody may be a bispecific antibody, a monoclonal antibody that has binding specificities for at least two different antigens, can be prepared using the antibodies disclosed herein. Methods for making bispecific antibodies are known in the art (see, e.g., Suresh et al., (1986), *Methods in Enzymology* 121:210). Traditionally, the recombinant production of bispecific antibodies was based on the coexpression of two immunoglobulin heavy chain-light chain pairs, with the two heavy chains having different specificities (Millstein and Cuello, (1983), *Nature* 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; and EP 03089). Heteroconjugate antibodies may be made using any convenient cross-linking methods. Suitable cross-linking agents and techniques are well known in the art, and are described in U.S. Pat. No. 4,676,980.

Single chain Fv fragments may also be produced, such as described in Iliades et al., 1997, *FEBS Letters*, 409:437-441. Coupling of such single chain fragments using various linkers is described in Kortt et al., 1997, *Protein Engineering*, 10:423-433. A variety of techniques for the recombinant production and manipulation of antibodies are well known in the art.

It is contemplated that the present invention encompasses not only the monoclonal antibodies described above, but also any fragments thereof containing the active binding region of the antibodies, such as Fab, F(ab')$_2$, scFv, Fv fragments and the like. Such fragments can be produced from the monoclonal antibodies described herein using techniques well established in the art (Rousseaux et al. (1986), in *Methods Enzymol.*, 121:663-69 Academic Press).

Methods of preparing antibody fragment are well known in the art. For example, an antibody fragment can be produced by enzymatic cleavage of antibodies with pepsin to provide a 100 Kd fragment denoted F(ab')$_2$. This fragment can be further cleaved using a thiol reducing agent, and optionally a blocking group for the sulfhydryl groups resulting from cleavage of disulfide linkages, to produce 50 Kd Fab' monovalent fragments. Alternatively, an enzymatic cleavage using papain produces two monovalent Fab fragments and an Fc fragment directly. These methods are described, for example, by U.S. Pat. Nos. 4,036,945 and 4,331,647 and references contained therein, which patents are incorporated herein by reference. Also, see Nisonoff et al. (1960), *Arch Biochem. Biophys.* 89: 230; Porter (1959), *Biochem. J.* 73: 119, Edelman et al., in *METHODS IN ENZYMOLOGY* VOL. 1, page 422 (Academic Press 1967).

Alternatively, the Fab can be produced by inserting DNA encoding Fab of the antibody into an expression vector for prokaryote or an expression vector for eukaryote, and introducing the vector into a prokaryote or eukaryote to express the Fab.

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

In some embodiments, the antibody of the invention may be modified using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

The antibody or polypeptide of the invention may be conjugated (for example, linked) to an agent, such as a therapeutic agent and a label. Examples of therapeutic agents are radioactive moieties, cytotoxins, or chemotherapeutic molecules.

The antibody (or polypeptide) of this invention may be linked to a label such as a fluorescent molecule, a radioactive molecule, an enzyme, or any other labels known in the art. As used herein, the term "label" refers to any molecule that can be detected. In a certain embodiment, an antibody may be labeled by incorporation of a radiolabeled amino acid. In a certain embodiment, biotin moieties that can be detected by marked avidin (e.g., streptavidin containing a fluorescent marker or enzymatic activity that can be detected by optical or colorimetric methods) may be attached to the antibody. In certain embodiments, a label may be incorporated into or attached to another reagent which in turn binds to the antibody of interest. For example, a label may be incorporated into or attached to an antibody that in turn specifically binds the antibody of interest. In certain embodiments, the label or marker can also be therapeutic. Various methods of labeling polypeptides and glycoproteins are known in the art and may be used. Certain general classes of labels include, but are not limited to, enzymatic, fluorescent, chemiluminescent, and radioactive labels. Examples of labels for polypeptides include, but are not limited to, the following: radioisotopes or radionucleoides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., fluorescein isothocyanate (FITC), rhodamine, lanthanide phosphors, phycoerythrin (PE)), enzymatic labels (e.g., horseradish peroxidase, β-galactosidase, luciferase, alkaline phosphatase, glucose oxidase, glucose-6-phosphate dehydrogenase, alcohol dehydrogenase, malate dehydrogenase, penicillinase, luciferase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The invention also provides pharmaceutical compositions comprising antibodies or polypeptides described herein, and a pharmaceutically acceptable carrier or excipients. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington, The Science and Practice of Pharmacy* 20th Ed. Mack Publishing (2000).

In some embodiments, the invention provides compositions (described herein) for use in any of the methods described herein, whether in the context of use as a medicament and/or use for manufacture of a medicament.

Polynucleotides, Vectors and Host Cells

The invention also provides polynucleotides comprising a nucleotide sequence encoding any of the monoclonal antibodies and polypeptides described herein. In some embodiments, the polypeptides comprise the sequences of light chain and/or heavy chain variable regions.

In some embodiments, the polynucleotides comprise a nucleic acid sequence encoding a heavy chain comprising a heavy chain variable region comprising one or more CDR regions from the amino acid sequence of SEQ ID NO:1 and a heavy chain constant region comprising the amino acid sequence selected from the group consisting of SEQ ID NOS: 11-30, and/or a nucleic acid sequence encoding a light chain comprising a light chain variable region comprising one or more CDR regions from the amino acid sequence of SEQ ID NO:2 and a light chain constant region comprising the amino acid sequence selected from the group consisting of SEQ ID NOS:10 and 31-37. In some embodiments, the polynucleotides comprise a nucleic acid sequence encoding a heavy chain comprising a heavy chain variable region comprising three CDR regions from the amino acid sequence of SEQ ID NO:1 and a heavy chain constant region comprising the amino acid sequence selected from the group consisting of SEQ ID NOS:11-30, and/or a nucleic acid sequence encoding a light chain comprising a light chain variable region comprising three CDR regions from the amino acid sequence of SEQ ID NO:2 and a constant region comprising the amino acid sequence selected from the group consisting of SEQ ID NOS: 10 and 31-37.

It is appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Thus, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein can, but need not, have an altered structure or function. Alleles can be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides can be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston (1994).

The invention also provides vectors (e.g., cloning vectors, expression vectors) comprising a nucleic acid sequence encoding any of the polypeptides (including antibodies) described herein. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides or vectors described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

Diagnostic Uses

The present invention provides a method of using the antibodies, polypeptides and polynucleotides of the present invention for detection, diagnosis and monitoring of a disease, disorder or condition associated with the epitope expression (either increased or decreased relative to a normal sample, and/or inappropriate expression, such as presence of expression in tissues(s) and/or cell(s) that normally lack the epitope expression).

In some embodiments, the method comprises detecting the epitope expression in a sample obtained from a subject suspected of having cancer, such colorectal, pancreatic, gastric, and lung cancer. Preferably, the method of detection comprises contacting the sample with an antibody, polypeptide, or polynucleotide of the present invention and determining whether the level of binding differs from that of a control or comparison sample. The method is also useful to determine whether the antibodies or polypeptides described herein are an appropriate treatment for the patient.

As used herein, the term "a sample" or "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "A sample" or "a biological sample" further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term "a sample" or "a biological sample" can also refer to cells or tissue analyzed in vivo, i.e., without removal from animal. Typically, "a sample" or "a biological sample" will contain cells from the animal, but the term can also refer to non-cellular biological material, such as non-cellular fractions of blood, saliva, or urine, that can be used to measure the cancer-associated polynucleotide or polypeptides levels. "A sample" or "a biological sample" further refers to a medium, such as a nutrient broth or gel in which an organism has been propagated, which contains cellular components, such as proteins or nucleic acid molecules.

In one embodiment, the cells or cell/tissue lysate are contacted with an antibody and the binding between the antibody and the cell is determined. When the test cells are shown binding activity as compared to a control cell of the same tissue type, it may indicate that the test cell is cancerous. In some embodiments, the test cells are from human tissues.

Various methods known in the art for detecting specific antibody-antigen binding can be used. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). General techniques to be used in performing the various immunoassays noted above are known to those of ordinary skill in the art.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art.

In some embodiments, the polypeptides including antibodies of the invention need not be labeled, and the presence thereof can be detected using a labeled antibody which binds to the antibodies of the invention.

The antibodies of the present invention can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The antibodies and polypeptides can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$I, or $^{3}$H) so that the cells or tissue of interest can be localized using immunoscintiography.

The antibody may also be used as staining reagent in pathology using techniques well known in the art.

Therapeutic Uses

The antibodies of the present invention are capable of inducing nonhematopoietic cancer cell death. Thus, the present invention provides therapeutic uses of the antibodies and polypeptides of the present invention in treating and/or delaying development of cancer, such as, colorectal cancer, lung cancer, pancreatic cancer, gastric cancer, breast cancer, hepatocellular carcinoma, and thyroid cancer. Any cancer may be treated, such as colon cancer, colorectal cancer, lung cancer, breast cancer, brain tumor, malignant melanoma, renal cell carcinoma, bladder cancer, lymphomas, T cell lymphomas, multiple myeloma, gastric cancer, pancreas cancer, cervical cancer, endometrial carcinoma, ovarian cancer, esophageal cancer, liver cancer, head and neck squamous cell carcinoma, cutaneous cancer, urinary tract carcinoma, prostate cancer, choriocarcinoma, pharyngeal cancer, laryngeal cancer, thecomatosis, androblastoma, endometrium hyperplasy, endometriosis, embryoma, fibrosarcoma, Kaposi's sarcoma, hemangioma, cavernous hemangioma, angioblastoma, retinoblastoma, astrocytoma, neurofibroma, oligodendroglioma, medulloblastoma, ganglioneuroblastoma, glioma, rhabdomyosarcoma, hamartoblastoma, osteogenic sarcoma, leiomyosarcoma, thyroid sarcoma and Wilms tumor, as long as the cancer cell expresses the epitope recognized by the antibodies described herein. The method may further comprise a step of detecting the binding between an antibody or a polypeptide described herein and a tumor or cancer cell in an individual to be treated.

Generally, an effective amount of a composition comprising an antibody or a polypeptide is administered to a subject in need of treatment, thereby inhibiting growth of the cancer cell and/or inducing death of the cancer cell. Preferably the composition is formulated with a pharmaceutically acceptable carrier.

In one embodiment, the composition is formulated for administration by intraperitoneal, intravenous, subcutaneous, and intramuscular injections, and other forms of administration such as oral, mucosal, via inhalation, sublingually, etc.

In another embodiment, the present invention also contemplates administration of a composition comprising the antibodies or polypeptides of the present invention conjugated to other molecules, such as detectable labels, or therapeutic or cytotoxic agents. The agents may include, but are not limited to radioisotopes, toxins, toxoids, inflammatory agents, enzymes, antisense molecules, peptides, cytokines, or chemotherapeutic agents. Methods of conjugating the antibodies with such molecules are generally known to those of skilled in the art. See, e.g., PCT publications WO 92/08495; WO 91/14438; WO 89/12624; U.S. Pat. No. 5,314,995; and EP 396,387; the disclosures of which are incorporated herein by reference in their entireties.

In one embodiment, the composition comprises an antibody or polypeptide conjugated to a cytotoxic agent. Cytotoxic agents can include any agents that are detrimental to cells. A preferred class of cytotoxic agents that can be conjugated to the antibodies or fragments may include, but are not limited to paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The dosage required for the treatment depends on the choice of the route of administration, the nature of the formulation, the nature of the subject's illness, the subject's size, weight, surface area, age and sex; other drugs being administered, and the judgment of the attending physician. Suitable dosages are in the range of 0.01-1000.0 mg/kg.

Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or less, is administered. For repeated administrations over several days or longer, depending on the condition, the treatment is sustained until a desired suppression of disease symptoms occurs. An exemplary dosing regimen comprises administering a weekly dose of about 6 mg/kg of the antibody. However, other dosage regimens may be useful, depending on the pattern of pharmacokinetic decay that the practitioner wishes to achieve. Empirical considerations, such as the half-life, generally will contribute to determination of the dosage. The progress of this therapy is easily monitored by conventional techniques and assays.

In some subjects, more than one dose may be required. Frequency of administration may be determined and adjusted over the course of therapy. For example, frequency of administration may be determined or adjusted based on the type and stage of the cancer to be treated, whether the agent is administered for preventive or therapeutic purposes, previous therapy, the patient's clinical history and response to the agent, and the discretion of the attending physician. Typically the clinician will administer a therapeutic antibody (such as a chimeric 5F1 antibody), until a proper dosage is reached to achieves the desired result. In some cases, sustained continuous release formulations of antibodies may be appropriate. Various formulations and devices for achieving sustained release are known in the art.

In one embodiment, dosages for the antibodies or polypeptides may be determined empirically in subjects who have been given one or more administration(s). Subjects are given incremental dosages of the antibodies or polypeptides. To assess efficacy of the antibodies or polypeptides, markers of the disease symptoms such as CD43 or CEA can be monitored. Efficacy in vivo can also be measured by assessing tumor burden or volume, the time to disease progression (TDP), and/or determining the response rates (RR).

Administration of an antibody or polypeptide in accordance with the method in the present invention can be continuous or intermittent, depending, for example, upon the recipient's physiological condition, whether the purpose of the administration is therapeutic or prophylactic, and other factors known to skilled practitioners. The administration of an antibody or a polypeptide may be essentially continuous over a preselected period of time or may be in a series of spaced dose.

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

In another embodiment, the composition can comprise one or more anti-cancer agents, one or more antibodies described herein, or with an antibody or polypeptide that binds to a different antigen. Such composition can contain at least one, at least two, at least three, at least four, at least five different antibodies. The antibodies and other anti-cancer agents may be in the same formulation (e.g., in a mixture, as they are often denoted in the art), or in separate formulations but are administered concurrently or sequentially, are particularly useful in treating a broader range of population of individuals.

A polynucleotide encoding any of the antibodies or polypeptides of the present invention can also be used for delivery and expression of any of the antibodies or polypeptides of the present invention in a desired cell. It is apparent that an expression vector can be used to direct expression of the antibody or polypeptide. The expression vector can be administered by any means known in the art, such as intraperitoneally, intravenously, intramuscularly, subcutaneously, intrathecally, intraventricularly, orally, enterally, parenterally, intranasally, dermally, sublingually, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding any of the antibodies or polypeptides of the present invention can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al. (1990), *Proc. Natl. Acad. Sci. USA*, 87:3655; Wu et al. (1991), *J. Biol. Chem.* 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol.

The therapeutic polynucleotides and polypeptides of the present invention can be delivered using gene delivery vehicles. The gene delivery vehicle can be of viral or non-viral origin (see generally, Jolly (1994), *Cancer Gene Therapy* 1:51; Kimura (1994), *Human Gene Therapy* 5:845; Connelly (1985), *Human Gene Therapy* 1:185; and Kaplitt (1994), *Nature Genetics* 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP Patent No. 0 345 242; alphavirus-based vectors, e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors, e.g., PCT Publication Nos. WO 94/12649, WO 93/03769; WO 93/19191; WO 94/28938; WO 95/11984 and WO 95/00655. Administration of DNA linked to killed adenovirus as described in Curiel (1992), *Hum. Gene Ther.* 3:147 can also be employed.

Non-viral delivery vehicles and methods can also be employed, including, but are not limited to, polycationic condensed DNA linked or unlinked to killed adenovirus alone (see, e.g., Curiel (1992), *Hum. Gene Ther.* 3:147); ligand-linked DNA (see, e.g., Wu (1989), *J. Biol. Chem.* 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes.

Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent NO. 0 524 968. Additional approaches are described in Philip (1994), *Mol. Cell. Biol.* 14:2411 and in Woffendin (1994), *PNAS* 91:1581.

Additionally, the invention provides a method of treating cancer in an individual comprising a) administering to the individual an effective amount of a composition comprising an antibody of the present invention and b) applying a second cancer therapy to the individual. In some embodiments, the second therapy includes surgery, radiation, hormone therapy, gene therapy, other antibody therapy, and chemotherapy. The composition comprising the antibody and the second therapy can be applied concurrently (e.g., simultaneous administration) and/or sequentially (e.g., sequential administration). For example, the composition comprising the antibody and the second therapy are applied with a time separation of no more than about 15 minutes, such as no more than about any of 10, 5, or 1 minutes. Alternatively, the composition comprising the antibody and the second therapy are applied with a time separation of more than about 15 minutes, such as about any of 20, 30, 40, 50, or 60 minutes, 1 day, 2 days, 3 days, 1 week, 2 weeks, or 1 month, or longer.

The composition comprising an antibody of the present invention can be administered sequentially or concurrently with one or more other therapeutic agents such as chemotherapeutic agents (such as 5-FU, 5-FU/MTX, 5-FU/Leucovorin, Levamisole, Irinotecan, Oxaliplatin, Capecitabin, or Uracil/Tegafur), immunoadjuvants, growth inhibitory agents, cytotoxic agents and cytokines, etc. The amounts of the antibody and the therapeutic agent depend on what type of drugs are used, the pathological condition being treated, and the scheduling and routes of administration but would generally be less than if each were used individually.

Following administration of the composition comprising the antibody described herein, the efficacy of the composition can be evaluated both in vitro and in vivo by various methods well known to one of ordinary skill in the art. Various animal models are well known for testing anti-cancer activity of a candidate composition. These include human tumor xenografting into athymic nude mice or scid/scid mice, or genetic murine tumor models such as p53 knockout mice. The in vivo nature of these animal models make them particularly predictive of responses in human patients. Such models can be generated by introducing cells into syngeneic mice using standard techniques, e.g., subcutaneous injection, tail vein injection, spleen implantation, intraperitoneal implantation and implantation under the renal capsule, etc.

Kits

The invention also provides kits for use in the instant methods. Kits of the invention include one or more containers comprising a purified antibody or a polypeptide described herein and instructions for use in accordance with any of the methods of the invention described herein. In some embodiments, these instructions comprise a description of administration of the antibody to treat and/or delay development of a nonhematopoietic cancer, such as colorectal cancer, according to any of the methods described herein. The kit may further comprise a description of selecting an individual suitable for treatment based on identifying whether that individual has the disease and the stage of the disease, or whether the epitope is expressed on the cancer cells in the individual.

In some embodiments, the kits for detecting a cancer cell in a sample comprise an antibody or a polypeptide described herein and reagents for detecting binding of the antibody or the polypeptide to a cell in the sample.

The instructions relating to the use of the antibodies or polypeptides to treat or delay development of cancer generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating a cancer described herein. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an antibody described herein. The container may further comprise a second pharmaceutically active agent.

Kits may optionally provide additional components such as buffers and interpretive information. Normally, the kit comprises a container and a label or package insert(s) on or associated with the container.

EXAMPLES

The following Examples are provided to illustrate but not to limit the invention.

Example 1

Cloning of the Variable Regions of Light and Heavy Chains of 5F1

As shown in U.S. application Ser. No. 11/811,303 filed on Jun. 7, 2007 (published as U.S. Pub. No. 2008/0171043), the variable region cDNAs of 5F1 light and heavy chain variable regions were amplified by PCR, and the synthesized cDNAs were subcloned into pCRII (Invitrogen) for sequence determination. Nucleotide sequences were obtained from several independent clones and analyzed. Identical cDNA sequence from independent clones was chosen to represent the light or heavy chain V region of each antibody. Table 2 below shows the translated amino acid sequences of and nucleotide sequences encoding the light and heavy chain V regions of murine 5F1 (m5F1) and humanized 5F1Vc (h5F1Vc).

TABLE 2

Amino acid sequences of the antibodies' variable regions, and nucleic acid sequences encoding the antibodies' variable regions (CDRs are underlined; signal peptide sequences are in italics.)

m5F1 heavy chain amino acid sequence (SEQ ID NO: 1) and nucleotide sequence (SEQ ID NO: 5)

```
  1   M   E   W   S   W   I   F   L   F   L   L   S   G   T   A   G   V   H   S   E
  1   ATGGAATGGAGTTGGATATTTCTCTTTCTCCTGTCAGGAACTGCAGGTGTCCACTCTGAG

21   V   Q   L   Q   Q   S   G   P   E   L   V   K   P   G   A   S   V   R   M   S
 61   GTCCAGCTGCAGCAGTCTGGACCTGAGCTGGTAAAGCCTGGGGCTTCAGTGAGGATGTCC

41   C   T   A   S   G   Y   T   F   T   S   Y   V   M   H   W   I   K   Q   K   P
121   TGCACGGCTTCTGGATACACATTCACTAGCTATGTTATGCACTGGATAAAGCAGAAGCCT

61   G   Q   G   L   D   W   I   G   Y   I   N   P   Y   N   G   G   T   Q   Y   N
181   GGGCAGGGCCTTGACTGGATTGGATATATTAATCCTTACAATGGTGGTACTCAGTACAAT

81   E   K   F   K   G   K   A   T   L   T   S   D   K   S   S   T   A   Y   M
241   GAGAAGTTCAAAGGCAAGGCCACACTGACTTCAGACAAATCCTCCAGCACAGCCTACATG

101   E   L   S   S   L   T   S   E   D   S   A   V   Y   Y   C   A   R   R   T   F
301   GAGCTCAGCAGCCTGACCTCTGAGGACTCTGCGGTCTATTACTGTGCAAGACGGACCTTC

121   P   Y   Y   F   D   Y   W   G   Q   G   T   T   L   T   V   S   S
361   CCGTACTACTTTGACTACTGGGGCCAAGGCACCACTCTCACAGTCTCCTCA
``` m5F1 light chain amino acid sequence (SEQ ID NO: 2) and nucleotide sequence (SEQ ID NO: 6)

```
  1   M   K   L   P   V   R   L   L   V   L   M   F   W   I   P   A   S   S   S   D
  1   ATGAAGTTGCCTGTTAGGCTGTTGGTGCTGATGTTCTGGATTCCTGCTTCCAGCAGTGAT

21   V   L   M   T   Q   T   P   L   S   L   P   V   S   L   G   D   Q   A   S   I
 61   GTTTTGATGACCCAAACTCCACTCTCCCTGCCTGTCAGTCTTGGAGATCAAGCCTCCATC

41   S   C   R   S   S   Q   S   I   L   H   S   N   G   N   T   Y   L   E   W   Y
121   TCTTGCAGATCTAGTCAGAGCATTTTACATAGTAATGGAAACACCTATTTAGAATGGTAC

61   L   Q   K   P   G   Q   S   P   K   L   L   I   Y   K   V   S   N   R   F   S
181   CTGCAGAAACCAGGCCAGTCTCCAAAGCTCCTGATCTACAAAGTTTCCAACCGATTTTCT

81   G   V   P   D   R   F   S   G   S   G   S   G   T   D   F   T   L   K   I   S
241   GGGGTCCCAGACAGGTTCAGTGGCAGTGGATCAGGGACAGATTTCACACTCAAGATCAGC

101   R   V   E   A   E   D   L   G   V   Y   Y   C   F   Q   G   S   H   A   P   L
301   AGAGTGGAGGCTGAGGATCTGGGAGTTTACTACTGCTTTCAAGGTTCACATGCTCCTCTC

121   T   F   G   A   G   T   K   L   E   L   K
361   ACGTTCGGTGCTGGGACCAAGCTGGAGCTGAAA
``` h5F1Vc heavy chain amino acid sequence (SEQ ID NO: 3) and nucleotide sequence (SEQ ID NO: 7)

```
  1   M   G   W   S   W   I   F   L   F   L   L   S   G   T   A   G   V   H   S   Q
  1   ATGGGATGGAGCTGGATCTTTCTCTTCCTCCTGTCAGGTACCGCGGGCGTGCACTCTCAG

21   V   Q   L   V   Q   S   G   A   E   V   K   K   P   G   S   S   V   K   V   S
 61   GTCCAGCTTGTCCAGTCTGGGGCTGAAGTCAAGAAACCTGGCTCGAGCGTGAAGGTCTCC

41   C   K   A   S   G   Y   T   F   T   S   Y   V   M   H   W   V   R   Q   A   P
121   TGCAAGGCTTCTGGCTACACCTTTACTAGCTATGTTATGCACTGGGTAAGGCAGGCCCCT

61   G   Q   G   L   E   W   I   G   Y   I   N   P   Y   N   G   G   T   Q   Y   N
181   GGACAGGGTCTGGAATGGATTGGATATATTAATCCTTACAATGGTGGTACTCAGTACAAT

81   E   K   F   K   G   K   A   T   I   T   A   D   E   S   T   N   T   A   Y   M
241   GAGAAGTTCAAAGGCAAGGCCACAATTACTGCAGACGAATCCACCAATACAGCCTACATG

101   E   L   S   S   L   T   S   E   D   S   A   V   Y   Y   C   A   R   R   T   F
301   GAACTGAGCAGCCTGACATCTGAGGACAGCGCAGTCTATTACTGTGCAAGACGGACCTTC

121   P   Y   Y   F   D   Y   W   G   Q   G   T   T   L   T   V   S   S
361   CCGTACTACTTTGACTACTGGGGCCAAGGAACCACGCTCACAGTCTCCTCA
```

TABLE 2-continued

Amino acid sequences of the antibodies' variable regions, and nucleic acid sequences encoding the antibodies' variable regions (CDRs are underlined; signal peptide sequences are in italics.)

h5F1Vc light chain amino acid sequence (SEQ ID NO: 4) and nucleotide sequence (SEQ ID NO: 8)

```
  1   M   E   T   D   T   L   L   L   W   V   L   L   L   W   V   P   G   S   T   G
  1  ATGGAGACCGATACCCTCCTGCTATGGGTCCTCCTGCTATGGGTCCCAGGATCAACCGGA

21   D   I   Q   M   T   Q   S   P   S   S   L   S   A   S   V   G   D   R   V   T
 61  GATATTCAGATGACCCAGTCTCCATCTTCCCTCTCTGCTAGCGTCGGGGATAGGGTCACC

41   I   T   C   R   S   S   Q   S   I   L   H   S   N   G   N   T   Y   L   E   W
121  ATAACCTGCAGATCTAGTCAGAGCATTTTACATAGTAATGGAAACACCTATTTAGAATGG

61   Y   Q   Q   K   P   G   K   A   P   K   L   L   I   Y   K   V   S   N   R   F
181  TACCAGCAGAAGCCAGGCAAAGCTCCCAAGCTTCTAATCTATAAAGTTTCCAACCGATTT

81   S   G   V   P   S   R   F   S   G   S   G   S   G   T   D   F   T   L   T   I
241  TCTGGAGTCCCTTCACGCTTCAGTGGCAGTGGATCTGGGACCGATTTCACCCTCACAATC

101   S   S   L   Q   P   D   D   F   A   T   Y   Y   C   F   Q   G   S   H   A   P
301  AGCTCTCTGCAGCCAGATGATTTCGCCACTTATTACTGCTTTCAAGGTTCACATGCTCCT

121   L   T   F   G   Q   G   T   K   V   E   L   K
361  CTCACGTTCGGTCAGGGGACCAAGGTGGAGCTGAAA
```

Example 2

Modified Version of chimeric 5F1 Variants

The isotype of mouse 5F1 antibody is murine IgG3. To obviate the problem of human anti-mouse antibodies (HAMA) response and to have more efficient Fc-dependent functions in humans, a chimeric form of 5F1 (c5F1) antibody (c5F1-v0; for heavy chain: SEQ ID NO.1(VH), NO.9(CH); for light chain SEQ ID NO.2(VL), NO.10(CL), see Table 2 and FIG. 2) was generated by combining the variable (V) region of murine 5F1 antibody with the constant region of human IgG1. The amino acid sequences of heavy chain constant region, which include CH1, hinge, CH2 and CH3 domains, of human IgG1 and murine IgG3, were also compared. From sequence comparison, the CH1-hinge region shows the biggest difference between murine IgG3 and human IgG1 (FIG. 1). As used herein for sequence comparisons, "*" means that the residues in that column are identical in all sequences in the alignment, ":" means that conserved substitutions have been observed, and "." means that semi-conserved substitutions are observed. To have the c5F1 with equivalent apoptosis-inducing activity as that of the murine 5F1, several modifications in the CH1 and/or hinge domains of c5F1 heavy chain were made (Table 3; residue numbering in Table 3 is according to the EU numbering system as described in Burton, Mol. Immunol. 22:161-206, 1985) and several modifications in the C5F1 light chain were made (Table 4). In some cases the modified heavy chain were expressed together with a c-terminal modified light chain (Table 5). See also FIG. 2 for heavy chain and light chain amino acid sequences.

TABLE 3

The modification for v0[H] heavy chain based on human IgG1 constant region.

| Version | CH1 modification | Mutation primer | Amp. primer | Hinge modification | Mutation primer | Amp. primer |
|---------|------------------|-----------------|-------------|--------------------|-----------------|-------------|
| v1 | S131C | M23, M24 | A3, A4 | C220S | M2 | |
| v2 | $^{131}$SSK → CSR | M25, M26 | | | | |
| v3 | $^{129}$APSSKS (SEQ ID NO: 140) → VPGCSD (SEQ ID NO: 141) | M21, M22 | | | | |
| v4 | $^{131}$SSKS (SEQ ID NO: 142) → GCSD (SEQ ID NO: 143) | M19, M20 | | | | |
| v5 | S131C | M23, M24 | A3, A4 | C220S, C226G | M2, M7, A1, A2 | |
| v6 | $^{131}$SSK → CSR | M25, M26 | | | M8 | |
| v7 | S131C | M23, M24 | A3, A4 | C220S, $^{226}$CPP → GSS | M2, M9, | |
| v8 | $^{131}$SSK → CSR | M25, M26 | | | M10 | |
| v9 | S131C | M23, M24 | A3, A4 | C220S, $^{224}$HTCPP (SEQ ID NO: 144) → | M2, M11, | |
| v10 | $^{131}$SSK → CSR | M25, M26 | | | | |

TABLE 3-continued

The modification for v0[H] heavy chain based on human IgG1 constant region.

| Version | CH1 modification | Mutation primer | Amp. primer | Hinge modification | Mutation primer | Amp. primer |
|---------|------------------|-----------------|-------------|--------------------|-----------------|-------------|
| v11 | ¹²⁹APSSKS (SEQ ID NO: 146) → VPGCSD (SEQ ID NO: 147) | M21, M22 | | PPGSS (SEQ ID NO: 145) | M12 | |
| v12 | ¹³¹SSKS (SEQ ID NO: 148) → GCSD (SEQ ID NO: 149) | M19, M20 | | | | |
| v13 | S131C | M23, M24 | A3, A4 | ²¹⁸KSCDKTHTCPP (SEQ ID NO: 150) → RIPKPSTPPGSS (SEQ ID NO: 151) (Replace by mIGg3 hinge) | M13, M14 | |
| v14 | ¹³¹SSK → CSR | M25, M26 | | | | |
| v15 | | | | delete 220C (SD) | M1 | |
| v16 | | | | C220S (SSD) | M2 | |
| v17 | | | | ²¹⁸KSCDK (SEQ ID NO: 152) → KSSCDK (SEQ ID NO: 153) | M15, M16 | A1, A2 |
| v18 | | | | ²¹⁸KSCDK (SEQ ID NO: 154) → KCSDK (SEQ ID NO: 155) | M17, M18 | |
| v19 | | | | ²¹⁸KSCDK (SEQ ID NO: 156) → KSDKSCDK (SEQ ID NO: 157) | M3, M4 | |
| v20 | | | | ²¹⁸KSCDK (SEQ ID NO: 158) → KSCDKSDK (SEQ ID NO: 159) | M5, M6 | |

TABLE 4

The modifications for v0[L] light chain constant region based on human IgG1 kappa chain

| Version | LC: kappa modification | Mutation primer | Amp. primer |
|---------|------------------------|-----------------|-------------|
| v0[L] | PVTKSFNRGEC (SEQ ID NO: 160) | | A5, A6 |
| v21 | PVTKSFNRGEGEC (SEQ ID NO: 161) | M35, M36 | |
| v22 | PVTKSFNRGGEGEC (SEQ ID NO: 162) | M37, M38 | |
| v23 | PVTKSFNRGGGEGEC (SEQ ID NO: 163) | M39, M40 | |
| v24 | PVTKSFNRGGEC (SEQ ID NO: 164) | M33, M34 | |
| v25 | PVTKSFNRGGGEC (SEQ ID NO: 165) | M31, M32 | |
| v26 | PVTKSFNRGGGGEC (SEQ ID NO: 166) | M29, M30 | |
| v27 | PVTKSFNRGGGGGEC (SEQ ID NO: 167) | M27, M28 | |

TABLE 5

Chimeric antibodies comprising the combination of modified heavy and/or light chain constant regions

| Antibodies | Heavy chain | Light chain |
|------------|-------------|-------------|
| c5F1-v0 | v0[H] | v0[L] |
| c5F1-v1 | v1 | v0[L] |
| c5F1-v2 | v2 | v0[L] |
| c5F1-v3 | v3 | v0[L] |
| c5F1-v4 | v4 | v0[L] |
| c5F1-v5 | v5 | v0[L] |
| c5F1-v6 | v6 | v0[L] |
| c5F1-v7 | v7 | v0[L] |
| c5F1-v8 | v8 | v0[L] |
| c5F1-v9 | v9 | v0[L] |
| c5F1-v10 | v10 | v0[L] |
| c5F1-v11 | v11 | v0[L] |
| c5F1-v12 | v12 | v0[L] |
| c5F1-v13 | v13 | v0[L] |
| c5F1-v14 | v14 | v0[L] |
| c5F1-v15 | v15 | v0[L] |
| c5F1-v16 | v16 | v0[L] |
| c5F1-v17 | v17 | v0[L] |
| c5F1-v18 | v18 | v0[L] |
| c5F1-v19 | v19 | v0[L] |
| c5F1-v20 | v20 | v0[L] |
| c5F1-v21 | v19 | v21 |
| c5F1-v22 | v19 | v22 |
| c5F1-v23 | v19 | v23 |

TABLE 5-continued

Chimeric antibodies comprising the combination of modified heavy and/or light chain constant regions

| Antibodies | Heavy chain | Light chain |
| --- | --- | --- |
| c5F1-v24 | v19 | v24 |
| c5F1-v25 | v19 | v25 |
| c5F1-v26 | v19 | v26 |
| c5F1-v27 | v19 | v27 |

Example 3

Introduction of Changes in the Constant Regions of Heavy and Light Chain of the Chimeric 5F1 Antibody To facilitate antibody production and purification, pcDNA5-FRT-hIgG1 (generated at AbGenomics) which contains the constant regions of human IgG1 heavy chain and kappa light chain, was used to express chimeric 5F1 (c5F1). The variable regions of m5F1 heavy chain and light chain genes were amplified separately by PCR using primer pairs of m5F1HC-XbaI f/m5F1HC-XbaI r and m5F1LC-XbaI f/m5F1LC-XbaI r (Table 6, primers A3/A7 and A8/A9), respectively. The PCR products were digested by XbaI and sequentially inserted into pcDNA5-FRT-hIgG1. The completely assembled c5F1 expression plasmid c5F1/pcDNA5-FRT-hIgG1, containing both the heavy chain gene and light chain gene of c5F1, was used to express non-modified c5F1 antibody. The same plasmid was also used as the template for the introduction of c5F1 modification.

PCR-based site-directed mutagenesis with primers (Table 6) introducing mutations into the genes of c5F1/pcDNA5-FRT-hIgG1 was used to generate the constructs with deletion (v15) or S substitution (v16) at residue 220 (Eu numbering), using QuikChange Multi Site Directed Mutagenesis Kit (Stratagene, Cat#200531-5) following manufacturer's instruction. The oligonucletide M1(5'-CAGAGC-CCAAATCTGACAAAACTCACAC-3' (SEQ ID NO:47)) was used to delete Cys at residue 220 (v15), and the oligonucletide M2 (5'-CAGAGCCCAAATCTTCTGA-CAAAACTCACAC-3' (SEQ ID NO:48)) was used to make Ser substitution at residue 220(v16). To obviate the possibility of random mutations introduced by PCR during site-directed mutagenesis, the DNA fragments containing modification were excised with AgeI (within CH1 region) and XmaI (within CH3 region), and re-cloned into original c5F1/pcDNA5-FRT-hIgG1, to replace the original unmodified regions.

Alternatively, over-lapping PCR was also used to generate all the rest modifications (Table 3-6). In brief, two PCR reactions were used to generate two fragments of DNA products which contain the desired mutations, and which share an over-lapping sequence of at least 20 nucleotides. The two PCR products are then mixed, denatured and allowed to re-anneal. Another PCR reaction with the two outer primers (from the previous two PCR) was then used to amplify the assembled, full length DNA fragment. For example, for v1, primer pairs A4/M23 and M24/A3 (Table 6) were used to generate the first two fragments by PCR. The two PCR fragments were then mixed, re-annealed, and the outer primer (A3 and A4) was used to generate the full length PCR product. Finally, the DNA fragments containing modification were re-cloned into original c5F1/pcDNA5-FRT-hIgG1. Fragment containing CH1 modification was re-cloned via XbaI (within beginning of heavy chain V region) and AgeI (within CH1 region) sites. Fragment containing Hinge modification was re-cloned via AgeI (within CH1 region) and XmaI (within CH3 region) sites. For making c-terminal modification of light chain, the PCR products were cloned via AvrII (within end of light chain V region) and BamHI (within downstream of light chain coding sequence) sites, to replace the original unmodified sequences.

The plasmids with or without modification were then transfected into Flp-In-CHO cells (Invitrogen, Cat no. R758-07) by lipofetamine 2000 (Invitrogen, Cat no. 11668-019). The culture medium containing unmodified or modified c5F1 antibodies were collected, and the antibody purified by Protein A. The purified antibody was tested for the binding and apoptosis-inducing activity in COL0205 cells.

Binding Assay

Purified m5F1, c5F1-v0, c5F1-v15 and c5F1-v16 antibodies at the concentration ranging from 0.125 to 4 ug/ml were added to $1.5 \times 10^5$ COLO 205 cells and incubated for 30 min at 4° C., washed for twice with PBS containing 2% FBS and 0.05% $NaN_3$, followed by incubation with 1 µg/ml of corresponding secondary antibodies (R-PE-conjugated goat F(ab')2 anti-mouse IgG(H+L), Southern Biotech, Cat. No. 1032-09; or R-PE-conjugated goat anti-human IgG, Southern Biotech, Cat. No. 2040-09) at 4° C. for 30 min. At the end of staining, samples were washed twice with PBS containing 2% FBS and 0.05% $NaN_3$ and analyzed by flow cytometer. All flow cytometric analyses were performed on a BD-LSR flow cytometer (Becton Dickinson) using the Cell Quest software.

Apoptosis Assay $1.5 \times 10^5$ of COLO 205 cells were seeded into the wells of 96-well plates. Aliquots of purified m5F1, c5F1-v0, c5F1-v15, c5F1-v16 and control antibodies at the concentration ranging from 2 to 32 ug/ml were prepared freshly in culture medium and added to each well. The sample treated with m9E10 and h16C11A were used as isotype control. The treated cells were kept at 37° incubator for 6 h before FACS analysis for apoptosis. For cellular apoptosis assay, Annexin V staining was measured using Annexin-V-FITC Apoptosis Detection Kit (Strong Biotech, Cat. No. AVK250) following the manufacturer's instruction. In brief, the treated cells were harvested and resuspended in Annexin V binding buffer containing Annexin V-FITC at room temperature. After 15 min incubation in the dark, the cells were washed twice with 200 µl of Annexin V binding buffer. Before FACS analysis, 0.25 µg/ml of propidium iodide (PI) was added. All flow cytometric analyses were performed on a BD-LSR flow cytometer (Becton Dickinson) using the Cell Quest software. The Annexin VI positive and/or PI positive cells are considered apoptotic cells.

TABLE 6

Primers used for introducing mutations in c5F1 gene

| PRIMER NAME | PRIMER SEQUENCE (5' → 3') | SEQ ID NO |
| --- | --- | --- |
| (A1) hIgG1 CH1 f | ACCACCTCTCTTGCAGCCTC | SEQ ID NO: 38 |
| (A2) hIgG1 CH3 r | CATTGCTCTCCCACTCAC | SEQ ID NO: 39 |
| (A3) m5F1HC-XbaI f | TCTATCTAGATGGAATGGAGTTGGATATTTCTCTTTC | SEQ ID NO: 40 |

TABLE 6-continued

Primers used for introducing mutations in c5F1 gene

| PRIMER NAME | PRIMER SEQUENCE (5' → 3') | SEQ ID NO |
|---|---|---|
| (A4) hIgG1 intron r | ATATGGCTCTTGGCAGGTCT | SEQ ID NO: 41 |
| (A5) pcDNA5FRT-hG1LC 3' BamHI/BglII-r | GGGAGATCTGGATCCTAGAAG | SEQ ID NO: 42 |
| (A6) m5F1 LC AvrII-f | TAATCCTAGGAATTCTAAACTCTG | SEQ ID NO: 43 |
| (A7) m5F1HC-XbaI r | ACCCTCTAGAGGTTGTGAGGACTCACCTGAGGAGACTGTGAGAGTGGTGCC | SEQ ID NO: 44 |
| (A8) m5F1LC-XbaI f | TCTATCTAGATGAAGTTGCCTGTTAGGCTG | SEQ ID NO: 45 |
| (A9) m5F1LC-XbaI r | ACCCTCTAGAATTAGGAAAGTGCACTTACGTTTCAGCTCCAGC | SEQ ID NO: 46 |
| (M1) hIgG1 hinge d220C-f (v15) | CAGAGCCCAAATCTGACAAAACTCACAC | SEQ ID NO: 47 |
| (M2) hIgG1 hinge C220S-f (v16) | CAGAGCCCAAATCTTCTGACAAAACTCACAC | SEQ ID NO: 48 |
| (M3) hIgG1 hinge KSD f (v19) | GAGCCCAAATCTGACAAATCTTGTGACAAAACTCACAC | SEQ ID NO: 49 |
| (M4) hIgG1 hinge KSD r (v19) | GATTTGTCAGATTTGGGCTCTGCAGAGAAGATTGG | SEQ ID NO: 50 |
| (M5) hIgG1 hinge SDK f (v20) | TGTGACAAATCTGACAAAACTCACACATGCCCACCGTGCC | SEQ ID NO: 51 |
| (M6) hIgG1 hinge SDK r (v20) | GTTTTGTCAGATTTGTCACAAGATTTGGGCTCTGCAGAGAG | SEQ ID NO: 52 |
| (M7) hIgG1 hinge C226G f | AACTCACACAGGTCCACCGTGCCCAGGTAAGCCAGCCCAG | SEQ ID NO: 53 |
| (M8) hIgG1 hinge C226G r | CACGGTGGACCTGTGTGAGTTTTGTCAGAAGATTTGGGCT | SEQ ID NO: 54 |
| (M9) hIgG1 hinge 226CPP → GSS f | CACACAGGTTCTTCATGCCCCAGGTAAGCCAGCCCACGCCT | SEQ ID NO: 55 |
| (M10) hIgG1 hinge 226CPP → GSS r | GGGCATGAAGAACCTGTGTGAGTTTTGTCAGAAGATTTGG | SEQ ID NO: 56 |
| (M11) hIgG1 hinge 224HTCPP → PPGSS f | CTCCCCCAGGTTCTTCATGCCCAGGTAAGCCAGCCCAGGC | SEQ ID NO: 57 |
| (M12) hIgG1 hinge 224HTCPP→PPGSS r | GCATGAAGAACCTGGGGGAGTTTTGTCAGAAGATTTGGGC | SEQ ID NO: 58 |
| (M13) hIgG1 hinge mIgG3 r 218KSCDKTHTCPP → RIPKPSTPPGSS) | CTGGGGGGTACTGGGCTTGGGTATTCTGGGCTCTGCAGAGAAGATT | SEQ ID NO: 59 |
| (M14) hIgG1 hinge mIgG3 f (218KSCDKTHTCPP → RIPKPSTPPGSS) | CAAGCCCAGTACCCCCCCAGGTTCTTCATGCCCAGGTAAGCCAGCCCAG | SEQ ID NO: 60 |
| (M15) hIgG1 hinge 218KSCDK → KSSCDK f (v17) | AGCCCAAATCTTCTTGTGACAAAACTCACAC | SEQ ID NO: 61 |
| (M16) hIgG1 hinge 218KSCDK → KSSCDK r (v17) | GTCACAAGAAGATTTGGGCTCTGCAGAGAA | SEQ ID NO: 62 |
| (M17) hIgG1 hinge 218KSCDK → KCSDK f (v18) | GCCCAAATGTTCTGACAAAACTCACACATGCCC | SEQ ID NO: 63 |
| (M18) hIgG1 hinge 218KSCDK → KCSDK r (v18) | TTTTGTCAGAACATTTGGGCTCTGCAGAGAA | SEQ ID NO: 64 |
| (M19) hIgG1 CH1 (131SSKS → GCSD) r | AGGTGTCACTGCAGCCGGGTGCCAGGGGGAAGACCGAT | SEQ ID NO: 65 |
| (M20) hIgG1 CH1 (131SSKS → GCSD) f | ACCCGGCTGCAGTGACACCTCTGGGGGCACAGCGGCCC | SEQ ID NO: 66 |
| (M21) hIgG1 CH1 (129APSSKS → VPGCSD) r | TGTCACTGCAGCGGGGACCAGGGGGAAGACCGATGGGC | SEQ ID NO: 67 |
| (M22) hIgG1 CH1 (129APSSKS → VPGCSD) f | GGTCCCCGGCTGCAGTGACACCTCTGGGGCACAGCGGC | SEQ ID NO: 68 |
| (M23) hIgG1 CH1 S131C f | CCTGGCACCCTGCTCCAAGAGCACCTCTGGGGGCACA | SEQ ID NO: 69 |
| (M24) hIgG1 CH1 S131C r | AGGTGCTCTTGGAGCAGGGTGCCAGGGGGAAGACCGAT | SEQ ID NO: 70 |
| (M25) hIgG1 CH1 131SSK → CSR f | CCTGGCACCCTGCTCCAGGAGCACCTCTGGGGGCACAGCG | SEQ ID NO: 71 |
| (M26) hIgG1 CH1 131SSK → CSR r | CAGAGGTGCTCCTGGAGCAGGGTGCCAGGGGGAAGACCGA | SEQ ID NO: 72 |
| (M27) LC_GGGG-r | CACTCTCCACCACCTCCTCCCCTGTTGAAGCTCTTTG | SEQ ID NO: 73 |
| (M28) LC_GGGG-f | GGGGAGGAGGTGGTGGAGAGTGTTAGAGGGAGAAGTG | SEQ ID NO: 74 |
| (M29) LC_GGG-r | ACACTCTCCACCTCCTCCCCTGTTGAAGCTCTTTG | SEQ ID NO: 75 |
| (M30) LC_GGG-f | AGGGGAGGAGGTGGAGAGTGTTAGAGGGAGAAGTG | SEQ ID NO: 76 |
| (M31) LC_GG-r | AACACTCTCCTCCTCCCCTGTTGAAGCTCTTTG | SEQ ID NO: 77 |
| (M32) LC_GG-f | CAGGGGAGGAGGAGAGTGTTAGAGGGAGAAGTG | SEQ ID NO: 78 |

TABLE 6-continued

Primers used for introducing mutations in c5F1 gene

| PRIMER NAME | PRIMER SEQUENCE (5' → 3') | SEQ ID NO |
|---|---|---|
| (M33) LC_G-r | AACACTCTCCTCCCCTG TTGAAGCTCTTTG | SEQ ID NO: 79 |
| (M34) LC_G-f | CAGGGGAGGAGAGTGTT AGAGGGAGAAGTG | SEQ ID NO: 80 |
| (M35) LC_GE-r | AACACTCTCCCTCTCCC CTGTTGAAGCTCTTTG | SEQ ID NO: 81 |
| (M36) LC_GE-f | CAGGGGAGAGGGAGAGT GTTAGAGGGAGAAGTG | SEQ ID NO: 82 |
| (M37) LC_GGE-r | CACTCTCCCTCACCTCCC CTGTTGAAGCTCTTTGTG | SEQ ID NO: 83 |
| (M38) LC_GGE-f | CAGGGGAGGTGAGGGAG AGTGTTAGAGGGAGAAG | SEQ ID NO: 84 |
| (M39) LC_GGGE-r | CACTCTCCCTCACCACC TCCCCTGTTGAAGCTCT TTGTG | SEQ ID NO: 85 |
| (M40) LC_GGGE-f | CAGGGGAGGTGGTGAGG GAGAGTGTTAGAGGGAG AAG | SEQ ID NO: 86 |

Result

The binding and apoptosis-inducing effects of variant 5F1 antibodies from flow cytometric analysis are shown in FIG. 3 and Table 7 below. c5F1-v0, c5F1-v15 and c5F1-v16 bind COLO 205 cells and induce apoptosis in COLO 205 cells, just as their mouse counterpart m5F1. c5F1-v15 and c5F1-v16 bind to COL0205 cells relatively less compared to c5F1. For apoptosis induction, the effect observed in c5F1-v0 treated cells was not as efficient as m5F1. However, when the hinge modified forms (c5F1-yl5 and c5F1-v16) were used, the apoptosis-inducing activity was restored. Both c5F1-yl5 and c5F1-v16 induced apoptosis in COLO205 cells almost as efficient as m5F1, despite that the binding activity of c5F1-yl5 and c5F1-v16 to COLO 205 cells seemed to be lower than that of c5F1-v0. The isotype control antibodies 9E10 (mouse Ig control) and h16C11A (human Ig control) at 32 ug/ml did not induce apoptosis in COLO 205 cells.

TABLE 7

Six-hour apoptosis assay by 5F1 antibodies in COLO 205

| (ug/ml) | 2 | 4 | 8 | 16 | 32 |
|---|---|---|---|---|---|
| m5F1 | 35 | 53 | 76 | 92 | 93 |
| c5F1 v0 | | 33 | 46 | 68 | 78 |
| c5F1 v15 | | 64 | 82 | 93 | 96 |
| c5F1 v16 | | 58 | 78 | 92 | 96 |
| m9E10 | | | | | 23 |
| h16C11A | | | | | 25 |

(% of Annexin V and/or PI positive cells)

Example 4

Humanization of 5F1 Antibodies

Humanized version of 5F1 are also developed (FIG. 4) and incorporated into the expression plasmids with constant region modifications (see Example 2 and 3).

Complementarity-determining region (CDR) grafting was used to generate the variable region of humanized 5F1 (h5F1M), in which the CDRs of mouse 5F1 variable region was incorporated into a framework of a human IgG1 variable region (the acceptor antibody) by recombinant DNA technology. To determine the best fit acceptor antibody for murine 5F1, the sequences of the variable region of murine 5F1 was analyzed together with the immunoglobulin database generated in AbGenomics. Murine antibody M195 (Man Sung Co et al. *J. Immunol.* 148(4):1149-1154 (Feb. 15, 1992)) showed best-fit for murine 5F1. Human antibody Eu (Man Sung Co et al. *J. Immunol.* 148(4):1149-1154 (Feb. 15, 1992)) was in consequence selected as the acceptor antibody. Nucleotide sequences were designed and synthesized to generate a humanized 5F1 version with the three CDR regions of murine 5F1 incorporated into the framework of the variable regions of antibody Eu.

To engineer each V gene of h5F1M, four pairs oligonucleotides of 55-70 bases in length, which sequentially share overlapping regions of at least 18 nucleotides, were synthesized (Table 8. For heavy chain:H1-H8, for light chain:L1-L8). The assembly and amplification of the entire V genes were conducted in four steps: 1) the four pairs of complementary oligonucleotides (for heavy chain:H1/H2, H3/H4, H5/H6 and H7/H8; for light chain: L1/L2, L3/L4, L5/L6 and L7/L8) were annealed and the 3' recess regions were filled in with Klenow fragment in separate reactions to generate four double stranded DNA(dsDNA) fragments; 2) the resulting four dsDNA fragments were mixed pairwise, denatured, re-annealed, and the 3' recess filled in two separate reactions to generate two dsDNA fragments; 3) the resulting two dsDNA fragments were mixed, denatured, re-annealed, and the 3' recess filled in to create the full length dsDNA; and 4) PCR reaction with two outer primers (for heavy chain: A10 and A11, for light chain: A12 and A13 (Table 8), which contain the XbaI site, was then used to amplify the assembled VL and VH fragments.

The XbaI-containing VH and VL fragments were then inserted into pcDNA5-FRT-hIgG1vector via NheI site and AvrII site for heavy chain and light chain, respectively. The completely assembled h5F1M expression plasmid h5F1M/pcDNA5-FRT-hIgG1, containing both the heavy chain and light chain gene of h5F1M, was used to express non-modified h5F1M antibody. The same plasmid was also used as the template for the introduction of h5F1M modifications (FIG. 4).

The Modification of h5F1-M.

Overlapping PCR and PCR-based site-directed mutagenesis are used to modify the variable region of h5F1-M (FIG. 4) using primers listed in Table 8 and 9. The h5F1 variable regions, unmodified or modified, are incorporated to human IgG constant region (unmodified or modified) as mentioned in Example 2-3. The expression plasmids are then transfected into CHO cells. The supernatants are collected and the antibodies purified by protein A. The purified antibodies are tested for the binding and apoptosis-inducing function in COL0205 cells.

TABLE 8

| The list of the primers used in the engineering of variants of humanized 5F1 antibodies. | | |
|---|---|---|
| PRIMER NAME | PRIMER SEQUENCE (5' → 3') | SEQ ID NO |
| (A10) 5F1MH-A (65 mer) | TCTATCTAGATGGGATGGAGCT GGATCTTTCTCTTCCTCCTGTC AGGTACCGCGGGCGTGCACTC | SEQ ID NO: 97 |

TABLE 8-continued The list of the primers used in the engineering of variants of humanized 5F1 antibodies.

| PRIMER NAME | PRIMER SEQUENCE (5' → 3') | SEQ ID NO |
|---|---|---|
| (A11) 5F1MH-B (56 mer) | ACCCTCTAGAGGTTGTGAGGACTCACCTGAGGAGACTGTGACCAGGGTTCCTTGGC | SEQ ID NO: 98 |
| (H1) 5F1MH-1f (69 mer) | GTCAGGTACCGCGGGCGTGCACTCTCAGGTCCAGCTTGTCCAGTCTGGGGCTGAAGTCAAGAAACCTGG | SEQ ID NO: 99 |
| (H2) 5F1MH-2r (66 mer) | AGTAAAGGTGTAGCCAGAAGCCTTGCAGGAGACCTTCACGCTCGAGCCAGGTTTCTTGACTTCAGC | SEQ ID NO: 100 |
| (H3) 5F1MH-3f (67 mer) | GCTTCTGGCTACACCTTTACTAGCTATGTTATGCACTGGGTAAGGCAGGCCCCTGGACAGGGTCTGG | SEQ ID NO: 101 |
| (H4) 5F1MH-4r (66 mer) | TTGTACTGAGTACCACCATTGTAAGGATTAATATATCCAATCCATTCCAGACCCTGTCCAGGGGCC | SEQ ID NO: 102 |
| (H5) 5F1MH-5f (62 mer) | ATGGTGGTACTCAGTACAATGAGAAGTTCAAAGGCAAGGCCACAATTACTGCAGACGAATCC | SEQ ID NO: 103 |
| (H6) 5F1MH-6r (63 mer) | CCTCAGATCTCAGGCTGCTCAGTTCCATGTAGGCTGTATTGGTGGATTCGTCTGCAGTAATTG | SEQ ID NO: 104 |
| (H7) 5F1MH-7f (64 mer) | GAGCAGCCTGAGATCTGAGGACACCGCAGTCTATTACTGTGCAAGACGGACCTTCCCGTACTAC | SEQ ID NO: 105 |
| (H8) 5F1MH-8r (60 mer) | TGAGGAGACTGTGACCAGGGTTCCTTGGCCCCAGTAGTCAAAGTAGTACGGGAAGGTCCG | SEQ ID NO: 106 |
| (A12) 5F1ML-A (59 mer) | TCTATCTAGATGGAGACCGATACCCTCCTGCTATGGGTCCTCCTGCTATGGGTCCCAGG | SEQ ID NO: 107 |
| (A13) 5F1ML-B (58 mer) | ACCCTCTAGAATTAGGAAAGTGCACTTACGTTTCAGCTCCACCTTGGTCCCCTGACCG | SEQ ID NO: 108 |
| (L1) 5F1ML-1f (62 mer) | TCCTGCTATGGGTCCCAGGATCAACCGGAGATATTCAGATGACCCAGTCTCCATCTTCCCTC | SEQ ID NO: 109 |
| (L2) 5F1ML-2r (60 mer) | GATCTGCAGGTTATGGTGACCCTATCCCCGACGCTAGCAGAGAGGAAGATGGAGACTGG | SEQ ID NO: 110 |
| (L3) 5F1ML-3f (64 mer) | CACCATAACCTGCAGATCTAGTCAGAGCATTTTACATAGTAATGGAAACACCTATTTAGAATGG | SEQ ID NO: 111 |
| (L4) 5F1ML-4r (60 mer) | GATTAGAAGCTTGGGAGCTTTGCCTGGCTTCTGCTGGTACCATTCTAAATAGGTGTTTCC | SEQ ID NO: 112 |
| (L5) 5F1ML-5f (66 mer) | GCTCCCAAGCTTCTAATCTATAAAGTTTCCAACCGATTTTCTGGAGTCCCTTCACGCTTCAGTGGC | SEQ ID NO: 113 |
| (L6) 5F1ML-6r (61 mer) | GCAGAGAGCTGATTGTGAGGGTGAAATCGGTCCCAGATCCACTGCCACTGAAGCGTGAAGG | SEQ ID NO: 114 |
| (L7) 5F1ML-7f (56 mer) | CTCACAATCAGCTCTCTGCAGCCAGATGATTTCGCCACTTATTACTGCTTTCAAGG | SEQ ID NO: 115 |
| (L8) 5F1ML-8r (63 mer) | CCACCTTGGTCCCCTGACCGAACGTGAGGAGCATGTGAACCTTGAAAGCAGTAATAAGTGG | SEQ ID NO: 116 |
| (A14) h5F1AL C-B r (58 mer) | ACCCTCTAGAATTAGGAAAGTGCACTTACGTTTGATCTCCACCTTGGTCCCCTGACCG | SEQ ID NO: 117 |
| (M41) h5F1A/M/D HC-R106T, T110S f | GCAGCCTGACATCTGAGGACAGCGC | SEQ ID NO: 118 |
| (M42) h5F1A/M/D HC-R106T, T1110S r | GACTGCGCTGTCCTCAGATGTCAGGCTGCTCAGTTCCATG | SEQ ID NO: 119 |
| (M43) h5F1M HC E93T-r | TTGGTGGATGTGTCTGCAGTAATTGTGGCCT | SEQ ID NO: 120 |
| (M44) h5F1M HC E93T-f | ACTGCAGACACATCCACCAATACAGCCTACA | SEQ ID NO: 121 |
| (M45) h5F1M LC Fw3-r | TCCCAGATCCTCAGCCTCCACTCTGCTGATCTTGAGGGTGAAATCGGTCCCA | SEQ ID NO: 122 |
| (M46) h5F1M LC Fw3-f | AGAGTGGAGGCTGAGGATCTGGGAACTTATTACTGCTTTCAAGG | SEQ ID NO: 123 |
| (M47) h5F1A-HC A95S-f | GACACATCCTCCAGTACAGCCTACATGGAA | SEQ ID NO: 124 |
| (M48) h5F1A-HC A95S-r | GCTGTACTGGAGGATGTGTCTGAAGTAATTG | SEQ ID NO: 125 |
| (M49) h5F1A LC Fw3-r | TCCCAGATCTTCAGCCTCCACTCTGCTGATCTTGAGGGTGAAATCGGTCCCAGATC | SEQ ID NO: 126 |
| (M50) h5F1A LC Fw3-f | AGAGTGGAGGCTGAAGATCTGGGAACTTATTACTGCTTTCAAGG | SEQ ID NO: 127 |
| (M51) h5F1A HC-S35A f | GTCAAGAAACCTGGCGCGAGCGTGAAGGTC | SEQ ID NO: 128 |
| (M52) h5F1A HC-K86R, A87V f | CAAAGGCAGGGTCACAATTACTGCAGACGAATC | SEQ ID NO: 129 |
| (M53) h5F1A HC-K86R, A87V r | TAATTGTGACCCTGCCTTTGAACTTCTCATTG | SEQ ID NO: 130 |
| (M54) h5F1A HC-A91S, E93T, T95A, N96S f | TTCAGACACATCCGCCAGTACAGCCTACATGGAACTGAG | SEQ ID NO: 131 |
| (M55) h5F1A HC-A91S, E93T, T95A, N96S r | TACTGGCGGATGTGTCTGAAGTAATTGTGACCCTGCCTTTG | SEQ ID NO: 132 |
| (M56) h5F1A HC-G63R, I67M f | AGCGTCTGGAATGGATGGGATATATTAATCCTTACAA | SEQ ID NO: 133 |
| (M57) h5F1A HC-G63R, I67M r | TCCCATCCATTCCAGACGCTGTCCAGGGGCCTGCCTTA | SEQ ID NO: 134 |

TABLE 8-continued

The list of the primers used in the engineering of variants of humanized 5F1 antibodies.

| PRIMER NAME | PRIMER SEQUENCE (5' → 3') | SEQ ID NO |
|---|---|---|
| (M58) h5F1A LC-L98F f | GGACCGATTTCACCTTCACAAT CAGCTCTC | SEQ ID NO: 135 |
| (M59) h5F1A LC-D106E, F107I f | CAGCCAGAAGATATCGCCACTT ATTACTGCTTT | SEQ ID NO: 136 |
| (M60) h5F1A LC-D106E, F107I r | GTGGCGATATCTTCTGGCTGCA GAGAGCTGAT | SEQ ID NO: 137 |

TABLE 9

The primers for modifying h5F1M.

| | VH | | VL | |
|---|---|---|---|---|
| | Mutation primer | Amplification primer | Mutation primer | Amplification primer |
| h5F1M Va | M41/M42 | A10/A11 | — | — |
| h5F1M Vs | M41/M42, M43/M44 | A10/A11 | M45/M46 | A12/A13 |
| h5F1A Va | M41/M42, M51, M52/M53, M54/M55, M56/M57, | A10/A11 | M58, M59/M60 | A12/A14 |
| h5F1A Vs | M51, M52/M53, M54/M55, M56/M57, M41/M42, M47/M48 | A10/A11 | M58, M59/M60, M49/M50 | A12/A14 |

Example 5

Characterization of Chimeric 5F1 Variants

Binding of Antibodies to Colo205 Cells

Purified m5F1, c5F1-v0, c5F1-yl7, c5F1-v24 and c5F1-v25 antibodies at 1 ug/ml were added to 2×10$^5$ Colo 205 cells and incubated for 30 min at 4° C., washed for twice with PBS containing 1% FBS, followed by incubation with 1 ug/ml of corresponding secondary antibodies (R-PE-conjugated goat F(ab')2 anti-mouse IgG(H+L), Southern Biotech, Cat. No. 1032-09; or R-PE-conjugated goat anti-human IgG, Southern Biotech, Cat. No. 2040-09) at 4° C. for 30 min. At the end of staining, samples were washed twice with PBS containing 1% FBS and 0.05% NaN$_3$ and analyzed by flow cytometer. All flow cytometric analyses were performed on a BD-LSR flow cytometer (Becton Dickinson) using the Cell Quest software. The data in Table 10 indicated that all the tested versions of 5F1 antibodies could bind to Colo205 cells.

TABLE 10

Binding to Colo205 cells

| Antibodies | Median Fluorescence Intensity (MFI) |
|---|---|
| mIgG3 | 7 |
| m5F1 | 800 |
| hIgG1 | 6 |
| c5F1v0 | 2760 |
| c5F1v17 | 2303 |
| c5F1v24 | 3134 |
| c5F1v25 | 3174 |

Apoptosis Assay 1.5×10$^5$ of Colo205 cells were seeded into the wells of 96-well plates. Aliquots of purified m5F1, c5F1, c5F1-v17, c5F1-v24, c5F1-v25 and control antibodies at the concentration ranging from 8 to 32 ug/ml were prepared freshly in culture medium and added to each well. The treated cells were kept at 37° incubator for 6 h before FACS analysis for apoptosis. For cellular apoptosis assay, Annexin V staining was measured using Annexin-V-FITC Apoptosis Detection Kit (Strong Biotech, Cat. No. AV 250) following the manufacturer's instruction. In brief, the treated cells were harvested and resuspended in Annexin V binding buffer containing Annexin V-FITC at room temperature. After 15 min incubation in the dark, the cells were washed twice with 200 ul of Annexin V binding buffer. Before FACS analysis, 0.25 ug/ml of propidium iodide (PI) was added. All flow cytometric analyses were performed on a BD-LSR flow cytometer (Becton Dickinson) using the Cell Quest software. The Annexin VI positive and/or PI positive cells are considered apoptotic cells. The data in Table 11 showed all the tested versions of 5F1 antibodies could induce apoptosis in Colo205 cells.

TABLE 11

(a, b). Apoptosis inductions in Colo205 cells.

| | 8 ug/ml | 16 ug/ml | 32 ug/ml |
|---|---|---|---|
| (a) Exp. 1. | | | |
| m5F1 | 88 | 92 | 92 |
| c5F1v0 | 34 | 60 | 70 |
| c5F1v24 | 33 | 52 | 62 |
| c5F1v25 | 26 | 43 | 50 |
| mIgG1 | | | 17 |
| hIgG1 | | | 18 |
| (b) Exp. 2 | | | |
| m5F1 | 89 | 94 | 96 |
| c5F1v0 | 54 | 63 | 69 |
| c5F1v17 | 51 | 56 | 60 |
| mIgG1 | | | 26 |
| hIgG1 | | | 27 |

(% of Annexin V and/or PI positive cells)

Xenograft Study

5×10$^6$ Colo205 cells were implanted subcutaneously into the hind flank region of 6-7 week-old SCID mice on day 0. Treatment with intraperitoneal injection of antibodies at 30 mg/kg started on day 0 after tumor-cell inoculation and was repeated on days 4, 7, 11, 14, and 18. Six mice were used in each group of the experiment. Tumor growth was assessed based on twice-weekly measurement of tumor volume (mm$^3$)

by calipers and the tumor size was calculated using the formula: $\pi/6 \times$larger diameter$\times$(smaller diameter)$^2$ (Kievit E, Cancer Research, 60:6649-55). Mice were sacrificed on day 21 and the tumors were isolated and the weight measured. The results shown in Table 12 indicated that anti-tumor effects of all antibodies tested compared to PBS treatment.

TABLE 12

Xenograft study.

| | Tumor size (mm$^3$) | Tumor weight (g) |
|---|---|---|
| PBS | 521.695 ± 129.006 | 0.3228 ± 0.0707 |
| c5F1v17 (30 mg/kg × 6) | 169.698 ± 68.798* | 0.0925 ± 0.0360* |
| c5F1v24 (30 mg/kg × 6) | 44.108 ± 37.382* | 0.0170 ± 0.0154* |
| c5F1v25 (30 mg/kg × 6) | 111.093 ± 56.051* | 0.0682 ± 0.0320* |

*P < 0.01 compared to PBS treatment on Day 21 (Student's t-test).

Synergistic Effect of 5F1 Antibodies in Combination with Oxaliplatin in Inducing Apoptosis of Colo205 Cells $1.4 \times 10^5$ of Colo205 cells were seeded into the wells of 96-well plates. Aliquots of Oxaliplatin reconstituted in 5% glucose solution were prepared freshly and added to each well at the final concentration of 1 and 10 ug/ml, along or in combination with aliquots of purified c5F1-v17, c5F1-v24, c5F1-v25 and control antibodies at the final concentrations of 10 and 30 ug/ml. The treated cells were kept at 37° incubator for 24 h before FACS analysis for apoptosis. For cellular apoptosis assay, Annexin V staining was measured using Annexin-V-FITC Apoptosis Detection Kit (Strong Biotech, Cat. No. AV 250) following the manufacturer's instruction. In brief, the treated cells were harvested and resuspended in Annexin V binding buffer containing Annexin V-FITC at room temperature. After 15 min incubation in the dark, the cells were washed twice with 200 ul of Annexin V binding buffer. Before FACS analysis, 0.5 ul of propidium iodide (PI) was added. All flow cytometric analyses were performed on a BD-LSR flow cytometer (Becton Dickinson) using the Cell Quest software. The Annexin V positive and/or PI positive cells are considered apoptotic cells. The data in Table 13 showed synergistic effect of all 5F1 antibodies tested in combination with Oxaliplatin in the induction of apoptosis in Colo205 cancer cells.

TABLE 13

Effects of 5F1 antibodies in combination with Oxaliplatin

| % apoptosis* | Oxaliplatin 0 | Oxaliplatin 1 ug/ml | Oxaliplatin 10 ug/ml |
|---|---|---|---|
| Antibody 0 | 0 | 2 | 6 |
| HIg 30 ug/ml | 1 | 4 | 2 |
| c5F1v17 10 ug/ml | 27 | 30 | 46 |
| c5F1v17 30 ug/ml | 49 | 55 | 62 |
| c5F1v24 10 ug/ml | 19 | 30 | 42 |
| c5F1v24 30 ug/ml | 31 | 49 | 54 |
| c5F1v25 10 ug/ml | 20 | 35 | 53 |
| c5F1v25 30 ug/ml | 44 | 54 | 63 |

*Background subtracted.

Binding and Apoptosis Induction of m5F1 Antibody to SU86.86 Pancreatic Cancer Cells Purified m5F1 and control antibodies at 1 ug/ml were added to $2 \times 10^5$ SU.86.86 cells and incubated for 1 hour at 4° C., washed twice with PBS containing 1% FBS, followed by incubation with 1 ug/ml of corresponding secondary antibodies (R-PE-conjugated goat F(ab')2 anti-mouse IgG(H+L), Southern Biotech, Cat. No. 1032-09) at 4° C. for 1 hour. At the end of staining, samples were washed twice with PBS containing 1% FBS and analyzed by flow cytometer. All flow cytometric analyses were performed on a BD-LSR flow cytometer (Becton Dickinson) using the Cell Quest software.

TABLE 14

Binding of 5F1 to SU.86.86 cells

| Antibodies | MFI |
|---|---|
| 2$^{nd}$ alone | 6 |
| m5F1 | 131 |

$2 \times 10^5$ of SU86.86 cells were seeded into the wells of 12-well plates. Aliquots of purified m5F1 at the concentration ranging from 2 to 32 ug/ml were prepared freshly in culture medium and added to each well. Control antibody at 32 ug/ml was included for background signal measurement. The treated cells were kept at 37° incubator for 6 h before FACS analysis for apoptosis. For cellular apoptosis assay, Annexin V staining was measured using Annexin-V-FITC Apoptosis Detection Kit (Strong Biotech, Cat. No. AVK250) following the manufacturer's instruction. In brief, the treated cells were harvested and resuspended in Annexin V binding buffer containing Annexin V-FITC at room temperature. After 15 min incubation in the dark, the cells were washed twice with 200 μl of Annexin V binding buffer. Before FACS analysis, 0.25 μg/ml of propidium iodide (PI) was added. All flow cytometric analyses were performed on a BD-LSR flow cytometer (Becton Dickinson) using the Cell Quest software. The Annexin VI positive and/or PI positive cells are considered apoptotic cells.

TABLE 15

Apoptosis induction of SU.86.86 by m5F1 antibody

| | 0 | 2 ug/ml | 4 ug/ml | 8 ug/ml | 16 ug/ml | 32 ug/ml |
|---|---|---|---|---|---|---|
| mIgG1 | ND | ND | ND | ND | ND | 36 |
| m5F1 | 36 | 60 | 72 | 78 | 89 | 91 |

(% of Annexin V and/or PI positive cells)

The data shown in Tables 14 and 15 showed that m5F1 could bind to pancreatic cancer cell line SU.86/86, and binding of m5F1 induced apoptosis in SU.86.86 cells.

Binding experiments were carried out for antibodies c5F1.v15, c5F1.v16, and c5F1.v24. These antibodies showed significant binding to SU.86.86 cells. Apoptosis assay was carried out for antibody c5F1.v15. Data indicated that this antibody at 8 ug/ml and 32 ug/ml induced apoptosis of SU.86.86 cells only in the presence of a cross-linker mouse anti-human IgG which is Fcγ fragment specific (Jackson ImmunoResearch 209-005-098).

REFERENCES

Pimenidou, A., Madden, L. A., Topping, K. P., Smith, K. A., Monson, J. R., and Greenman, J. (2004) Novel CD43 specific phage antibodies react with early stage colorectal tumours. Oncol. Rep. 11(2):327-31.

Fernandez-Rodriguez, J., Andersson, C. X., Laos, S., Baeckstrom, D., Sikut, A., Sikut, R., and Hansson, G. C. (2002) The leukocyte antigen CD43 is expressed in different cell lines of nonhematopoietic origin. Tumour Biol. 23(4): 193-201.

Cermak, L., Simova, S., Pintzas, A., Horejsi, V., and Andera, L. (2002) Molecular mechanisms involved in CD43- mediated apoptosis of TF-1 cells. Roles of transcription Daxx expression, and adhesion molecules. J Biol. Chem. 8; 277 (10):7955-61.

Carlow, D. A., Corbel, S. Y., and Ziltener, H. J. (2001) Absence of CD43 fails to alter T cell development and responsiveness. J. Immunol. 166(1):256-61.

Nieto, M., Rodriguez-Fernandez, J. L., Navarro, F., Sancho, D., Frade, J. M., Mellado, M., Martinez-A, C., Cabanas, C., and Sanchez-Madrid, F. (1999) Signaling through CD43 induces natural killer cell activation, chemokine release, and PYK-2 activation. Blood. 94(8):2767-77.

Sikut, R., Andersson, C. X., Sikut, A., Fernandez-Rodriguez, J., Karlsson, N. G., and Hansson, G. C. (1999) Detection of CD43 (leukosialin) in colon adenoma and adenocarcinoma by novel monoclonal antibodies against its intracellular domain. Int. J. Cancer. 82(1):52-8.

Lopez, S., Seveau, S., Lesavre, P., Robinson, M. K., and Halbwachs-Mecarelli, L. (1998) CD43 (sialophorin, leukosialin) shedding is an initial event during neutrophil migration, which could be closely related to the spreading of adherent cells. Cell Adhes. Commun. 5(2):151-60.

Stockton, B. M., Cheng, G., Manjunath, N., Ardman, B., and von Andrian, U. H. (1998) Negative regulation of T cell homing by CD43. Immunity. 8(3):373-81.

McEvoy, L. M., Jutila, M. A., Tsao, P. S., Cooke, J. P., and Butcher, E. C. (1997) Anti-CD43 inhibits monocyte-endothelial adhesion in inflammation and atherogenesis. Blood. 90(9):3587-94.

Manjunath, N., Correa, M., Ardman, M., and Ardman, B. (1995) Negative regulation of T-cell adhesion and activation by CD43. Nature. 377(6549):535-8

Pallant, A., Eskenazi, A., Mattei, M G., Fournier, R. E. K., Carlsson, S. R., Fukuda, M., and Frelinger, J. G. (1989) Characterization of cDNA encoding human leukosialin and localization of the leukosialin gene to chromosome 16. Proc. Natl. Acad. Sci. USA 86:1328-32.

Shelley, C. S., Remold-O'Donnell, E., Davis III, A. E., Bruns, G. A. P., Rosen, F. S., Carroll, M. C., and Whitehead, A. S. (1989) Molecular characterization of sialophorin (CD43), the lymphocyte surface sialoglycoprotein defective in Wiskott-Aldrich syndrome. Proc. Natl. Acad. Sci. USA 86: 2819-23.

What is claimed is:

1. An isolated antibody that specifically binds to an epitope on a CD43 or a carcinoembryonic antigen (CEA) expressed by a nonhematopoietic cancer cell, said antibody comprising a heavy chain and a light chain, wherein
   (a) the heavy chain comprises a heavy chain variable region comprising the three complementary determining regions (CDRs) from the amino acid sequence of SEQ ID NO:1, and a heavy chain constant region comprising the amino acid sequence of SEQ ID NO:9, wherein the hinge region of the heavy chain constant region comprises at least one amino acid insertion, deletion or substitution; and
   (b) the light chain comprises a light chain variable region comprising the three complementary determining regions (CDRs) from the amino acid sequence of SEQ ID NO:2, and a light chain constant region comprising the amino acid sequence of SEQ ID NO:10 and further comprising at least one amino acid insertion in the constant region.

2. The antibody of claim 1, wherein the antibody is a humanized antibody.

3. The antibody of claim 1, wherein the antibody is a chimeric antibody.

4. An antibody that specifically binds to an epitope on a CD43 or a carcinoembryonic antigen (CEA) expressed by a nonhematopoietic cancer cell, said antibody comprising a heavy chain and a light chain, wherein
   (a) the heavy chain comprises a heavy chain variable region comprising the three complementary determining regions (CDRs) from the amino acid sequence of SEQ ID NO:1, and a heavy chain constant region comprising the amino acid sequence selected from the group consisting of SEQ ID NOS:11-30, and (b) the light chain comprises a light chain variable region comprising the three complementary determining regions (CDRs) from the amino acid sequence of SEQ ID NO:2, and a light chain constant region comprising the amino acid sequence selected from the group consisting of SEQ ID NOS:10 and 31-37.

5. The antibody of claim 4, wherein the heavy chain constant region comprises the amino acid sequence of SEQ ID NO:27.

6. The antibody of claim 4, wherein the heavy chain variable region comprises the amino acid sequence of residues 20-137 of SEQ ID NO:1 and the heavy chain constant region comprises the amino acid sequence of SEQ ID NO:27, and the light chain variable region comprises the amino acid sequence of residues 20-131 of SEQ ID NO:2 and the light chain constant region comprises the amino acid sequence of SEQ ID NO:10.

7. The antibody of claim 4, wherein the heavy chain constant region comprises the amino acid sequence of SEQ ID NO:29.

8. The antibody of claim 4, wherein the heavy chain variable region comprises the amino acid sequence of residues 20-137 of SEQ ID NO:1 and the heavy chain constant region comprises the amino acid sequence of SEQ ID NO:29, and the light chain variable region comprises the amino acid sequence of residues 20-131 of SEQ ID NO:2 and the light chain constant region comprises the amino acid sequence of SEQ ID NO:34.

9. The antibody of claim 4, wherein the heavy chain variable region comprises the amino acid sequence of residues 20-137 of SEQ ID NO:1 and the heavy chain constant region comprises the amino acid sequence of SEQ ID NO:29, and the light chain variable region comprises the amino acid sequence of residues 20-131 of SEQ ID NO:2 and the light chain constant region comprises the amino acid sequence of SEQ ID NO:35.

10. A pharmaceutical composition comprising the antibody of claim 1, and a pharmaceutically acceptable carrier.

11. An antibody that specifically binds to an epitope on a CD43 or a carcinoembryonic antigen (CEA) expressed by a nonhematopoietic cancer cell, wherein the antibody is produced by a method comprising expressing one or more polynucleotides encoding the heavy and light chain of the antibody of claim 1 in a host cell, and recovering the antibody produced by the host cell.

12. The antibody of claim 4, wherein the antibody is a humanized antibody.

13. The antibody of claim 12, wherein the heavy chain constant region comprises the amino acid sequence of SEQ ID NO:27, and the light chain constant region comprises the amino acid sequence of SEQ ID NO:10.

14. The antibody of claim 12, wherein the heavy chain constant region comprises the amino acid sequence of SEQ ID NO:29, and the light chain constant region comprises the amino acid sequence of SEQ ID NO:34.

15. The antibody of claim 12, wherein the heavy chain constant region comprises the amino acid sequence of SEQ ID NO:29, and the light chain constant region comprises the amino acid sequence of SEQ ID NO:35.

16. The antibody of claim 4, wherein the antibody is a chimeric antibody.

17. A pharmaceutical composition comprising the antibody of claim 4, and a pharmaceutically acceptable carrier.

18. An antibody that specifically binds to an epitope on a CD43 or a carcinoembryonic antigen (CEA) expressed by a nonhematopoietic cancer cell, wherein the antibody is produced by a method comprising:

(1) expressing in a host cell, one or more polynucleotides comprising (a) a nucleic acid sequence encoding a heavy chain comprising a heavy chain variable region comprising the three CDRs from the amino acid sequence of SEQ ID NO:1 and a heavy chain constant region comprising the amino acid sequence selected from the group consisting of SEQ ID NOS:11-30; and (b) a nucleic acid sequence encoding a light chain comprising a light chain variable region comprising the three CDRs from the amino acid sequence of SEQ ID NO:2 and a constant region comprising the amino acid sequence selected from the group consisting of SEQ ID NOS:10 and 31-37, wherein the heavy chain and the light chain are expressed in said host cell;

(2) recovering the antibody expressed by said host cell.

19. A kit comprising a pharmaceutical composition comprising the antibody of claim 1 and a pharmaceutically acceptable carrier.

20. The kit of claim 19, wherein the kit further comprises a package insert comprising instructions for administering the pharmaceutical composition in conjunction with another anti-cancer agent to an individual for treating nonhematopoietic cancer.

21. A kit comprising a first pharmaceutical composition comprising the antibody of claim 1 and a pharmaceutically acceptable carrier, and a second pharmaceutical composition comprising another anti-cancer agent.

22. The kit of claim 19, wherein the kit further comprises a package insert comprising instructions for administering an effective amount of the pharmaceutical composition to an individual for treating nonhematopoietic cancer.

23. The kit of claim 21, wherein the kit further comprises a package insert comprising instructions for administering the first pharmaceutical composition and the second pharmaceutical composition in conjunction to an individual for treating nonhematopoietic cancer.

24. A kit comprising a pharmaceutical composition comprising the antibody of claim 4 and a pharmaceutically acceptable carrier.

25. The kit of claim 24, wherein the kit further comprises a package insert comprising instructions for administering an effective amount of the pharmaceutical composition to an individual for treating nonhematopoietic cancer.

26. The kit of claim 24, wherein the kit further comprises a package insert comprising instructions for administering the pharmaceutical composition in conjunction with another anti-cancer agent to an individual for treating nonhematopoietic cancer.

27. A kit comprising a first pharmaceutical composition comprising the antibody of claim 4 and a pharmaceutically acceptable carrier, and a second pharmaceutical composition comprising another anti-cancer agent.

28. The kit of claim 27, wherein the kit further comprises a package insert comprising instructions for administering the first pharmaceutical composition and the second pharmaceutical composition in conjunction to an individual for treating nonhematopoietic cancer.

29. A method of producing an antibody, comprising culturing a host cell comprising one or more polynucleotides encoding the heavy and light chain of the antibody of claim 1, wherein the antibody is produced in the host cell, and recovering the antibody from the cell culture.

30. A method of producing an antibody, comprising expressing in a host cell,
    (a) a polynucleotide comprising a nucleic acid sequence encoding a heavy chain comprising a heavy chain variable region comprising the three CDRs from the amino acid sequence of SEQ ID NO:1 and a heavy chain constant region comprising the amino acid sequence selected from the group consisting of SEQ ID NOS:11-30; and
    (b) a polynucleotide comprising a nucleic acid sequence encoding a light chain comprising a light chain variable region comprising the three CDRs from the amino acid sequence of SEQ ID NO:2 and a constant region comprising the amino acid sequence selected from the group consisting of SEQ ID NOS:10 and 31-37,
    wherein the polynucleotides encoding the heavy chain and light chain are co-expressed in said host cell.

31. The method of claim 30, wherein the antibody is isolated from the cell culture.

32. A method of producing an antibody, comprising culturing a host cell comprising one or more polynucleotides encoding the heavy and light chain of the antibody of claim 4, wherein the antibody is produced in the host cell; and recovering the antibody from the cell culture.

* * * * *

SEQUENCE LISTING

```
<160> NUMBER OF SEQ ID NOS: 167

<210> SEQ ID NO 1
<211> LENGTH: 137
<212> TYPE: PRT
<213> ORGANISM: Murine

<400> SEQUENCE: 1

Met Glu Trp Ser Trp Ile Phe Leu Phe Leu Ser Gly Thr Ala Gly
 1               5                  10                  15

Val His Ser Glu Val Gln Leu Gln Gln Ser Gly Pro Glu Leu Val Lys
            20                  25                  30

Pro Gly Ala Ser Val Arg Met Ser Cys Thr Ala Ser Gly Tyr Thr Phe
        35                  40                  45

Thr Ser Tyr Val Met His Trp Ile Lys Gln Lys Pro Gly Gln Gly Leu
    50                  55                  60

Asp Trp Ile Gly Tyr Ile Asn Pro Tyr Asn Gly Gly Thr Gln Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Arg Thr Phe Pro Tyr Tyr Phe Asp Tyr Trp Gly
        115                 120                 125

Gln Gly Thr Thr Leu Thr Val Ser Ser
    130                 135

<210> SEQ ID NO 2
<211> LENGTH: 131
<212> TYPE: PRT
<213> ORGANISM: Murine

<400> SEQUENCE: 2

Met Lys Leu Pro Val Arg Leu Leu Val Leu Met Phe Trp Ile Pro Ala
 1               5                  10                  15

Ser Ser Ser Asp Val Leu Met Thr Gln Thr Pro Leu Ser Leu Pro Val
            20                  25                  30
```

```
Ser Leu Gly Asp Gln Ala Ser Ile Ser Cys Arg Ser Ser Gln Ser Ile
        35                  40                  45

Leu His Ser Asn Gly Asn Thr Tyr Leu Glu Trp Tyr Leu Gln Lys Pro
 50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Ala Pro Leu Thr Phe Gly Ala Gly Thr Lys Leu
        115                 120                 125

Glu Leu Lys
    130

<210> SEQ ID NO 3
<211> LENGTH: 137
<212> TYPE: PRT
<213> ORGANISM: Artificial Sequence
<220> FEATURE:
<223> OTHER INFORMATION: Synthetic Construct

<400> SEQUENCE: 3

Met Gly Trp Ser Trp Ile Phe Leu Phe Leu Leu Ser Gly Thr Ala Gly
 1               5                  10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Val Met His Trp Val Arg Gln Ala Pro Gly Gln Gly Leu
 50                  55                  60

Glu Trp Ile Gly Tyr Ile Asn Pro Tyr Asn Gly Gly Thr Gln Tyr Asn
65                  70                  75                  80

Glu Lys Phe Lys Gly Lys Ala Thr Ile Thr Ala Asp Glu Ser Thr Asn
                85                  90                  95

Thr Ala Tyr Met Glu Leu Ser Ser Leu Thr Ser Glu Asp Ser Ala Val
            100                 105                 110

Tyr Tyr Cys Ala Arg Arg Thr Phe Pro Tyr Tyr Phe Asp Tyr Trp Gly
        115                 120                 125

Gln Gly Thr Thr Leu Thr Val Ser Ser
    130                 135

<210> SEQ ID NO 4
<211> LENGTH: 132
<212> TYPE: PRT
<213> ORGANISM: Artificial Sequence
<220> FEATURE:
<223> OTHER INFORMATION: Synthetic Construct

<400> SEQUENCE: 4

Met Glu Thr Asp Thr Leu Leu Leu Trp Val Leu Leu Leu Trp Val Pro
 1               5                  10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ser Ser Gln Ser
        35                  40                  45

Ile Leu His Ser Asn Gly Asn Thr Tyr Leu Glu Trp Tyr Gln Gln Lys
 50                  55                  60
```

```
Pro Gly Lys Ala Pro Lys Leu Leu Ile Tyr Lys Val Ser Asn Arg Phe
 65                  70                  75                  80

Ser Gly Val Pro Ser Arg Phe Ser Gly Ser Gly Ser Gly Thr Asp Phe
                 85                  90                  95

Thr Leu Thr Ile Ser Ser Leu Gln Pro Asp Asp Phe Ala Thr Tyr Tyr
            100                 105                 110

Cys Phe Gln Gly Ser His Ala Pro Leu Thr Phe Gly Gln Gly Thr Lys
        115                 120                 125

Val Glu Leu Lys
    130

<210> SEQ ID NO 5
<211> LENGTH: 411
<212> TYPE: DNA
<213> ORGANISM: Murine

<400> SEQUENCE: 5
atggaatgga gttggatatt tctctttctc ctgtcaggaa ctgcaggtgt ccactctgag       60
gtccagctgc agcagtctgg acctgagctg gtaaagcctg ggcttcagt gaggatgtcc      120 tgcacggctt ctggatacac attcactagc tatgttatgc actggataaa gcagaagcct      180
gggcagggcc ttgactggat tggatatatt aatccttaca atggtggtac tcagtacaat      240
gagaagttca aggcaaggc cacactgact tcagacaaat cctccagcac agcctacatg       300
gagctcagca gcctgacctc tgaggactct gcggtctatt actgtgcaag acggaccttc      360
ccgtactact ttgactactg gggccaaggc accactctca cagtctcctc a              411

<210> SEQ ID NO 6
<211> LENGTH: 393
<212> TYPE: DNA
<213> ORGANISM: Murine

<400> SEQUENCE: 6
atgaagttgc ctgttaggct gttggtgctg atgttctgga ttcctgcttc cagcagtgat       60
gttttgatga cccaaactcc actctccctg cctgtcagtc ttggagatca agcctccatc      120
tcttgcagat ctagtcagag cattttacat agtaatggaa acacctattt agaatggtac      180
ctgcagaaac caggccagtc tccaaagctc ctgatctaca agtttccaa ccgattttct       240 ggggtcccag acaggttcag tggcagtgga tcagggacag atttcacact caagatcagc      300
agagtggagg ctgaggatct gggagtttac tactgctttc aaggttcaca tgctcctctc      360
acgttcggtg ctgggaccaa gctggagctg aaa                                  393

<210> SEQ ID NO 7
<211> LENGTH: 411
<212> TYPE: DNA
<213> ORGANISM: Artificial Sequence
<220> FEATURE:
<223> OTHER INFORMATION: Synthetic Construct

<400> SEQUENCE: 7
atgggatgga gctggatctt tctcttcctc ctgtcaggta ccgcgggcgt gcactctcag       60
gtccagcttg tccagtctgg ggctgaagtc aagaaacctg gctcgagcgt gaaggtctcc      120
tgcaaggctt ctggctacac ctttactagc tatgttatgc actgggtaag gcaggccct       180 ggacagggtc tggaatggat tggatatatt aatccttaca atggtggtac tcagtacaat      240
gagaagttca aggcaaggc cacaattact gcagacgaat ccaccaatac agcctacatg       300
gaactgagca gcctgacatc tgaggacagc gcagtctatt actgtgcaag acggaccttc      360
```
ccgtactact tgactactg gggccaagga accacgctca cagtctcctc a    411

<210> SEQ ID NO 8
<211> LENGTH: 396
<212> TYPE: DNA
<213> ORGANISM: Artificial Sequence
<220> FEATURE:
<223> OTHER INFORMATION: Synthetic Construct

<400> SEQUENCE: 8
atggagaccg ataccctcct gctatgggtc ctcctgctat gggtcccagg atcaaccgga    60
gatattcaga tgacccagtc tccatcttcc ctctctgcta gcgtcgggga tagggtcacc    120
ataacctgca gatctagtca gagcatttta catagtaatg aaacaccta tttagaatgg    180 taccagcaga agccaggcaa agctcccaag cttctaatct ataaagtttc aaccgattt    240 tctggagtcc cttcacgctt cagtggcagt ggatctggga ccgatttcac cctcacaatc    300
agctctctgc agccagatga tttcgccact tattactgct ttcaaggttc acatgctcct    360
ctcacgttcg gtcaggggac caaggtggag ctgaaa    396

<210> SEQ ID NO 9
<211> LENGTH: 329
<212> TYPE: PRT
<213> ORGANISM: Homo sapiens

<400> SEQUENCE: 9

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Arg Asp Glu Leu
225                 230                 235                 240

```
Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 10
<211> LENGTH: 107
<212> TYPE: PRT
<213> ORGANISM: Homo sapiens

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 11
<211> LENGTH: 330
<212> TYPE: PRT
<213> ORGANISM: Artificial Sequence
<220> FEATURE:
<223> OTHER INFORMATION: Synthetic Construct

<400> SEQUENCE: 11

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 12
<211> LENGTH: 330
<212> TYPE: PRT
<213> ORGANISM: Artificial Sequence
<220> FEATURE:
<223> OTHER INFORMATION: Synthetic Construct

<400> SEQUENCE: 12

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 330
<212> TYPE: PRT
<213> ORGANISM: Artificial Sequence
<220> FEATURE:
<223> OTHER INFORMATION: Synthetic Construct

<400> SEQUENCE: 13

Ala Ser Thr Lys Gly Pro Ser Val Phe Pro Leu Val Pro Gly Cys Ser
 1               5                  10                  15

Asp Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
                195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 14
<211> LENGTH: 330
<212> TYPE: PRT
<213> ORGANISM: Artificial Sequence
<220> FEATURE:
<223> OTHER INFORMATION: Synthetic Construct

<400> SEQUENCE: 14

Ala Ser Thr Lys Gly Pro Ser Val Phe Pro Leu Ala Pro Gly Cys Ser
1               5                   10                  15
Asp Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Ser Asp Lys Thr His Thr Cys Pro Pro Cys
                100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
```

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 330
<212> TYPE: PRT
<213> ORGANISM: Artificial Sequence
<220> FEATURE:
<223> OTHER INFORMATION: Synthetic Construct

<400> SEQUENCE: 15

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Gly Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 329
<212> TYPE: PRT
<213> ORGANISM: Artificial Sequence
<220> FEATURE:
<223> OTHER INFORMATION: Synthetic Construct

<400> SEQUENCE: 16

Ala Ser Thr Lys Gly Pro Ser Val Phe Pro Leu Ala Pro Cys Ser Arg
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Ser Asp Lys Thr His Thr Gly Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
                    305                 310                 315                 320
        Gln Lys Ser Leu Ser Leu Ser Pro Gly
                        325

<210> SEQ ID NO 17
<211> LENGTH: 330
<212> TYPE: PRT
<213> ORGANISM: Artificial Sequence
<220> FEATURE:
<223> OTHER INFORMATION: Synthetic Construct

<400> SEQUENCE: 17

Ala Ser Thr Lys Gly Pro Ser Val Phe Pro Leu Ala Pro Cys Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Ser Asp Lys Thr His Thr Gly Ser Ser Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
```

```
<211> LENGTH: 330
<212> TYPE: PRT
<213> ORGANISM: Artificial Sequence
<220> FEATURE:
<223> OTHER INFORMATION: Synthetic Construct

<400> SEQUENCE: 18

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Ser Asp Lys Thr His Thr Gly Ser Ser Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 330
<212> TYPE: PRT
<213> ORGANISM: Artificial Sequence
<220> FEATURE:
<223> OTHER INFORMATION: Synthetic Construct

<400> SEQUENCE: 19
```

```
Ala Ser Thr Lys Gly Pro Ser Val Phe Pro Leu Ala Pro Cys Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Ser Asp Lys Thr Pro Pro Gly Ser Ser Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 330
<212> TYPE: PRT
<213> ORGANISM: Artificial Sequence
<220> FEATURE:
<223> OTHER INFORMATION: Synthetic Construct

<400> SEQUENCE: 20

Ala Ser Thr Lys Gly Pro Ser Val Phe Pro Leu Ala Pro Cys Ser Arg
  1               5                  10                  15

Ser Thr Ser Gly Gly Thr Ala Ala Leu Gly Cys Leu Val Lys Asp Tyr
             20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr Pro Gly Ser Ser Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 21
<211> LENGTH: 330
<212> TYPE: PRT
<213> ORGANISM: Artificial Sequence
<220> FEATURE:
<223> OTHER INFORMATION: Synthetic Construct

<400> SEQUENCE: 21

Ala Ser Thr Lys Gly Pro Ser Val Phe Pro Leu Val Pro Gly Cys Ser
1               5                   10                  15

Asp Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

65                  70                  75                  80
Tyr Ile Cys Asn Val Asn His Lys Pro Ser Asn Thr Lys Val Asp Lys
                 85                  90                  95
Lys Val Glu Pro Lys Ser Ser Asp Lys Thr Pro Pro Gly Ser Ser Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 22
<211> LENGTH: 330
<212> TYPE: PRT
<213> ORGANISM: Artificial Sequence
<220> FEATURE:
<223> OTHER INFORMATION: Synthetic Construct

<400> SEQUENCE: 22

Ala Ser Thr Lys Gly Pro Ser Val Phe Pro Leu Ala Pro Gly Cys Ser
1               5                   10                  15
Asp Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Ser Asp Lys Thr Pro Pro Gly Ser Ser Cys
            100                 105                 110

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 331
<212> TYPE: PRT
<213> ORGANISM: Artificial Sequence
<220> FEATURE:
<223> OTHER INFORMATION: Synthetic Construct

<400> SEQUENCE: 23

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Arg Ile Pro Lys Pro Ser Thr Pro Pro Gly Ser Ser
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140
```

```
Cys Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
        290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 24
<211> LENGTH: 331
<212> TYPE: PRT
<213> ORGANISM: Artificial Sequence
<220> FEATURE:
<223> OTHER INFORMATION: Synthetic Construct

<400> SEQUENCE: 24

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Arg Ile Pro Lys Pro Ser Thr Pro Pro Gly Ser Ser
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
```

```
                    180                 185                 190
Leu His Gln Asp Trp Leu Asn Gly Lys Glu Tyr Lys Cys Lys Val Ser
                195                 200                 205

Asn Lys Ala Leu Pro Ala Pro Ile Glu Lys Thr Ile Ser Lys Ala Lys
            210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 25
<211> LENGTH: 329
<212> TYPE: PRT
<213> ORGANISM: Artificial Sequence
<220> FEATURE:
<223> OTHER INFORMATION: Synthetic Construct

<400> SEQUENCE: 25

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220
```

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
        260                 265                 270

Tyr Lys Thr Thr Pro Pro Val Leu Asp Ser Asp Gly Ser Phe Phe Leu
    275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 26
<211> LENGTH: 330
<212> TYPE: PRT
<213> ORGANISM: Artificial Sequence
<220> FEATURE:
<223> OTHER INFORMATION: Synthetic Construct

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

```
Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 331
<212> TYPE: PRT
<213> ORGANISM: Artificial Sequence
<220> FEATURE:
<223> OTHER INFORMATION: Synthetic Construct

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
```

```
                    290                 295                 300
Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 28
<211> LENGTH: 330
<212> TYPE: PRT
<213> ORGANISM: Artificial Sequence
<220> FEATURE:
<223> OTHER INFORMATION: Synthetic Construct

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Cys Ser Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 29
<211> LENGTH: 333
<212> TYPE: PRT
<213> ORGANISM: Artificial Sequence
<220> FEATURE:
<223> OTHER INFORMATION: Synthetic Construct

<400> SEQUENCE: 29

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Asp Lys Ser Cys Asp Lys Thr His Thr Cys
            100                 105                 110

Pro Pro Cys Pro Ala Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ala Pro Ile Glu Lys Thr Ile Ser Lys
    210                 215                 220

Ala Lys Gly Gln Pro Arg Glu Pro Gln Val Tyr Thr Leu Pro Pro Ser
225                 230                 235                 240

Arg Asp Glu Leu Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330
```

<210> SEQ ID NO 30
<211> LENGTH: 333
<212> TYPE: PRT
<213> ORGANISM: Artificial Sequence
<220> FEATURE:

-continued

<223> OTHER INFORMATION: Synthetic Construct

<400> SEQUENCE: 30

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Ser Asp Lys Thr His Thr Cys
            100                 105                 110

Pro Pro Cys Pro Ala Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ala Pro Ile Glu Lys Thr Ile Ser Lys
    210                 215                 220

Ala Lys Gly Gln Pro Arg Glu Pro Gln Val Tyr Thr Leu Pro Pro Ser
225                 230                 235                 240

Arg Asp Glu Leu Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330
```

<210> SEQ ID NO 31
<211> LENGTH: 109
<212> TYPE: PRT
<213> ORGANISM: Artificial Sequence
<220> FEATURE:
<223> OTHER INFORMATION: Synthetic Construct

<400> SEQUENCE: 31

```
Arg Thr Val Ala Ala Pro Ser Val Phe Ile Phe Pro Pro Ser Asp Glu
1               5                   10                  15
```

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Gly Glu Cys
            100                 105

<210> SEQ ID NO 32
<211> LENGTH: 110
<212> TYPE: PRT
<213> ORGANISM: Artificial Sequence
<220> FEATURE:
<223> OTHER INFORMATION: Synthetic Construct

<400> SEQUENCE: 32

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Gly Glu Gly Glu Cys
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Synthetic Construct

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Gly Gly Glu Gly Glu Cys
            100                 105                 110

```
<210> SEQ ID NO 34
<211> LENGTH: 108
<212> TYPE: PRT
<213> ORGANISM: Artificial Sequence
<220> FEATURE:
<223> OTHER INFORMATION: Synthetic Construct

<400> SEQUENCE: 34
```

Arg Thr Val Ala Ala Pro Ser Val Phe Ile Phe Pro Pro Ser Asp Glu
 1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Gly Glu Cys
            100                 105

```
<210> SEQ ID NO 35
<211> LENGTH: 109
<212> TYPE: PRT
<213> ORGANISM: Artificial Sequence
<220> FEATURE:
<223> OTHER INFORMATION: Synthetic Construct

<400> SEQUENCE: 35
```

Arg Thr Val Ala Ala Pro Ser Val Phe Ile Phe Pro Pro Ser Asp Glu
 1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Gly Gly Glu Cys
            100                 105

```
<210> SEQ ID NO 36
<211> LENGTH: 110
<212> TYPE: PRT
<213> ORGANISM: Artificial Sequence
<220> FEATURE:
<223> OTHER INFORMATION: Synthetic Construct

<400> SEQUENCE: 36
```

Arg Thr Val Ala Ala Pro Ser Val Phe Ile Phe Pro Pro Ser Asp Glu
 1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Gly Gly Gly Glu Cys
            100                 105                 110

<210> SEQ ID NO 37
<211> LENGTH: 111
<212> TYPE: PRT
<213> ORGANISM: Artificial Sequence
<220> FEATURE:
<223> OTHER INFORMATION: Synthetic Construct

<400> SEQUENCE: 37

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Gly Gly Gly Glu Cys
            100                 105                 110

<210> SEQ ID NO 38
<211> LENGTH: 20
<212> TYPE: DNA
<213> ORGANISM: Artificial Sequence
<220> FEATURE:
<223> OTHER INFORMATION: Synthetic Construct

<400> SEQUENCE: 38
accacctctc ttgcagcctc                                            20

<210> SEQ ID NO 39
<211> LENGTH: 18
<212> TYPE: DNA
<213> ORGANISM: Artificial Sequence
<220> FEATURE:
<223> OTHER INFORMATION: Synthetic Construct

<400> SEQUENCE: 39
cattgctctc ccactcca                                              18

<210> SEQ ID NO 40
<211> LENGTH: 37
<212> TYPE: DNA
<213> ORGANISM: Artificial Sequence
<220> FEATURE:
<223> OTHER INFORMATION: Synthetic Construct

<400> SEQUENCE: 40
tctatctaga tggaatggag ttggatattt ctctttc                         37

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct

<400> SEQUENCE: 41
atatggctct tggcaggtct                                             20

<210> SEQ ID NO 42
<211> LENGTH: 21
<212> TYPE: DNA
<213> ORGANISM: Artificial Sequence
<220> FEATURE:
<223> OTHER INFORMATION: Synthetic Construct

<400> SEQUENCE: 42
gggagatctg gatcctagaa g                                           21

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43
taatcctagg aattctaaac tctg                                        24

<210> SEQ ID NO 44
<211> LENGTH: 51
<212> TYPE: DNA
<213> ORGANISM: Artificial Sequence
<220> FEATURE:
<223> OTHER INFORMATION: Synthetic Construct

<400> SEQUENCE: 44
accctctaga ggttgtgagg actcacctga ggagactgtg agagtggtgc c          51

<210> SEQ ID NO 45
<211> LENGTH: 30
<212> TYPE: DNA
<213> ORGANISM: Artificial Sequence
<220> FEATURE:
<223> OTHER INFORMATION: Synthetic Construct

<400> SEQUENCE: 45
tctatctaga tgaagttgcc tgttaggctg                                  30

<210> SEQ ID NO 46
<211> LENGTH: 43
<212> TYPE: DNA
<213> ORGANISM: Artificial Sequence
<220> FEATURE:
<223> OTHER INFORMATION: Synthetic Construct

<400> SEQUENCE: 46
accctctaga attaggaaag tgcacttacg tttcagctcc agc                   43

<210> SEQ ID NO 47
<211> LENGTH: 28
<212> TYPE: DNA
<213> ORGANISM: Artificial Sequence
<220> FEATURE:
<223> OTHER INFORMATION: Synthetic Construct

<400> SEQUENCE: 47
cagagcccaa atctgacaaa actcacac                                28

<210> SEQ ID NO 48
<211> LENGTH: 31
<212> TYPE: DNA
<213> ORGANISM: Artificial Sequence
<220> FEATURE:
<223> OTHER INFORMATION: Synthetic Construct

<400> SEQUENCE: 48
cagagcccaa atcttctgac aaaactcaca c                            31

<210> SEQ ID NO 49
<211> LENGTH: 38
<212> TYPE: DNA
<213> ORGANISM: Artificial Sequence
<220> FEATURE:
<223> OTHER INFORMATION: Synthetic Construct

<400> SEQUENCE: 49
gagcccaaat ctgacaaatc ttgtgacaaa actcacac                     38

<210> SEQ ID NO 50
<211> LENGTH: 37
<212> TYPE: DNA
<213> ORGANISM: Artificial Sequence
<220> FEATURE:
<223> OTHER INFORMATION: Synthetic Construct

<400> SEQUENCE: 50
gatttgtcag atttgggctc tgcagagaga agattgg                      37

<210> SEQ ID NO 51
<211> LENGTH: 40
<212> TYPE: DNA
<213> ORGANISM: Artificial Sequence
<220> FEATURE:
<223> OTHER INFORMATION: Synthetic Construct

<400> SEQUENCE: 51
tgtgacaaat ctgacaaaac tcacacatgc ccaccgtgcc                   40

<210> SEQ ID NO 52
<211> LENGTH: 41
<212> TYPE: DNA
<213> ORGANISM: Artificial Sequence
<220> FEATURE:
<223> OTHER INFORMATION: Synthetic Construct

<400> SEQUENCE: 52
gttttgtcag atttgtcaca agatttgggc tctgcagaga g                 41

<210> SEQ ID NO 53
<211> LENGTH: 40
<212> TYPE: DNA
<213> ORGANISM: Artificial Sequence
<220> FEATURE:
<223> OTHER INFORMATION: Synthetic Construct

<400> SEQUENCE: 53
aactcacaca ggtccaccgt gcccaggtaa gccagcccag                   40

<210> SEQ ID NO 54
<211> LENGTH: 40
<212> TYPE: DNA

-continued

<213> ORGANISM: Artificial Sequence
<220> FEATURE:
<223> OTHER INFORMATION: Synthetic Construct

<400> SEQUENCE: 54
cacggtggac ctgtgtgagt tttgtcagaa gatttgggct                        40

<210> SEQ ID NO 55
<211> LENGTH: 40
<212> TYPE: DNA
<213> ORGANISM: Artificial Sequence
<220> FEATURE:
<223> OTHER INFORMATION: Synthetic Construct

<400> SEQUENCE: 55
cacacaggtt cttcatgccc aggtaagcca gcccaggcct                        40

<210> SEQ ID NO 56
<211> LENGTH: 40
<212> TYPE: DNA
<213> ORGANISM: Artificial Sequence
<220> FEATURE:
<223> OTHER INFORMATION: Synthetic Construct

<400> SEQUENCE: 56
gggcatgaag aacctgtgtg agttttgtca gaagatttgg                        40

<210> SEQ ID NO 57
<211> LENGTH: 40
<212> TYPE: DNA
<213> ORGANISM: Artificial Sequence
<220> FEATURE:
<223> OTHER INFORMATION: Synthetic Construct

<400> SEQUENCE: 57
ctcccccagg ttcttcatgc ccaggtaagc cagcccaggc                        40

<210> SEQ ID NO 58
<211> LENGTH: 40
<212> TYPE: DNA
<213> ORGANISM: Artificial Sequence
<220> FEATURE:
<223> OTHER INFORMATION: Synthetic Construct

<400> SEQUENCE: 58
gcatgaagaa cctgggggag ttttgtcaga agatttgggc                        40

<210> SEQ ID NO 59
<211> LENGTH: 49
<212> TYPE: DNA
<213> ORGANISM: Artificial Sequence
<220> FEATURE:
<223> OTHER INFORMATION: Synthetic Construct

<400> SEQUENCE: 59
ctgggggggt actgggcttg ggtattctgg gctctgcaga gagaagatt              49

<210> SEQ ID NO 60
<211> LENGTH: 49
<212> TYPE: DNA
<213> ORGANISM: Artificial Sequence
<220> FEATURE:
<223> OTHER INFORMATION: Synthetic Construct

<400> SEQUENCE: 60
caagcccagt accccccag gttcttcatg cccaggtaag ccagcccag               49

<210> SEQ ID NO 61
<211> LENGTH: 31
<212> TYPE: DNA
<213> ORGANISM: Artificial Sequence
<220> FEATURE:
<223> OTHER INFORMATION: Synthetic Construct

<400> SEQUENCE: 61
agcccaaatc ttcttgtgac aaaactcaca c                           31

<210> SEQ ID NO 62
<211> LENGTH: 32
<212> TYPE: DNA
<213> ORGANISM: Artificial Sequence
<220> FEATURE:
<223> OTHER INFORMATION: Synthetic Construct

<400> SEQUENCE: 62
gtcacaagaa gatttgggct ctgcagagag aa                          32

<210> SEQ ID NO 63
<211> LENGTH: 33
<212> TYPE: DNA
<213> ORGANISM: Artificial Sequence
<220> FEATURE:
<223> OTHER INFORMATION: Synthetic Construct

<400> SEQUENCE: 63
gcccaaatgt tctgacaaaa ctcacacatg ccc                         33

<210> SEQ ID NO 64
<211> LENGTH: 33
<212> TYPE: DNA
<213> ORGANISM: Artificial Sequence
<220> FEATURE:
<223> OTHER INFORMATION: Synthetic Construct

<400> SEQUENCE: 64
ttttgtcaga acatttgggc tctgcagaga gaa                         33

<210> SEQ ID NO 65
<211> LENGTH: 38
<212> TYPE: DNA
<213> ORGANISM: Artificial Sequence
<220> FEATURE:
<223> OTHER INFORMATION: Synthetic Construct

<400> SEQUENCE: 65
aggtgtcact gcagccgggt gccaggggga agaccgat                    38

<210> SEQ ID NO 66
<211> LENGTH: 38
<212> TYPE: DNA
<213> ORGANISM: Artificial Sequence
<220> FEATURE:
<223> OTHER INFORMATION: Synthetic Construct

<400> SEQUENCE: 66
acccggctgc agtgacacct ctgggggcac agcggccc                    38

<210> SEQ ID NO 67
<211> LENGTH: 39
<212> TYPE: DNA
<213> ORGANISM: Artificial Sequence
<220> FEATURE:
<223> OTHER INFORMATION: Synthetic Construct

<400> SEQUENCE: 67
tgtcactgca gccggggacc aggggggaaga ccgatgggc        39

<210> SEQ ID NO 68
<211> LENGTH: 39
<212> TYPE: DNA
<213> ORGANISM: Artificial Sequence
<220> FEATURE:
<223> OTHER INFORMATION: Synthetic Construct

<400> SEQUENCE: 68
ggtccccggc tgcagtgaca cctctggggg cacagcggc        39

<210> SEQ ID NO 69
<211> LENGTH: 37
<212> TYPE: DNA
<213> ORGANISM: Artificial Sequence
<220> FEATURE:
<223> OTHER INFORMATION: Synthetic Construct

<400> SEQUENCE: 69
cctggcaccc tgctccaaga gcacctctgg gggcaca        37

<210> SEQ ID NO 70
<211> LENGTH: 38
<212> TYPE: DNA
<213> ORGANISM: Artificial Sequence
<220> FEATURE:
<223> OTHER INFORMATION: Synthetic Construct

<400> SEQUENCE: 70
aggtgctctt ggagcagggt gccagggga agaccgat        38

<210> SEQ ID NO 71
<211> LENGTH: 40
<212> TYPE: DNA
<213> ORGANISM: Artificial Sequence
<220> FEATURE:
<223> OTHER INFORMATION: Synthetic Construct

<400> SEQUENCE: 71
cctggcaccc tgctccagga gcacctctgg gggcacagcg        40

<210> SEQ ID NO 72
<211> LENGTH: 40
<212> TYPE: DNA
<213> ORGANISM: Artificial Sequence
<220> FEATURE:
<223> OTHER INFORMATION: Synthetic Construct

<400> SEQUENCE: 72
cagaggtgct cctggagcag ggtgccaggg ggaagaccga        40

<210> SEQ ID NO 73
<211> LENGTH: 37
<212> TYPE: DNA
<213> ORGANISM: Artificial Sequence
<220> FEATURE:
<223> OTHER INFORMATION: Synthetic Construct

<400> SEQUENCE: 73
cactctccac cacctcctcc cctgttgaag ctctttg        37

<210> SEQ ID NO 74
<211> LENGTH: 37
<212> TYPE: DNA

```
<213> ORGANISM: Artificial Sequence
<220> FEATURE:
<223> OTHER INFORMATION: Synthetic Construct

<400> SEQUENCE: 74
ggggaggagg tggtggagag tgttagaggg agaagtg                              37

<210> SEQ ID NO 75
<211> LENGTH: 35
<212> TYPE: DNA
<213> ORGANISM: Artificial Sequence
<220> FEATURE:
<223> OTHER INFORMATION: Synthetic Construct

<400> SEQUENCE: 75
acactctcca cctcctcccc tgttgaagct ctttg                                35

<210> SEQ ID NO 76
<211> LENGTH: 35
<212> TYPE: DNA
<213> ORGANISM: Artificial Sequence
<220> FEATURE:
<223> OTHER INFORMATION: Synthetic Construct

<400> SEQUENCE: 76 agggaggag gtggagagtg ttagagggag aagtg                                 35

<210> SEQ ID NO 77
<211> LENGTH: 33
<212> TYPE: DNA
<213> ORGANISM: Artificial Sequence
<220> FEATURE:
<223> OTHER INFORMATION: Synthetic Construct

<400> SEQUENCE: 77
aacactctcc tcctcccctg ttgaagctct ttg                                  33

<210> SEQ ID NO 78
<211> LENGTH: 33
<212> TYPE: DNA
<213> ORGANISM: Artificial Sequence
<220> FEATURE:
<223> OTHER INFORMATION: Synthetic Construct

<400> SEQUENCE: 78
caggggagga ggagagtgtt agagggagaa gtg                                  33

<210> SEQ ID NO 79
<211> LENGTH: 30
<212> TYPE: DNA
<213> ORGANISM: Artificial Sequence
<220> FEATURE:
<223> OTHER INFORMATION: Synthetic Construct

<400> SEQUENCE: 79
aacactctcc tccctgttg aagctctttg                                       30

<210> SEQ ID NO 80
<211> LENGTH: 30
<212> TYPE: DNA
<213> ORGANISM: Artificial Sequence
<220> FEATURE:
<223> OTHER INFORMATION: Synthetic Construct

<400> SEQUENCE: 80
caggggagga gagtgttaga gggagaagtg                                      30
```

<210> SEQ ID NO 81
<211> LENGTH: 33
<212> TYPE: DNA
<213> ORGANISM: Artificial Sequence
<220> FEATURE:
<223> OTHER INFORMATION: Synthetic Construct

<400> SEQUENCE: 81
aacactctcc ctctcccctg ttgaagctct ttg                              33

<210> SEQ ID NO 82
<211> LENGTH: 33
<212> TYPE: DNA
<213> ORGANISM: Artificial Sequence
<220> FEATURE:
<223> OTHER INFORMATION: Synthetic Construct

<400> SEQUENCE: 82 cagggggagag ggagagtgtt agagggagaa gtg                             33

<210> SEQ ID NO 83
<211> LENGTH: 36
<212> TYPE: DNA
<213> ORGANISM: Artificial Sequence
<220> FEATURE:
<223> OTHER INFORMATION: Synthetic Construct

<400> SEQUENCE: 83
cactctccct cacctcccct gttgaagctc tttgtg                           36

<210> SEQ ID NO 84
<211> LENGTH: 34
<212> TYPE: DNA
<213> ORGANISM: Artificial Sequence
<220> FEATURE:
<223> OTHER INFORMATION: Synthetic Construct

<400> SEQUENCE: 84
caggggaggt gagggagagt gttagaggga gaag                             34

<210> SEQ ID NO 85
<211> LENGTH: 39
<212> TYPE: DNA
<213> ORGANISM: Artificial Sequence
<220> FEATURE:
<223> OTHER INFORMATION: Synthetic Construct

<400> SEQUENCE: 85
cactctccct caccacctcc cctgttgaag ctctttgtg                        39

<210> SEQ ID NO 86
<211> LENGTH: 37
<212> TYPE: DNA
<213> ORGANISM: Artificial Sequence
<220> FEATURE:
<223> OTHER INFORMATION: Synthetic Construct

<400> SEQUENCE: 86
caggggaggt ggtgagggag agtgttagag ggagaag                          37

<210> SEQ ID NO 87
<211> LENGTH: 118
<212> TYPE: PRT
<213> ORGANISM: Artificial Sequence
<220> FEATURE:
<223> OTHER INFORMATION: Synthetic Construct

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Ile
        35                  40                  45

Gly Tyr Ile Asn Pro Tyr Asn Gly Gly Thr Gln Tyr Asn Glu Lys Phe
50                  55                  60

Lys Gly Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Thr Phe Pro Tyr Tyr Phe Asp Tyr Trp Gly Gln Gly Thr
            100                 105                 110

Leu Val Thr Val Ser Ser
        115

<210> SEQ ID NO 88
<211> LENGTH: 118
<212> TYPE: PRT
<213> ORGANISM: Artificial Sequence
<220> FEATURE:
<223> OTHER INFORMATION: Synthetic Construct

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Ile
        35                  40                  45

Gly Tyr Ile Asn Pro Tyr Asn Gly Gly Thr Gln Tyr Asn Glu Lys Phe
50                  55                  60

Lys Gly Lys Ala Thr Ile Thr Ala Asp Glu Ser Thr Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Thr Phe Pro Tyr Tyr Phe Asp Tyr Trp Gly Gln Gly Thr
            100                 105                 110

Leu Val Thr Val Ser Ser
        115

<210> SEQ ID NO 89
<211> LENGTH: 118
<212> TYPE: PRT
<213> ORGANISM: Artificial Sequence
<220> FEATURE:
<223> OTHER INFORMATION: Synthetic Construct

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Ile
        35                  40                  45

Gly Tyr Ile Asn Pro Tyr Asn Gly Gly Thr Gln Tyr Asn Glu Lys Phe

```
            50                  55                  60
Lys Gly Lys Ala Thr Ile Thr Ala Asp Thr Ser Thr Asn Thr Ala Tyr
 65                  70                  75                  80

Met Glu Leu Ser Ser Leu Thr Ser Glu Asp Ser Ala Val Tyr Tyr Cys
                 85                  90                  95

Ala Arg Arg Thr Phe Pro Tyr Tyr Phe Asp Tyr Trp Gly Gln Gly Thr
            100                 105                 110

Leu Val Thr Val Ser Ser
        115

<210> SEQ ID NO 90
<211> LENGTH: 118
<212> TYPE: PRT
<213> ORGANISM: Artificial Sequence
<220> FEATURE:
<223> OTHER INFORMATION: Synthetic Construct

<400> SEQUENCE: 90

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Val Met His Trp Val Arg Gln Ala Pro Gly Gln Arg Leu Glu Trp Met
         35                  40                  45

Gly Tyr Ile Asn Pro Tyr Asn Gly Gly Thr Gln Tyr Asn Glu Lys Phe
     50                  55                  60

Lys Gly Arg Val Thr Ile Thr Ser Asp Thr Ser Ala Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Arg Thr Phe Pro Tyr Tyr Phe Asp Tyr Trp Gly Gln Gly Thr
            100                 105                 110

Leu Val Thr Val Ser Ser
        115

<210> SEQ ID NO 91
<211> LENGTH: 118
<212> TYPE: PRT
<213> ORGANISM: Artificial Sequence
<220> FEATURE:
<223> OTHER INFORMATION: Synthetic Construct

<400> SEQUENCE: 91

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Val Met His Trp Val Arg Gln Ala Pro Gly Gln Arg Leu Glu Trp Met
         35                  40                  45

Gly Tyr Ile Asn Pro Tyr Asn Gly Gly Thr Gln Tyr Asn Glu Lys Phe
     50                  55                  60

Lys Gly Arg Val Thr Ile Thr Ser Asp Thr Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Arg Thr Phe Pro Tyr Tyr Phe Asp Tyr Trp Gly Gln Gly Thr
            100                 105                 110

Leu Val Thr Val Ser Ser
```

-continued

<210> SEQ ID NO 92
<211> LENGTH: 112
<212> TYPE: PRT
<213> ORGANISM: Artificial Sequence
<220> FEATURE:
<223> OTHER INFORMATION: Synthetic Construct

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Leu His Ser
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Asp Asp Phe Ala Thr Tyr Tyr Cys Phe Gln Gly
                85                  90                  95

Ser His Ala Pro Leu Thr Phe Gly Gln Gly Thr Lys Val Glu Leu Lys
            100                 105                 110

<210> SEQ ID NO 93
<211> LENGTH: 112
<212> TYPE: PRT
<213> ORGANISM: Artificial Sequence
<220> FEATURE:
<223> OTHER INFORMATION: Synthetic Construct

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Leu His Ser
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Asp Asp Phe Ala Thr Tyr Tyr Cys Phe Gln Gly
                85                  90                  95

Ser His Ala Pro Leu Thr Phe Gly Gln Gly Thr Lys Val Glu Leu Lys
            100                 105                 110

<210> SEQ ID NO 94
<211> LENGTH: 112
<212> TYPE: PRT
<213> ORGANISM: Artificial Sequence
<220> FEATURE:
<223> OTHER INFORMATION: Synthetic Construct

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Leu His Ser
            20                  25                  30

```
Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr Asp Phe Thr Leu Lys Ile
 65                  70                  75                  80

Ser Arg Val Glu Ala Glu Asp Leu Gly Thr Tyr Tyr Cys Phe Gln Gly
                 85                  90                  95

Ser His Ala Pro Leu Thr Phe Gly Gln Gly Thr Lys Val Glu Leu Lys
                100                 105                 110

<210> SEQ ID NO 95
<211> LENGTH: 112
<212> TYPE: PRT
<213> ORGANISM: Artificial Sequence
<220> FEATURE:
<223> OTHER INFORMATION: Synthetic Construct

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Leu His Ser
                 20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr Asp Phe Thr Phe Thr Ile
 65                  70                  75                  80

Ser Ser Leu Gln Pro Glu Asp Ile Ala Thr Tyr Tyr Cys Phe Gln Gly
                 85                  90                  95

Ser His Ala Pro Leu Thr Phe Gly Gln Gly Thr Lys Val Glu Ile Lys
                100                 105                 110

<210> SEQ ID NO 96
<211> LENGTH: 112
<212> TYPE: PRT
<213> ORGANISM: Artificial Sequence
<220> FEATURE:
<223> OTHER INFORMATION: Synthetic Construct

<400> SEQUENCE: 96

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Leu His Ser
                 20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr Asp Phe Thr Leu Lys Ile
 65                  70                  75                  80

Ser Arg Val Glu Ala Glu Asp Leu Gly Thr Tyr Tyr Cys Phe Gln Gly
                 85                  90                  95

Ser His Ala Pro Leu Thr Phe Gly Gln Gly Thr Lys Val Glu Ile Lys
                100                 105                 110

<210> SEQ ID NO 97
<211> LENGTH: 65
```

```
<212> TYPE: DNA
<213> ORGANISM: Artificial Sequence
<220> FEATURE:
<223> OTHER INFORMATION: Synthetic Construct

<400> SEQUENCE: 97
tctatctaga tgggatggag ctggatcttt ctcttcctcc tgtcaggtac cgcgggcgtg    60
cactc                                                               65

<210> SEQ ID NO 98
<211> LENGTH: 56
<212> TYPE: DNA
<213> ORGANISM: Artificial Sequence
<220> FEATURE:
<223> OTHER INFORMATION: Synthetic Construct

<400> SEQUENCE: 98
accctctaga ggttgtgagg actcacctga ggagactgtg accagggttc cttggc        56

<210> SEQ ID NO 99
<211> LENGTH: 69
<212> TYPE: DNA
<213> ORGANISM: Artificial Sequence
<220> FEATURE:
<223> OTHER INFORMATION: Synthetic Construct

<400> SEQUENCE: 99
gtcaggtacc gcgggcgtgc actctcaggt ccagcttgtc cagtctgggg ctgaagtcaa    60
gaaacctgg                                                           69

<210> SEQ ID NO 100
<211> LENGTH: 66
<212> TYPE: DNA
<213> ORGANISM: Artificial Sequence
<220> FEATURE:
<223> OTHER INFORMATION: Synthetic Construct

<400> SEQUENCE: 100
agtaaaggtg tagccagaag ccttgcagga gaccttcacg ctcgagccag gtttcttgac    60
ttcagc                                                              66

<210> SEQ ID NO 101
<211> LENGTH: 67
<212> TYPE: DNA
<213> ORGANISM: Artificial Sequence
<220> FEATURE:
<223> OTHER INFORMATION: Synthetic Construct

<400> SEQUENCE: 101
gcttctggct acacctttac tagctatgtt atgcactggg taaggcaggc ccctggacag    60
ggtctgg                                                             67

<210> SEQ ID NO 102
<211> LENGTH: 66
<212> TYPE: DNA
<213> ORGANISM: Artificial Sequence
<220> FEATURE:
<223> OTHER INFORMATION: Synthetic Construct

<400> SEQUENCE: 102
ttgtactgag taccaccatt gtaaggatta atatatccaa tccattccag accctgtcca    60
ggggcc                                                              66
```

```
<210> SEQ ID NO 103
<211> LENGTH: 62
<212> TYPE: DNA
<213> ORGANISM: Artificial Sequence
<220> FEATURE:
<223> OTHER INFORMATION: Synthetic Construct

<400> SEQUENCE: 103
atggtggtac tcagtacaat gagaagttca aaggcaaggc cacaattact gcagacgaat    60
cc                                                                  62

<210> SEQ ID NO 104
<211> LENGTH: 63
<212> TYPE: DNA
<213> ORGANISM: Artificial Sequence
<220> FEATURE:
<223> OTHER INFORMATION: Synthetic Construct

<400> SEQUENCE: 104
cctcagatct caggctgctc agttccatgt aggctgtatt ggtggattcg tctgcagtaa    60
ttg                                                                 63

<210> SEQ ID NO 105
<211> LENGTH: 64
<212> TYPE: DNA
<213> ORGANISM: Artificial Sequence
<220> FEATURE:
<223> OTHER INFORMATION: Synthetic Construct

<400> SEQUENCE: 105
gagcagcctg agatctgagg acaccgcagt ctattactgt gcaagacgga ccttcccgta    60
ctac                                                                64

<210> SEQ ID NO 106
<211> LENGTH: 60
<212> TYPE: DNA
<213> ORGANISM: Artificial Sequence
<220> FEATURE:
<223> OTHER INFORMATION: Synthetic Construct

<400> SEQUENCE: 106
tgaggagact gtgaccaggg ttccttggcc ccagtagtca agtagtacg ggaaggtccg     60

<210> SEQ ID NO 107
<211> LENGTH: 59
<212> TYPE: DNA
<213> ORGANISM: Artificial Sequence
<220> FEATURE:
<223> OTHER INFORMATION: Synthetic Construct

<400> SEQUENCE: 107
tctatctaga tggagaccga taccctcctg ctatgggtcc tcctgctatg ggtcccagg     59

<210> SEQ ID NO 108
<211> LENGTH: 58
<212> TYPE: DNA
<213> ORGANISM: Artificial Sequence
<220> FEATURE:
<223> OTHER INFORMATION: Synthetic Construct

<400> SEQUENCE: 108
accctctaga attaggaaag tgcacttacg tttcagctcc accttggtcc cctgaccg      58

<210> SEQ ID NO 109
<211> LENGTH: 62
```

<212> TYPE: DNA
<213> ORGANISM: Artificial Sequence
<220> FEATURE:
<223> OTHER INFORMATION: Synthetic Construct

<400> SEQUENCE: 109
tcctgctatg ggtcccagga tcaaccggag atattcagat gacccagtct ccatcttccc     60
tc                                                                    62

<210> SEQ ID NO 110
<211> LENGTH: 60
<212> TYPE: DNA
<213> ORGANISM: Artificial Sequence
<220> FEATURE:
<223> OTHER INFORMATION: Synthetic Construct

<400> SEQUENCE: 110
gatctgcagg ttatggtgac cctatccccg acgctagcag agagggaaga tggagactgg     60

<210> SEQ ID NO 111
<211> LENGTH: 64
<212> TYPE: DNA
<213> ORGANISM: Artificial Sequence
<220> FEATURE:
<223> OTHER INFORMATION: Synthetic Construct

<400> SEQUENCE: 111
caccataacc tgcagatcta gtcagagcat tttacatagt aatggaaaca cctatttaga     60
atgg                                                                  64

<210> SEQ ID NO 112
<211> LENGTH: 60
<212> TYPE: DNA
<213> ORGANISM: Artificial Sequence
<220> FEATURE:
<223> OTHER INFORMATION: Synthetic Construct

<400> SEQUENCE: 112
gattagaagc ttgggagctt tgcctggctt ctgctggtac cattctaaat aggtgtttcc     60

<210> SEQ ID NO 113
<211> LENGTH: 66
<212> TYPE: DNA
<213> ORGANISM: Artificial Sequence
<220> FEATURE:
<223> OTHER INFORMATION: Synthetic Construct

<400> SEQUENCE: 113
gctcccaagc ttctaatcta taaagtttcc aaccgatttt ctggagtccc ttcacgcttc     60
agtggc                                                                66

<210> SEQ ID NO 114
<211> LENGTH: 61
<212> TYPE: DNA
<213> ORGANISM: Artificial Sequence
<220> FEATURE:
<223> OTHER INFORMATION: Synthetic Construct

<400> SEQUENCE: 114
gcagagagct gattgtgagg gtgaaatcgg tcccagatcc actgccactg aagcgtgaag     60
g                                                                     61

<210> SEQ ID NO 115
<211> LENGTH: 56

```
<212> TYPE: DNA
<213> ORGANISM: Artificial Sequence
<220> FEATURE:
<223> OTHER INFORMATION: Synthetic Construct

<400> SEQUENCE: 115
ctcacaatca gctctctgca gccagatgat ttcgccactt attactgctt tcaagg          56

<210> SEQ ID NO 116
<211> LENGTH: 63
<212> TYPE: DNA
<213> ORGANISM: Artificial Sequence
<220> FEATURE:
<223> OTHER INFORMATION: Synthetic Construct

<400> SEQUENCE: 116
ccaccttggt cccctgaccg aacgtgagag gagcatgtga accttgaaag cagtaataag      60
tgg                                                                    63

<210> SEQ ID NO 117
<211> LENGTH: 58
<212> TYPE: DNA
<213> ORGANISM: Artificial Sequence
<220> FEATURE:
<223> OTHER INFORMATION: Synthetic Construct

<400> SEQUENCE: 117
accctctaga attaggaaag tgcacttacg tttgatctcc accttggtcc cctgaccg        58

<210> SEQ ID NO 118
<211> LENGTH: 25
<212> TYPE: DNA
<213> ORGANISM: Artificial Sequence
<220> FEATURE:
<223> OTHER INFORMATION: Synthetic Construct

<400> SEQUENCE: 118
gcagcctgac atctgaggac agcgc                                            25

<210> SEQ ID NO 119
<211> LENGTH: 40
<212> TYPE: DNA
<213> ORGANISM: Artificial Sequence
<220> FEATURE:
<223> OTHER INFORMATION: Synthetic Construct

<400> SEQUENCE: 119
gactgcgctg tcctcagatg tcaggctgct cagttccatg                            40

<210> SEQ ID NO 120
<211> LENGTH: 31
<212> TYPE: DNA
<213> ORGANISM: Artificial Sequence
<220> FEATURE:
<223> OTHER INFORMATION: Synthetic Construct

<400> SEQUENCE: 120
ttggtggatg tgtctgcagt aattgtggcc t                                     31

<210> SEQ ID NO 121
<211> LENGTH: 31
<212> TYPE: DNA
<213> ORGANISM: Artificial Sequence
<220> FEATURE:
<223> OTHER INFORMATION: Synthetic Construct

<400> SEQUENCE: 121
```

```
actgcagaca catccaccaa tacagcctac a                           31
```

<210> SEQ ID NO 122
<211> LENGTH: 52
<212> TYPE: DNA
<213> ORGANISM: Artificial Sequence
<220> FEATURE:
<223> OTHER INFORMATION: Synthetic Construct

<400> SEQUENCE: 122

```
tcccagatcc tcagcctcca ctctgctgat cttgagggtg aaatcggtcc ca    52
```

<210> SEQ ID NO 123
<211> LENGTH: 44
<212> TYPE: DNA
<213> ORGANISM: Artificial Sequence
<220> FEATURE:
<223> OTHER INFORMATION: Synthetic Construct

<400> SEQUENCE: 123

```
agagtggagg ctgaggatct gggaacttat tactgctttc aagg             44
```

<210> SEQ ID NO 124
<211> LENGTH: 30
<212> TYPE: DNA
<213> ORGANISM: Artificial Sequence
<220> FEATURE:
<223> OTHER INFORMATION: Synthetic Construct

<400> SEQUENCE: 124

```
gacacatcct ccagtacagc ctacatggaa                             30
```

<210> SEQ ID NO 125
<211> LENGTH: 31
<212> TYPE: DNA
<213> ORGANISM: Artificial Sequence
<220> FEATURE:
<223> OTHER INFORMATION: Synthetic Construct

<400> SEQUENCE: 125

```
gctgtactgg aggatgtgtc tgaagtaatt g                           31
```

<210> SEQ ID NO 126
<211> LENGTH: 56
<212> TYPE: DNA
<213> ORGANISM: Artificial Sequence
<220> FEATURE:
<223> OTHER INFORMATION: Synthetic Construct

<400> SEQUENCE: 126

```
tcccagatct tcagcctcca ctctgctgat cttgagggtg aaatcggtcc cagatc  56
```

<210> SEQ ID NO 127
<211> LENGTH: 44
<212> TYPE: DNA
<213> ORGANISM: Artificial Sequence
<220> FEATURE:
<223> OTHER INFORMATION: Synthetic Construct

<400> SEQUENCE: 127

```
agagtggagg ctgaagatct gggaacttat tactgctttc aagg             44
```

<210> SEQ ID NO 128
<211> LENGTH: 30
<212> TYPE: DNA
<213> ORGANISM: Artificial Sequence

```
<220> FEATURE:
<223> OTHER INFORMATION: Synthetic Construct

<400> SEQUENCE: 128
gtcaagaaac ctggcgcgag cgtgaaggtc                                       30

<210> SEQ ID NO 129
<211> LENGTH: 33
<212> TYPE: DNA
<213> ORGANISM: Artificial Sequence
<220> FEATURE:
<223> OTHER INFORMATION: Synthetic Construct

<400> SEQUENCE: 129
caaaggcagg gtcacaatta ctgcagacga atc                                   33

<210> SEQ ID NO 130
<211> LENGTH: 32
<212> TYPE: DNA
<213> ORGANISM: Artificial Sequence
<220> FEATURE:
<223> OTHER INFORMATION: Synthetic Construct

<400> SEQUENCE: 130
taattgtgac cctgcctttg aacttctcat tg                                    32

<210> SEQ ID NO 131
<211> LENGTH: 39
<212> TYPE: DNA
<213> ORGANISM: Artificial Sequence
<220> FEATURE:
<223> OTHER INFORMATION: Synthetic Construct

<400> SEQUENCE: 131
ttcagacaca tccgccagta cagcctacat ggaactgag                             39

<210> SEQ ID NO 132
<211> LENGTH: 41
<212> TYPE: DNA
<213> ORGANISM: Artificial Sequence
<220> FEATURE:
<223> OTHER INFORMATION: Synthetic Construct

<400> SEQUENCE: 132
tactggcgga tgtgtctgaa gtaattgtga ccctgccttt g                          41

<210> SEQ ID NO 133
<211> LENGTH: 37
<212> TYPE: DNA
<213> ORGANISM: Artificial Sequence
<220> FEATURE:
<223> OTHER INFORMATION: Synthetic Construct

<400> SEQUENCE: 133
agcgtctgga atggatggga tatattaatc cttacaa                               37

<210> SEQ ID NO 134
<211> LENGTH: 38
<212> TYPE: DNA
<213> ORGANISM: Artificial Sequence
<220> FEATURE:
<223> OTHER INFORMATION: Synthetic Construct

<400> SEQUENCE: 134
tcccatccat tccagacgct gtccaggggc ctgcctta                              38
```

```
<210> SEQ ID NO 135
<211> LENGTH: 30
<212> TYPE: DNA
<213> ORGANISM: Artificial Sequence
<220> FEATURE:
<223> OTHER INFORMATION: Synthetic Construct

<400> SEQUENCE: 135
ggaccgattt caccttcaca atcagctctc                                      30

<210> SEQ ID NO 136
<211> LENGTH: 33
<212> TYPE: DNA
<213> ORGANISM: Artificial Sequence
<220> FEATURE:
<223> OTHER INFORMATION: Synthetic Construct

<400> SEQUENCE: 136
cagccagaag atatcgccac ttattactgc ttt                                   33

<210> SEQ ID NO 137
<211> LENGTH: 32
<212> TYPE: DNA
<213> ORGANISM: Artificial Sequence
<220> FEATURE:
<223> OTHER INFORMATION: Synthetic Construct

<400> SEQUENCE: 137
gtggcgatat cttctggctg cagagagctg at                                   32

<210> SEQ ID NO 138
<211> LENGTH: 330
<212> TYPE: PRT
<213> ORGANISM: Murine

<400> SEQUENCE: 138
```

Ala Thr Thr Thr Ala Pro Ser Val Tyr Pro Leu Val Pro Gly Cys Ser
 1               5                  10                  15

Asp Thr Ser Gly Ser Ser Val Thr Leu Gly Cys Leu Val Lys Gly Tyr
                20                  25                  30

Phe Pro Glu Pro Val Thr Val Lys Trp Asn Tyr Gly Ala Leu Ser Ser
            35                  40                  45

Gly Val Arg Thr Val Ser Ser Val Leu Gln Ser Gly Phe Tyr Ser Leu
        50                  55                  60

Ser Ser Leu Val Thr Val Pro Ser Ser Thr Trp Pro Ser Gln Thr Val
65                  70                  75                  80

Ile Cys Asn Val Ala His Pro Ala Ser Lys Thr Glu Leu Ile Lys Arg
                85                  90                  95

Ile Glu Pro Arg Ile Pro Lys Pro Ser Thr Pro Pro Gly Ser Ser Cys
            100                 105                 110

Pro Pro Gly Asn Ile Leu Gly Gly Pro Ser Val Phe Ile Phe Pro Pro
        115                 120                 125

Lys Pro Lys Asp Ala Leu Met Ile Ser Leu Thr Pro Lys Val Thr Cys
    130                 135                 140

Val Val Val Asp Val Ser Glu Asp Asp Pro Asp Val His Val Ser Trp
145                 150                 155                 160

Phe Val Asp Asn Lys Glu Val His Thr Ala Trp Thr Gln Pro Arg Glu
                165                 170                 175

Ala Gln Tyr Asn Ser Thr Phe Arg Val Val Ser Ala Leu Pro Ile Gln
            180                 185                 190

His Gln Asp Trp Met Arg Gly Lys Glu Phe Lys Cys Lys Val Asn Asn

```
                195                 200                 205
Lys Ala Leu Pro Ala Pro Ile Glu Arg Thr Ile Ser Lys Pro Lys Gly
    210                 215                 220

Arg Ala Gln Thr Pro Gln Val Tyr Thr Ile Pro Pro Arg Glu Gln
225                 230                 235                 240

Met Ser Lys Lys Lys Val Ser Leu Thr Cys Leu Val Thr Asn Phe Phe
                245                 250                 255

Ser Glu Ala Ile Ser Val Glu Trp Glu Arg Asn Gly Glu Leu Glu Gln
            260                 265                 270

Asp Tyr Lys Asn Thr Pro Pro Ile Leu Asp Ser Asp Gly Thr Tyr Phe
        275                 280                 285

Leu Tyr Ser Lys Leu Thr Val Asp Thr Asp Ser Trp Leu Gln Gly Glu
    290                 295                 300

Ile Phe Thr Cys Ser Val Val His Glu Ala Leu His Asn His His Thr
305                 310                 315                 320

Gln Lys Asn Leu Ser Arg Ser Pro Gly Lys
                325                 330

<210> SEQ ID NO 139
<211> LENGTH: 329
<212> TYPE: PRT
<213> ORGANISM: Homo sapiens

<400> SEQUENCE: 139

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                   245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 140
<211> LENGTH: 6
<212> TYPE: PRT
<213> ORGANISM: Artificial Sequence
<220> FEATURE:
<223> OTHER INFORMATION: Synthetic Construct

<400> SEQUENCE: 140

Ala Pro Ser Ser Lys Ser
 1               5

<210> SEQ ID NO 141
<211> LENGTH: 6
<212> TYPE: PRT
<213> ORGANISM: Artificial Sequence
<220> FEATURE:
<223> OTHER INFORMATION: Synthetic Construct

<400> SEQUENCE: 141

Val Pro Gly Cys Ser Asp
 1               5

<210> SEQ ID NO 142
<211> LENGTH: 4
<212> TYPE: PRT
<213> ORGANISM: Artificial Sequence
<220> FEATURE:
<223> OTHER INFORMATION: Synthetic Construct

<400> SEQUENCE: 142

Ser Ser Lys Ser
 1

<210> SEQ ID NO 143
<211> LENGTH: 4
<212> TYPE: PRT
<213> ORGANISM: Artificial Sequence
<220> FEATURE:
<223> OTHER INFORMATION: Synthetic Construct

<400> SEQUENCE: 143

Gly Cys Ser Asp
 1

<210> SEQ ID NO 144
<211> LENGTH: 5
<212> TYPE: PRT
<213> ORGANISM: Artificial Sequence
<220> FEATURE:
<223> OTHER INFORMATION: Synthetic Construct

<400> SEQUENCE: 144

His Thr Cys Pro Pro
```

-continued

```
<210> SEQ ID NO 145
<211> LENGTH: 5
<212> TYPE: PRT
<213> ORGANISM: Artificial Sequence
<220> FEATURE:
<223> OTHER INFORMATION: Synthetic Construct

<400> SEQUENCE: 145

Pro Pro Gly Ser Ser
 1               5

<210> SEQ ID NO 146
<211> LENGTH: 6
<212> TYPE: PRT
<213> ORGANISM: Artificial Sequence
<220> FEATURE:
<223> OTHER INFORMATION: Synthetic Construct

<400> SEQUENCE: 146

Ala Pro Ser Ser Lys Ser
 1               5

<210> SEQ ID NO 147
<211> LENGTH: 6
<212> TYPE: PRT
<213> ORGANISM: Artificial Sequence
<220> FEATURE:
<223> OTHER INFORMATION: Synthetic Construct

<400> SEQUENCE: 147

Val Pro Gly Cys Ser Asp
 1               5

<210> SEQ ID NO 148
<211> LENGTH: 4
<212> TYPE: PRT
<213> ORGANISM: Artificial Sequence
<220> FEATURE:
<223> OTHER INFORMATION: Synthetic Construct

<400> SEQUENCE: 148

Ser Ser Lys Ser
 1

<210> SEQ ID NO 149
<211> LENGTH: 4
<212> TYPE: PRT
<213> ORGANISM: Artificial Sequence
<220> FEATURE:
<223> OTHER INFORMATION: Synthetic Construct

<400> SEQUENCE: 149

Gly Cys Ser Asp
 1

<210> SEQ ID NO 150
<211> LENGTH: 10
<212> TYPE: PRT
<213> ORGANISM: Artificial Sequence
<220> FEATURE:
<223> OTHER INFORMATION: Synthetic Construct

<400> SEQUENCE: 150

Lys Ser Cys Asp Lys Thr His Thr Cys Pro
 1               5                  10
```

```
<210> SEQ ID NO 151
<211> LENGTH: 12
<212> TYPE: PRT
<213> ORGANISM: Artificial Sequence
<220> FEATURE:
<223> OTHER INFORMATION: Synthetic Construct

<400> SEQUENCE: 151

Arg Ile Pro Lys Pro Ser Thr Pro Pro Gly Ser Ser
 1               5                  10

<210> SEQ ID NO 152
<211> LENGTH: 5
<212> TYPE: PRT
<213> ORGANISM: Artificial Sequence
<220> FEATURE:
<223> OTHER INFORMATION: Synthetic Construct

<400> SEQUENCE: 152

Lys Ser Cys Asp Lys
 1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic Construct

<400> SEQUENCE: 153

Lys Ser Ser Cys Asp Lys
 1               5

<210> SEQ ID NO 154
<211> LENGTH: 5
<212> TYPE: PRT
<213> ORGANISM: Artificial Sequence
<220> FEATURE:
<223> OTHER INFORMATION: Synthetic Construct

<400> SEQUENCE: 154

Lys Ser Cys Asp Lys
 1               5

<210> SEQ ID NO 155
<211> LENGTH: 5
<212> TYPE: PRT
<213> ORGANISM: Artificial Sequence
<220> FEATURE:
<223> OTHER INFORMATION: Synthetic Construct

<400> SEQUENCE: 155

Lys Cys Ser Asp Lys
 1               5

<210> SEQ ID NO 156
<211> LENGTH: 5
<212> TYPE: PRT
<213> ORGANISM: Artificial Sequence
<220> FEATURE:
<223> OTHER INFORMATION: Synthetic Construct

<400> SEQUENCE: 156

Lys Ser Cys Asp Lys
 1               5

<210> SEQ ID NO 157
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 157

Lys Ser Asp Lys Ser Cys Asp Lys
1               5

<210> SEQ ID NO 158
<211> LENGTH: 5
<212> TYPE: PRT
<213> ORGANISM: Artificial Sequence
<220> FEATURE:
<223> OTHER INFORMATION: Synthetic Construct

<400> SEQUENCE: 158

Lys Ser Cys Asp Lys
1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic Construct

<400> SEQUENCE: 159

Lys Ser Cys Asp Lys Ser Asp Lys
1               5

<210> SEQ ID NO 160
<211> LENGTH: 11
<212> TYPE: PRT
<213> ORGANISM: Artificial Sequence
<220> FEATURE:
<223> OTHER INFORMATION: Synthetic Construct

<400> SEQUENCE: 160

Pro Val Thr Lys Ser Phe Asn Arg Gly Glu Cys
1               5                   10

<210> SEQ ID NO 161
<211> LENGTH: 13
<212> TYPE: PRT
<213> ORGANISM: Artificial Sequence
<220> FEATURE:
<223> OTHER INFORMATION: Synthetic Construct

<400> SEQUENCE: 161

Pro Val Thr Lys Ser Phe Asn Arg Gly Glu Gly Glu Cys
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Synthetic Construct

<400> SEQUENCE: 162

Pro Val Thr Lys Ser Phe Asn Arg Gly Gly Glu Gly Glu Cys
1               5                   10

<210> SEQ ID NO 163
<211> LENGTH: 15
<212> TYPE: PRT
```

```
<213> ORGANISM: Artificial Sequence
<220> FEATURE:
<223> OTHER INFORMATION: Synthetic Construct

<400> SEQUENCE: 163

Pro Val Thr Lys Ser Phe Asn Arg Gly Gly Gly Glu Gly Glu Cys
1               5                   10                  15

<210> SEQ ID NO 164
<211> LENGTH: 12
<212> TYPE: PRT
<213> ORGANISM: Artificial Sequence
<220> FEATURE:
<223> OTHER INFORMATION: Synthetic Construct

<400> SEQUENCE: 164

Pro Val Thr Lys Ser Phe Asn Arg Gly Gly Glu Cys
1               5                   10

<210> SEQ ID NO 165
<211> LENGTH: 13
<212> TYPE: PRT
<213> ORGANISM: Artificial Sequence
<220> FEATURE:
<223> OTHER INFORMATION: Synthetic Construct

<400> SEQUENCE: 165

Pro Val Thr Lys Ser Phe Asn Arg Gly Gly Gly Glu Cys
1               5                   10

<210> SEQ ID NO 166
<211> LENGTH: 14
<212> TYPE: PRT
<213> ORGANISM: Artificial Sequence
<220> FEATURE:
<223> OTHER INFORMATION: Synthetic Construct

<400> SEQUENCE: 166

Pro Val Thr Lys Ser Phe Asn Arg Gly Gly Gly Gly Glu Cys
1               5                   10

<210> SEQ ID NO 167
<211> LENGTH: 15
<212> TYPE: PRT
<213> ORGANISM: Artificial Sequence
<220> FEATURE:
<223> OTHER INFORMATION: Synthetic Construct

<400> SEQUENCE: 167

Pro Val Thr Lys Ser Phe Asn Arg Gly Gly Gly Gly Gly Glu Cys
1               5                   10                  15
```